US008669350B2

(12) United States Patent
Chou et al.

(10) Patent No.: US 8,669,350 B2
(45) Date of Patent: Mar. 11, 2014

(54) TNF RECEPTOR FC FUSION PROTEINS AND IN VIVO METHODS OF USE

(75) Inventors: Min-Yuan Chou, Taipei (TW); Wei-Chun Chiu, Zhubei (TW); Ya-Ping Lai, Zhudong Township, Hsinchu County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/588,752

(22) Filed: Aug. 17, 2012

(65) Prior Publication Data

US 2013/0164286 A1 Jun. 27, 2013

(30) Foreign Application Priority Data

Dec. 26, 2011 (TW) .............................. 100148544 A

(51) Int. Cl.
| | | |
|---|---|---|
| *C12P 21/08* | (2006.01) | |
| *C12P 21/06* | (2006.01) | |
| *C12N 1/20* | (2006.01) | |
| *C12N 15/00* | (2006.01) | |
| *C12N 5/00* | (2006.01) | |
| *C12N 5/02* | (2006.01) | |
| *C12N 5/07* | (2010.01) | |
| *C12N 5/16* | (2006.01) | |
| *C12N 15/74* | (2006.01) | |
| *C07H 21/04* | (2006.01) | |

(52) U.S. Cl.
USPC ................... 530/387.3; 424/134.1; 435/69.1; 435/252.3; 435/320.1; 435/325; 435/328; 435/471; 536/23.4

(58) Field of Classification Search
None
See application file for complete search history.

(56) References Cited

U.S. PATENT DOCUMENTS

| | | |
|---|---|---|
| 7,959,925 B2 | 6/2011 | Weinberg et al. |
| 2003/0207346 A1 | 11/2003 | Arathoon et al. |
| 2005/0255547 A1 | 11/2005 | Tschopp et al. |
| 2007/0010658 A1 | 1/2007 | Holtet et al. |
| 2007/0105199 A1 | 5/2007 | Yan et al. |
| 2007/0269449 A1 | 11/2007 | Walczak |
| 2011/0111494 A1 | 5/2011 | Hill et al. |

FOREIGN PATENT DOCUMENTS

| | | |
|---|---|---|
| EP | 1 235 853 B1 | 7/2009 |
| EP | 1 798 240 B1 | 4/2011 |
| EP | 2 069 392 B1 | 4/2011 |

OTHER PUBLICATIONS

Fan, Chia-Yu et al., "Production of multivalent protein binders using a self-trimerizing collagen-like peptide scaffold," The FASEB Journal, Nov. 2008, vol. 22, No. 11, pp. 3795-3804.
Muller, Nicole et al., "Activity of soluble OX40 ligand is enhanced by oligomerization and cell surface immobilization," FEBS Journal, 2008, vol. 275, No. 9, pp. 2296-2304.
Persikov, Anton V. et al., "Electrostatic interactions involving lysine make major contributions to collagen triple-helix stability," Biochemistry, 2005, vol. 44, No. 5, pp. 1414-1422.
Ridgway, John B.B. et al., "'Knobs-into-holes' engineering of antibdy CH3 domains for heavy chain heterodimerization," Protein Engineering, 1996, vol. 9, No. 7, pp. 617-621.
Wyzgol, Agnes et al., "Trimer stabilization, oligomerization, and antibody-mediated cell surface immobilization improve the activity of soluble trimers of CD27L, CD40L, 41BBL, and glucocorticoid-induced TNF receptor ligand," The Journal of Immunology, 2009, vol. 183, No. 3, pp. 1851-1861.

*Primary Examiner* — Robert Landsman
(74) *Attorney, Agent, or Firm* — Birch, Stewart, Kolasch & Birch, LLP

(57) ABSTRACT

The embodiments of the invention relate to compositions, methods, and kits comprising a fusion protein. The fusion proteins of the embodiments include monomer polypeptides which in one embodiment have at least a binding domain, an optional hinge region, a collagen-like domain and the Fc domain of a human IgG.

17 Claims, 11 Drawing Sheets

Table 1. Summary of various Fc-fusion molecules used in this study

| Name | Format | (n, m) value | Extracellular Secretion | Predominate structure |
|---|---|---|---|---|
| EnbCSFc | A | (10, N/A[1]) | Yes | Dimer |
| EnbhFcCS6 | B | (6, 6) | No | N/A |
| EnbCS4hFc | C | (4, 4) | Yes | Dimer |
| EnbCS5hFc | C | (5, 4) | Yes | Dimer, trimer and hexamer |
| EnbCS6hFc | C | (6, 6) | Yes | Hexamer |
| EnbCS6hFcM | D | (6, 6) | Yes | Trimer |
| bGalCS6hFc | E | (6, 6) | Yes | Hexamer |

[1] Not applicable

Fig. 2
Fig. 2A
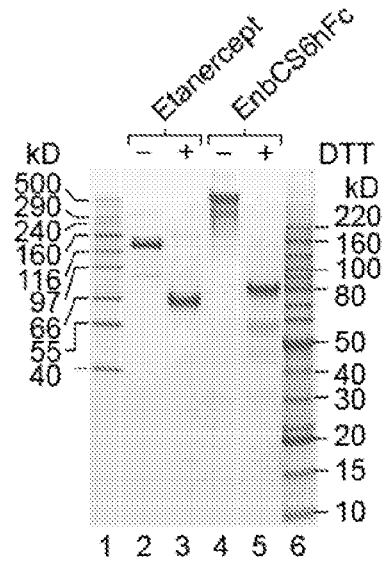
Fig. 2B
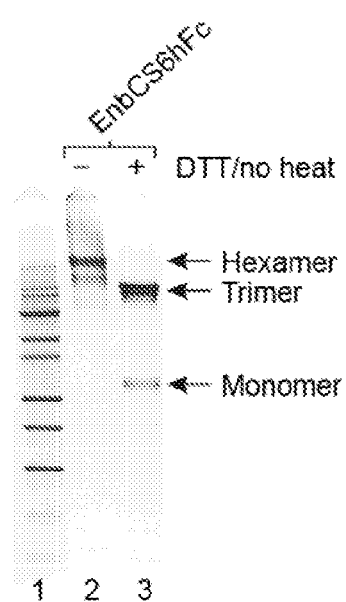
Fig. 2C
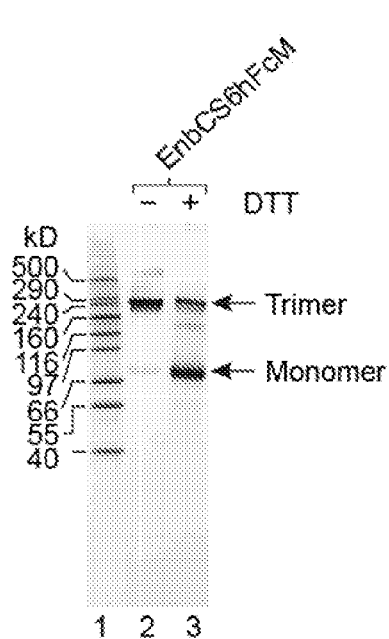
Fig. 2D
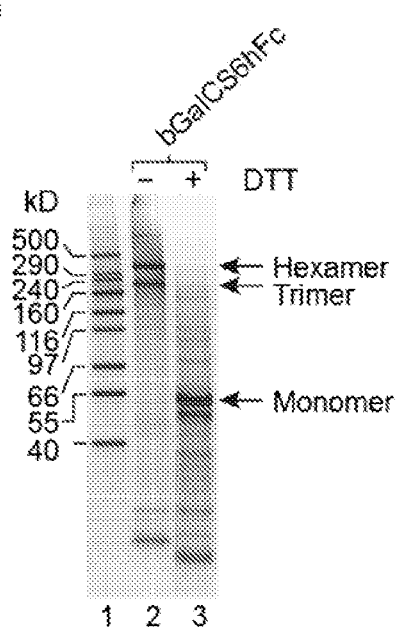

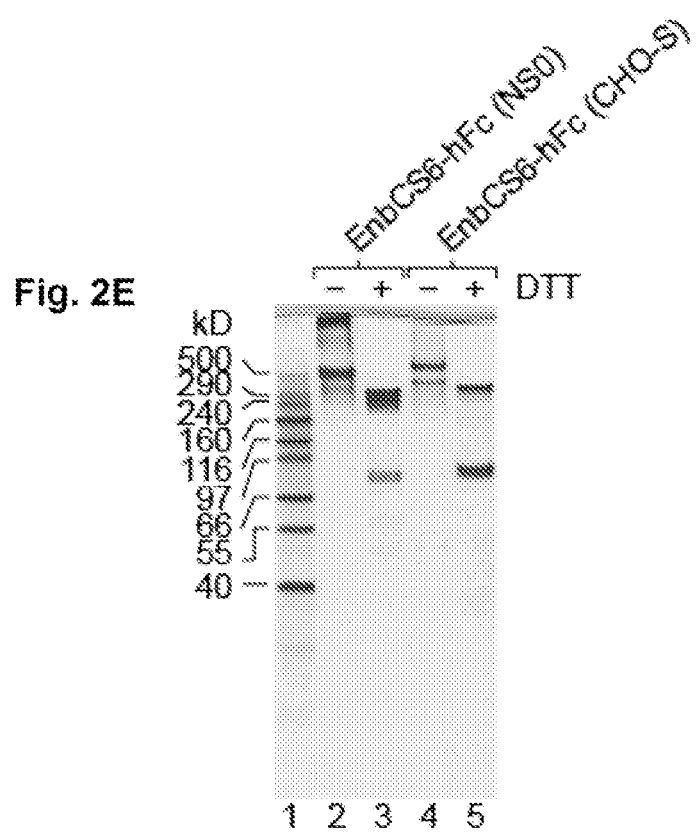

SEQUENCE LISTING

```
<160> NUMBER OF SEQ ID NOS: 86

<210> SEQ ID NO 1
<211> LENGTH: 536
<212> TYPE: PRT
<213> ORGANISM: Artificial Sequence
<220> FEATURE:
<223> OTHER INFORMATION: Synthetic construct

<400> SEQUENCE: 1

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30
```

-continued

```
Gln Val Ala Phe Thr Pro Tyr Ala Pro Glu Pro Gly Ser Thr Cys Arg
             35                  40                  45

Leu Arg Glu Tyr Tyr Asp Gln Thr Ala Gln Met Cys Cys Ser Lys Cys
 50                  55                  60

Ser Pro Gly Gln His Ala Lys Val Phe Cys Thr Lys Thr Ser Asp Thr
 65                  70                  75                  80

Val Cys Asp Ser Cys Glu Asp Ser Thr Tyr Thr Gln Leu Trp Asn Trp
                 85                  90                  95

Val Pro Glu Cys Leu Ser Cys Gly Ser Arg Cys Ser Ser Asp Gln Val
                100                 105                 110

Glu Thr Gln Ala Cys Thr Arg Glu Gln Asn Arg Ile Cys Thr Cys Arg
            115                 120                 125

Pro Gly Trp Tyr Cys Ala Leu Ser Lys Gln Glu Gly Cys Arg Leu Cys
        130                 135                 140

Ala Pro Leu Arg Lys Cys Arg Pro Gly Phe Gly Val Ala Arg Pro Gly
145                 150                 155                 160

Thr Glu Thr Ser Asp Val Val Cys Lys Pro Cys Ala Pro Gly Thr Phe
                165                 170                 175

Ser Asn Thr Thr Ser Ser Thr Asp Ile Cys Arg Pro His Gln Ile Cys
                180                 185                 190

Asn Val Val Ala Ile Pro Gly Asn Ala Ser Met Asp Ala Val Cys Thr
            195                 200                 205

Ser Thr Ser Pro Thr Arg Ser Met Ala Pro Gly Ala Val His Leu Pro
        210                 215                 220

Gln Pro Val Ser Thr Arg Ser Gln His Thr Gln Pro Thr Pro Glu Pro
225                 230                 235                 240

Ser Thr Ala Pro Ser Thr Ser Phe Leu Leu Pro Met Gly Pro Ser Pro
                245                 250                 255

Pro Ala Glu Gly Ser Thr Gly Asp Ala Ala Ala Glu Pro Lys Ser Gly
            260                 265                 270

Asp Lys Thr His Thr Cys Pro Pro Cys Pro Arg Ser Ile Pro Gly Pro
        275                 280                 285

Pro Gly Pro Pro Gly Pro Pro Gly Pro Pro Gly Pro Pro Gly Pro Pro
290                 295                 300

Gly Pro Pro Gly Pro Pro Gly Pro Pro Gly Pro Pro Gly Ile Cys Asp
305                 310                 315                 320

Pro Ser Leu Cys Thr Gly Pro Ser Val Phe Leu Phe Pro Pro Lys Pro
                325                 330                 335

Lys Asp Thr Leu Met Ile Ser Arg Thr Pro Glu Val Thr Cys Val Val
            340                 345                 350

Val Asp Val Ser His Glu Asp Pro Glu Val Lys Phe Asn Trp Tyr Val
        355                 360                 365

Asp Gly Val Glu Val His Asn Ala Lys Thr Lys Pro Arg Glu Glu Gln
    370                 375                 380

Tyr Asn Ser Thr Tyr Arg Val Val Ser Val Leu Thr Val Leu His Gln
385                 390                 395                 400

Asp Trp Leu Asn Gly Lys Glu Tyr Lys Cys Lys Val Ser Asn Lys Ala
                405                 410                 415

Leu Pro Ala Pro Ile Glu Lys Thr Ile Ser Lys Ala Lys Gly Gln Pro
            420                 425                 430

Arg Glu Pro Gln Val Tyr Thr Leu Pro Pro Ser Arg Asp Glu Leu Thr
        435                 440                 445

Lys Asn Gln Val Ser Leu Thr Cys Leu Val Lys Gly Phe Tyr Pro Ser
450                 455                 460
```

```
Asp Ile Ala Val Glu Trp Glu Ser Asn Gly Gln Pro Glu Asn Asn Tyr
465                 470                 475                 480

Lys Thr Thr Pro Pro Val Leu Asp Ser Asp Gly Ser Phe Phe Leu Tyr
                485                 490                 495

Ser Lys Leu Thr Val Asp Lys Ser Arg Trp Gln Gln Gly Asn Val Phe
            500                 505                 510

Ser Cys Ser Val Met His Glu Ala Leu His Asn His Tyr Thr Gln Lys
        515                 520                 525

Ser Leu Ser Leu Ser Pro Gly Lys
        530                 535

<210> SEQ ID NO 2
<211> LENGTH: 1611
<212> TYPE: DNA
<213> ORGANISM: Artificial Sequence
<220> FEATURE:
<223> OTHER INFORMATION: Synthetic construct

<400> SEQUENCE: 2
atggagacag acacactcct gctatgggta ctgctgctct gggttccagg ttccactggt      60
gacgcggccc agccggccag gcgcgccttg cccgcccagg tggcatttac accctacgcc     120
ccggagcccg ggagcacatg ccggctcaga gaatactatg accagacagc tcagatgtgc     180
tgcagcaaat gctcgccggg ccaacatgca aaagtcttct gtaccaagac ctcggacacc     240
gtgtgtgact cctgtgagga cagcacatac acccagctct ggaactgggt tcccgagtgc     300
ttgagctgtg gctcccgctg tagctctgac caggtggaaa ctcaagcctg cactcgggaa     360
cagaaccgca tctgcacctg caggcccggc tggtactgcg cgctgagcaa gcaggagggg     420
tgccggctgt gcgcgccgct gcgcaagtgc cgcccgggct cggcgtggc cagaccagga      480 actgaaacat cagacgtggt gtgcaagccc tgtgccccgg gacgttctc aacacgact      540 tcatccacgg atatttgcag gccccaccag atctgtaacg tggtggccat ccctgggaat     600
gcaagcatgg atgcagtctg cacgtccacg tcccccaccc ggagtatggc ccaggggca     660 gtacacttac cccagccagt gtccacacga tcccaacaca cgcagccaac tcagaaccc      720 agcactgctc caagcacctc cttcctgctc ccaatgggcc ccagcccccc agctgaaggg     780
agcactggcg acgcggccgc tgagcccaaa tctggtgaca aaactcacac atgcccaccg     840
tgcccaagat ctattcctgg ccacctggt ccccaggtc ctccaggacc cccagggccc       900
ccaggccccc ccgggccgcc tggaccccca gggccaccag ccccccagg catctgcgac      960 ccatcactat gtaccggtcc gtcagtcttc ctcttccccc caaaacccaa ggacaccctc    1020
atgatctccc ggaccctga ggtcacatgc gtggtggtgg acgtgagcca cgaagaccct     1080
gaggtcaagt tcaactggta cgtggacggc gtggaggtgc ataatgccaa gacaaagccg    1140
cgggaggagc agtacaacag cacgtaccgt gtggtcagcg tcctcaccgt cctgcaccag    1200
gactggctga atggcaagga gtacaagtgc aaggtctcca caaagccct cccagccccc     1260 atcgagaaaa ccatctccaa agccaaaggg cagccccgag aaccacaggt gtacaccctg    1320
cccccatccc gggatgagct gaccaagaac caggtcagcc tgacctgcct ggtcaaaggc    1380
ttctatccca gcgacatcgc cgtggagtgg gagagcaatg ggcagccgga gaacaactac    1440
aagaccacgc ctcccgtgct ggactccgac ggctccttct tcctctacag caagctcacc    1500
gtggacaaga gcaggtggca gcaggggaac gtcttctcat gctccgtgat gcatgaggct    1560
ctgcacaacc actacacgca gaagagcctc tccctgtctc cgggtaaatg a             1611
```

<210> SEQ ID NO 3
<211> LENGTH: 559
<212> TYPE: PRT
<213> ORGANISM: Artificial Sequence
<220> FEATURE:
<223> OTHER INFORMATION: Synthetic construct

<400> SEQUENCE: 3

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30

Gln Val Ala Phe Thr Pro Tyr Ala Pro Glu Pro Gly Ser Thr Cys Arg
        35                  40                  45

Leu Arg Glu Tyr Tyr Asp Gln Thr Ala Gln Met Cys Cys Ser Lys Cys
    50                  55                  60

Ser Pro Gly Gln His Ala Lys Val Phe Cys Thr Lys Thr Ser Asp Thr
65                  70                  75                  80

Val Cys Asp Ser Cys Glu Asp Ser Thr Tyr Thr Gln Leu Trp Asn Trp
                85                  90                  95

Val Pro Glu Cys Leu Ser Cys Gly Ser Arg Cys Ser Ser Asp Gln Val
            100                 105                 110

Glu Thr Gln Ala Cys Thr Arg Glu Gln Asn Arg Ile Cys Thr Cys Arg
        115                 120                 125

Pro Gly Trp Tyr Cys Ala Leu Ser Lys Gln Glu Gly Cys Arg Leu Cys
    130                 135                 140

Ala Pro Leu Arg Lys Cys Arg Pro Gly Phe Gly Val Ala Arg Pro Gly
145                 150                 155                 160

Thr Glu Thr Ser Asp Val Val Cys Lys Pro Cys Ala Pro Gly Thr Phe
                165                 170                 175

Ser Asn Thr Thr Ser Ser Thr Asp Ile Cys Arg Pro His Gln Ile Cys
            180                 185                 190

Asn Val Val Ala Ile Pro Gly Asn Ala Ser Met Asp Ala Val Cys Thr
        195                 200                 205

Ser Thr Ser Pro Thr Arg Ser Met Ala Pro Gly Ala Val His Leu Pro
    210                 215                 220

Gln Pro Val Ser Thr Arg Ser Gln His Thr Gln Pro Thr Pro Glu Pro
225                 230                 235                 240

Ser Thr Ala Pro Ser Thr Ser Phe Leu Leu Pro Met Gly Pro Ser Pro
                245                 250                 255

Pro Ala Glu Gly Ser Thr Gly Asp Ala Ala Ala Glu Pro Lys Ser Cys
            260                 265                 270

Asp Lys Thr His Thr Cys Pro Pro Cys Pro Ala Pro Glu Leu Leu Gly
        275                 280                 285

Gly Pro Ser Val Phe Leu Phe Pro Pro Lys Pro Lys Asp Thr Leu Met
    290                 295                 300

Ile Ser Arg Thr Pro Glu Val Thr Cys Val Val Val Asp Val Ser His
305                 310                 315                 320

Glu Asp Pro Glu Val Lys Phe Asn Trp Tyr Val Asp Gly Val Glu Val
                325                 330                 335

His Asn Ala Lys Thr Lys Pro Arg Glu Glu Gln Tyr Asn Ser Thr Tyr
            340                 345                 350

Arg Val Val Ser Val Leu Thr Val Leu His Gln Asp Trp Leu Asn Gly
        355                 360                 365

Lys Glu Tyr Lys Cys Lys Val Ser Asn Lys Ala Leu Pro Ala Pro Ile
```

|     |     | 370 |     |     | 375 |     |     |     | 380 |     |     |
| --- | --- | --- | --- | --- | --- | --- | --- | --- | --- | --- | --- |

Glu Lys Thr Ile Ser Lys Ala Lys Gly Gln Pro Arg Glu Pro Gln Val
385                 390                 395                 400

Tyr Thr Leu Pro Pro Ser Arg Asp Glu Leu Thr Lys Asn Gln Val Ser
            405                 410                 415

Leu Thr Cys Leu Val Lys Gly Phe Tyr Pro Ser Asp Ile Ala Val Glu
        420                 425                 430

Trp Glu Ser Asn Gly Gln Pro Glu Asn Asn Tyr Lys Thr Thr Pro Pro
            435                 440                 445

Val Leu Asp Ser Asp Gly Ser Phe Phe Leu Tyr Ser Lys Leu Thr Val
    450                 455                 460

Asp Lys Ser Arg Trp Gln Gln Gly Asn Val Phe Ser Cys Ser Val Met
465                 470                 475                 480

His Glu Ala Leu His Asn His Tyr Thr Gln Lys Ser Leu Ser Leu Ser
                485                 490                 495

Pro Gly Lys Gly Gly Gly Ser Gly Pro Gly Pro Pro Gly Pro
            500                 505                 510

Pro Gly Pro Pro Gly Pro Pro Gly Pro Pro Gly Glu Lys Gly Glu Lys
            515                 520                 525

Gly Asp Pro Gly Pro Lys Gly Asp Pro Gly Pro Pro Gly Pro Pro Gly
    530                 535                 540

Pro Pro Gly Pro Pro Gly Pro Pro Gly Pro Pro Gly Gly Thr Gly
545                 550                 555

```
<210> SEQ ID NO 4
<211> LENGTH: 1680
<212> TYPE: DNA
<213> ORGANISM: Artificial Sequence
<220> FEATURE:
<223> OTHER INFORMATION: Synthetic construct

<400> SEQUENCE: 4
atggagacag acacactcct gctatgggta ctgctgctct gggttccagg ttccactggt    60
gacgcggccc agccggccag cgcgccttg cccgcccagg tggcatttac accctacgcc    120
ccggagcccg ggagcacatg ccggctcaga gaatactatg accagacagc tcagatgtgc    180
tgcagcaaat gctcgccggg caacatgca aaagtcttct gtaccaagac ctcggacacc    240
gtgtgtgact cctgtgagga cagcacatac acccagctct ggaactgggt tcccgagtgc    300
ttgagctgtg gctcccgctg tagctctgac caggtggaaa ctcaagcctg cactcgggaa    360
cagaaccgca tctgcacctg caggcccggc tggtactgcg cgctgagcaa gcaggagggg    420
tgccggctgt gcgcgccgct cgcaagtgc cgcccgggct cggcgtggc cagaccagga    480 actgaaacat cagacgtggt gtgcaagccc tgtgccccgg ggacgttctc caacacgact    540
tcatccacgg atatttgcag gccccaccag atctgtaacg tggtggccat ccctgggaat    600
gcaagcatgg atgcagtctg cacgtccacg tccccaccc ggagtatggc cccaggggca    660
gtacacttac cccagccagt gtccacacga tcccaacaca cgcagccaac tccagaaccc    720
agcactgctc caagcaccct cttcctgctc ccaatgggcc ccagccccc agctgaaggg    780 agcactggcg acgcggccgc tgagcccaaa tcttgtgaca aaactcacac atgcccaccg    840
tgcccagcac ctgaactcct ggggggaccg tcagtcttcc tcttcccccc aaaacccaag    900
gacaccctca tgatctcccg gacccctgag gtcacatgcg tggtggtgga cgtgagccac    960
gaagaccctg aggtcaagtt caactggtac gtggacggcg tggaggtgca taatgccaag    1020
acaaagccgc gggaggagca gtacaacagc acgtaccgtg tggtcagcgt cctcaccgtc    1080
```

```
ctgcaccagg actggctgaa tggcaaggag tacaagtgca aggtctccaa caaagccctc    1140
ccagccccca tcgagaaaac catctccaaa gccaagggc agccccgaga ccacaggtg     1200 tacaccctgc ccccatcccg ggatgagctg accaagaacc aggtcagcct gacctgcctg    1260
gtcaaaggct tctatcccag cgacatcgcc gtggagtggg agagcaatgg gcagccggag    1320
aacaactaca agaccacgcc tcccgtgctg gactccgacg gctccttctt cctctacagc    1380
aagctcaccg tggacaagag caggtggcag caggggaacg tcttctcatg ctccgtgatg    1440
catgaggctc tgcacaacca ctacacgcag aagagcctct ccctgtctcc gggtaaaggt    1500
ggaggcggtt cagggccacc tggtccccca ggtcctccag gaccccaggg gccccctgga    1560
cctccaggtg agaagggtga gaaaggagat ccaggtccta agggagaccc tggtccacca    1620
ggacctcctg gccctcccgg gccgcctgga ccccaggcc tcctggtgg aaccggttga    1680
```

<210> SEQ ID NO 5
<211> LENGTH: 541
<212> TYPE: PRT
<213> ORGANISM: Artificial Sequence
<220> FEATURE:
<223> OTHER INFORMATION: Synthetic construct

<400> SEQUENCE: 5

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30

Gln Val Ala Phe Thr Pro Tyr Ala Pro Glu Pro Gly Ser Thr Cys Arg
        35                  40                  45

Leu Arg Glu Tyr Tyr Asp Gln Thr Ala Gln Met Cys Cys Ser Lys Cys
    50                  55                  60

Ser Pro Gly Gln His Ala Lys Val Phe Cys Thr Lys Thr Ser Asp Thr
65                  70                  75                  80

Val Cys Asp Ser Cys Glu Asp Ser Thr Tyr Thr Gln Leu Trp Asn Trp
                85                  90                  95

Val Pro Glu Cys Leu Ser Cys Gly Ser Arg Cys Ser Ser Asp Gln Val
            100                 105                 110

Glu Thr Gln Ala Cys Thr Arg Glu Gln Asn Arg Ile Cys Thr Cys Arg
        115                 120                 125

Pro Gly Trp Tyr Cys Ala Leu Ser Lys Gln Glu Gly Cys Arg Leu Cys
    130                 135                 140

Ala Pro Leu Arg Lys Cys Arg Pro Gly Phe Gly Val Ala Arg Pro Gly
145                 150                 155                 160

Thr Glu Thr Ser Asp Val Val Cys Lys Pro Cys Ala Pro Gly Thr Phe
                165                 170                 175

Ser Asn Thr Thr Ser Ser Thr Asp Ile Cys Arg Pro His Gln Ile Cys
            180                 185                 190

Asn Val Val Ala Ile Pro Gly Asn Ala Ser Met Asp Ala Val Cys Thr
        195                 200                 205

Ser Thr Ser Pro Thr Arg Ser Met Ala Pro Gly Ala Val His Leu Pro
    210                 215                 220

Gln Pro Val Ser Thr Arg Ser Gln His Thr Gln Pro Thr Pro Glu Pro
225                 230                 235                 240

Ser Thr Ala Pro Ser Thr Ser Phe Leu Leu Pro Met Gly Pro Ser Pro
                245                 250                 255

Pro Ala Glu Gly Ser Thr Gly Asp Ala Ala Ala Glu Pro Lys Ser Gly
```

```
                  260                 265                 270
Asp Lys Thr His Thr Cys Pro Pro Cys Pro Ala Pro Glu Leu Leu Gly
        275                 280                 285
Gly Pro Pro Gly Pro Pro Gly Pro Pro Gly Pro Pro Gly Glu Lys Gly
    290                 295                 300
Glu Lys Gly Asp Pro Gly Pro Lys Gly Asp Ile Gly Pro Pro Gly Pro
305                 310                 315                 320
Pro Gly Pro Pro Gly Pro Pro Gly Gly Thr Gly Pro Ser Val Phe Leu
                325                 330                 335
Phe Pro Pro Lys Pro Lys Asp Thr Leu Met Ile Ser Arg Thr Pro Glu
        340                 345                 350
Val Thr Cys Val Val Val Asp Val Ser His Glu Asp Pro Glu Val Lys
        355                 360                 365
Phe Asn Trp Tyr Val Asp Gly Val Glu Val His Asn Ala Lys Thr Lys
        370                 375                 380
Pro Arg Glu Glu Gln Tyr Asn Ser Thr Tyr Arg Val Val Ser Val Leu
385                 390                 395                 400
Thr Val Leu His Gln Asp Trp Leu Asn Gly Lys Glu Tyr Lys Cys Lys
                405                 410                 415
Val Ser Asn Lys Ala Leu Pro Ala Pro Ile Glu Lys Thr Ile Ser Lys
                420                 425                 430
Ala Lys Gly Gln Pro Arg Glu Pro Gln Val Tyr Thr Leu Pro Pro Ser
        435                 440                 445
Arg Asp Glu Leu Thr Lys Asn Gln Val Ser Leu Thr Cys Leu Val Lys
        450                 455                 460
Gly Phe Tyr Pro Ser Asp Ile Ala Val Glu Trp Glu Ser Asn Gly Gln
465                 470                 475                 480
Pro Glu Asn Asn Tyr Lys Thr Thr Pro Pro Val Leu Asp Ser Asp Gly
                485                 490                 495
Ser Phe Phe Leu Tyr Ser Lys Leu Thr Val Asp Lys Ser Arg Trp Gln
        500                 505                 510
Gln Gly Asn Val Phe Ser Cys Ser Val Met His Glu Ala Leu His Asn
        515                 520                 525
His Tyr Thr Gln Lys Ser Leu Ser Leu Ser Pro Gly Lys
        530                 535                 540

<210> SEQ ID NO 6
<211> LENGTH: 1626
<212> TYPE: DNA
<213> ORGANISM: Artificial Sequence
<220> FEATURE:
<223> OTHER INFORMATION: Synthetic construct

<400> SEQUENCE: 6
atggagacag acacactcct gctatgggta ctgctgctct gggttccagg ttccactggt      60
gacgcggccc agccggccag gcgcgccttg cccgcccagg tggcatttac accctacgcc     120
ccggagcccg ggagcacatg ccggctcaga gaatactatg accagacagc tcagatgtgc     180
tgcagcaaat gctcgccggg ccaacatgca aaagtcttct gtaccaagac ctcggacacc     240
gtgtgtgact cctgtgagga cagcacatac acccagctct ggaactgggt tcccgagtgc     300
ttgagctgtg gctcccgctg tagctctgac caggtggaaa tcaagcctg cactcgggaa     360 cagaaccgca tctgcacctg caggcccggc tggtactgcg cgctgagcaa gcaggagggg     420
tgccggctgt gcgcgccgct gcgcaagtgc cgcccgggct cggcgtggc cagaccagga     480 actgaaacat cagacgtggt gtgcaagccc tgtgccccgg ggacgttctc caacacgact     540
```

```
tcatccacgg atatttgcag gccccaccag atctgtaacg tggtggccat ccctgggaat    600
gcaagcatgg atgcagtctg cacgtccacg tcccccaccc ggagtatggc cccaggggca    660
gtacacttac cccagccagt gtccacacga tcccaacaca cgcagccaac tccagaaccc    720
agcactgctc caagcacctc cttcctgctc ccaatgggcc ccagcccccc agctgaaggg    780
agcactggcg acgcggccgc tgagcccaaa tctggtgaca aaactcacac atgcccaccg    840
tgcccagcac ctgaactcct gggaggtcct ccaggacccc cagggccccc tgggcccct    900 ggtgagaagg gtgagaaagg agatccaggt cctaagggag acatcggccc tcccgggccg    960
cctggacccc caggccctcc tggtggaacc ggtccgtcag tcttcctctt cccccaaaa    1020 cccaaggaca ccctcatgat ctcccggacc cctgaggtca catgcgtggt ggtggacgtg    1080
agccacgaag accctgaggt caagttcaac tggtacgtgg acggcgtgga ggtgcataat    1140
gccaagacaa agccgcggga ggagcagtac aacagcacgt accgtgtggt cagcgtcctc    1200
accgtcctgc accaggactg gctgaatggc aaggagtaca agtgcaaggt ctccaacaaa    1260
gccctcccag cccccatcga gaaaaccatc tccaaagcca agggcagccc cgagaaccca    1320
caggtgtaca ccctgccccc atcccgggat gagctgacca gaaccaggt cagcctgacc    1380 tgcctggtca aaggcttcta tcccagcgac atcgccgtgg agtgggagag caatgggcag    1440
ccggagaaca actacaagac cacgcctccc gtgctggact ccgacggctc cttcttcctc    1500
tacagcaagc tcaccgtgga caagagcagg tggcagcagg ggaacgtctt ctcatgctcc    1560
gtgatgcatg aggctctgca caaccactac acgcagaaga gcctctccct gtctccgggt    1620
aaatga                                                               1626
```

<210> SEQ ID NO 7
<211> LENGTH: 544
<212> TYPE: PRT
<213> ORGANISM: Artificial Sequence
<220> FEATURE:
<223> OTHER INFORMATION: Synthetic construct

<400> SEQUENCE: 7

```
Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30

Gln Val Ala Phe Thr Pro Tyr Ala Pro Glu Pro Gly Ser Thr Cys Arg
        35                  40                  45

Leu Arg Glu Tyr Tyr Asp Gln Thr Ala Gln Met Cys Cys Ser Lys Cys
    50                  55                  60

Ser Pro Gly Gln His Ala Lys Val Phe Cys Thr Lys Thr Ser Asp Thr
65                  70                  75                  80

Val Cys Asp Ser Cys Glu Asp Ser Thr Tyr Thr Gln Leu Trp Asn Trp
                85                  90                  95

Val Pro Glu Cys Leu Ser Cys Gly Ser Arg Cys Ser Ser Asp Gln Val
            100                 105                 110

Glu Thr Gln Ala Cys Thr Arg Glu Gln Asn Arg Ile Cys Thr Cys Arg
        115                 120                 125

Pro Gly Trp Tyr Cys Ala Leu Ser Lys Gln Glu Gly Cys Arg Leu Cys
    130                 135                 140

Ala Pro Leu Arg Lys Cys Arg Pro Gly Phe Gly Val Ala Arg Pro Gly
145                 150                 155                 160

Thr Glu Thr Ser Asp Val Val Cys Lys Pro Cys Ala Pro Gly Thr Phe
```

```
            165                 170                 175
Ser Asn Thr Thr Ser Thr Asp Ile Cys Arg Pro His Gln Ile Cys
            180                 185                 190

Asn Val Val Ala Ile Pro Gly Asn Ala Ser Met Asp Ala Val Cys Thr
            195                 200                 205

Ser Thr Ser Pro Thr Arg Ser Met Ala Pro Gly Ala Val His Leu Pro
        210                 215                 220

Gln Pro Val Ser Thr Arg Ser Gln His Thr Gln Pro Thr Pro Glu Pro
225                 230                 235                 240

Ser Thr Ala Pro Ser Thr Ser Phe Leu Leu Pro Met Gly Pro Ser Pro
                245                 250                 255

Pro Ala Glu Gly Ser Thr Gly Asp Ala Ala Glu Pro Lys Ser Gly
            260                 265                 270

Asp Lys Thr His Thr Cys Pro Pro Cys Pro Ala Pro Glu Leu Leu Gly
            275                 280                 285

Gly Pro Pro Gly Pro Pro Gly Pro Pro Gly Pro Pro Gly Pro Pro Gly
            290                 295                 300

Glu Lys Gly Glu Lys Gly Asp Pro Gly Pro Lys Gly Asp Ile Gly Pro
305                 310                 315                 320

Pro Gly Pro Pro Gly Pro Pro Gly Pro Gly Gly Thr Gly Pro Ser
                325                 330                 335

Val Phe Leu Phe Pro Pro Lys Pro Lys Asp Thr Leu Met Ile Ser Arg
            340                 345                 350

Thr Pro Glu Val Thr Cys Val Val Val Asp Val Ser His Glu Asp Pro
            355                 360                 365

Glu Val Lys Phe Asn Trp Tyr Val Asp Gly Val Glu Val His Asn Ala
        370                 375                 380

Lys Thr Lys Pro Arg Glu Glu Gln Tyr Asn Ser Thr Tyr Arg Val Val
385                 390                 395                 400

Ser Val Leu Thr Val Leu His Gln Asp Trp Leu Asn Gly Lys Glu Tyr
                405                 410                 415

Lys Cys Lys Val Ser Asn Lys Ala Leu Pro Ala Pro Ile Glu Lys Thr
            420                 425                 430

Ile Ser Lys Ala Lys Gly Gln Pro Arg Glu Pro Gln Val Tyr Thr Leu
            435                 440                 445

Pro Pro Ser Arg Asp Glu Leu Thr Lys Asn Gln Val Ser Leu Thr Cys
        450                 455                 460

Leu Val Lys Gly Phe Tyr Pro Ser Asp Ile Ala Val Glu Trp Glu Ser
465                 470                 475                 480

Asn Gly Gln Pro Glu Asn Asn Tyr Lys Thr Thr Pro Pro Val Leu Asp
                485                 490                 495

Ser Asp Gly Ser Phe Phe Leu Tyr Ser Lys Leu Thr Val Asp Lys Ser
            500                 505                 510

Arg Trp Gln Gln Gly Asn Val Phe Ser Cys Ser Val Met His Glu Ala
            515                 520                 525

Leu His Asn His Tyr Thr Gln Lys Ser Leu Ser Leu Ser Pro Gly Lys
        530                 535                 540

<210> SEQ ID NO 8
<211> LENGTH: 1635
<212> TYPE: DNA
<213> ORGANISM: Artificial Sequence
<220> FEATURE:
<223> OTHER INFORMATION: Synthetic construct

<400> SEQUENCE: 8
```

-continued

| | |
|---|---|
| atggagacag acacactcct gctatgggta ctgctgctct gggttccagg ttccactggt | 60 |
| gacgcggccc agccggccag gcgcgccttg cccgcccagg tggcatttac accctacgcc | 120 |
| ccggagcccg ggagcacatg ccggctcaga gaatactatg accagacagc tcagatgtgc | 180 |
| tgcagcaaat gctcgccggg ccaacatgca aaagtcttct gtaccaagac ctcggacacc | 240 |
| gtgtgtgact cctgtgagga cagcacatac acccagctct ggaactgggt tcccgagtgc | 300 |
| ttgagctgtg gctcccgctg tagctctgac caggtggaaa ctcaagcctg cactcgggaa | 360 |
| cagaaccgca tctgcacctg caggcccggc tggtactgcg cgctgagcaa gcaggagggg | 420 |
| tgccggctgt gcgcgccgct gcgcaagtgc cgcccgggct cggcgtggc cagaccagga | 480 |
| actgaaacat cagacgtggt gtgcaagccc tgtgccccgg gacgttctc caacacgact | 540 |
| tcatccacgg atatttgcag gccccaccag atctgtaacg tggtggccat ccctgggaat | 600 |
| gcaagcatgg atgcagtctg cacgtccacg tcccccaccc ggagtatggc cccaggggca | 660 |
| gtacacttac cccagccagt gtccacacga tcccaacaca cgcagccaac tccagaaccc | 720 |
| agcactgctc caagcacctc cttcctgctc ccaatgggcc ccagcccccc agctgaaggg | 780 |
| agcactggcg acgcggccgc tgagcccaaa tctggtgaca aaactcacac atgcccaccg | 840 |
| tgcccagcac ctgaactcct gggaggtcct ccaggacccc cagggccccc tgggccccct | 900 |
| gggcccctg gtgagaaggg tgagaaagga gatccaggtc ctaagggaga catcggccct | 960 |
| cccgggccgc ctggaccccc aggccctcct ggtggaaccg gtccgtcagt cttcctcttc | 1020 |
| cccccaaaac ccaaggacac cctcatgatc tcccggaccc ctgaggtcac atgcgtggtg | 1080 |
| gtggacgtga gccacgaaga ccctgaggtc aagttcaact ggtacgtgga cggcgtggag | 1140 |
| gtgcataatg ccaagacaaa gccgcgggag gagcagtaca acagcacgta ccgtgtggtc | 1200 |
| agcgtcctca ccgtcctgca ccaggactgg ctgaatggca aggagtacaa gtgcaaggtc | 1260 |
| tccaacaaag ccctcccagc ccccatcgag aaaaccatct ccaaagccaa agggcagccc | 1320 |
| cgagaaccac aggtgtacac cctgccccca tcccgggatg agctgaccaa gaaccaggtc | 1380 |
| agcctgacct gcctggtcaa aggcttctat cccagcgaca tcgccgtgga gtgggagagc | 1440 |
| aatgggcagc cggagaacaa ctacaagacc acgcctcccg tgctggactc cgacggctcc | 1500 |
| ttcttcctct acagcaagct caccgtggac aagagcaggt ggcagcaggg gaacgtcttc | 1560 |
| tcatgctccg tgatgcatga ggctctgcac aaccactaca cgcagaagag cctctccctg | 1620 |
| tctccgggta aatga | 1635 |

<210> SEQ ID NO 9
<211> LENGTH: 553
<212> TYPE: PRT
<213> ORGANISM: Artificial Sequence
<220> FEATURE:
<223> OTHER INFORMATION: Synthetic construct

<400> SEQUENCE: 9

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30

Gln Val Ala Phe Thr Pro Tyr Ala Pro Glu Pro Gly Ser Thr Cys Arg
        35                  40                  45

Leu Arg Glu Tyr Tyr Asp Gln Thr Ala Gln Met Cys Cys Ser Lys Cys
    50                  55                  60

Ser Pro Gly Gln His Ala Lys Val Phe Cys Thr Lys Thr Ser Asp Thr

-continued

```
               65                  70                  75                  80
        Val Cys Asp Ser Cys Glu Asp Ser Thr Tyr Thr Gln Leu Trp Asn Trp
                        85                  90                  95

Val Pro Glu Cys Leu Ser Cys Gly Ser Arg Cys Ser Ser Asp Gln Val
                        100                 105                 110

Glu Thr Gln Ala Cys Thr Arg Glu Gln Asn Arg Ile Cys Thr Cys Arg
                        115                 120                 125

Pro Gly Trp Tyr Cys Ala Leu Ser Lys Gln Glu Gly Cys Arg Leu Cys
                        130                 135                 140

Ala Pro Leu Arg Lys Cys Arg Pro Gly Phe Gly Val Ala Arg Pro Gly
        145                 150                 155                 160

Thr Glu Thr Ser Asp Val Val Cys Lys Pro Cys Ala Pro Gly Thr Phe
                        165                 170                 175

Ser Asn Thr Thr Ser Ser Thr Asp Ile Cys Arg Pro His Gln Ile Cys
                        180                 185                 190

Asn Val Val Ala Ile Pro Gly Asn Ala Ser Met Asp Ala Val Cys Thr
                        195                 200                 205

Ser Thr Ser Pro Thr Arg Ser Met Ala Pro Gly Ala Val His Leu Pro
                        210                 215                 220

Gln Pro Val Ser Thr Arg Ser Gln His Thr Gln Pro Thr Pro Glu Pro
        225                 230                 235                 240

Ser Thr Ala Pro Ser Thr Ser Phe Leu Leu Pro Met Gly Pro Ser Pro
                        245                 250                 255

Pro Ala Glu Gly Ser Thr Gly Asp Ala Ala Glu Pro Lys Ser Gly
                        260                 265                 270

Asp Lys Thr His Thr Cys Pro Pro Cys Pro Ala Pro Glu Leu Leu Gly
                        275                 280                 285

Gly Pro Pro Gly Pro Pro Gly Pro Pro Gly Pro Pro Gly Pro Pro Gly
                        290                 295                 300

Pro Pro Gly Glu Lys Gly Glu Lys Gly Asp Pro Gly Pro Lys Gly Asp
        305                 310                 315                 320

Pro Gly Pro Pro Gly Pro Pro Gly Pro Pro Gly Pro Pro Gly Pro Pro
                        325                 330                 335

Gly Pro Pro Gly Gly Thr Gly Pro Ser Val Phe Leu Phe Pro Pro Lys
                        340                 345                 350

Pro Lys Asp Thr Leu Met Ile Ser Arg Thr Pro Glu Val Thr Cys Val
                        355                 360                 365

Val Val Asp Val Ser His Glu Asp Pro Glu Val Lys Phe Asn Trp Tyr
                        370                 375                 380

Val Asp Gly Val Glu Val His Asn Ala Lys Thr Lys Pro Arg Glu Glu
        385                 390                 395                 400

Gln Tyr Asn Ser Thr Tyr Arg Val Val Ser Val Leu Thr Val Leu His
                        405                 410                 415

Gln Asp Trp Leu Asn Gly Lys Glu Tyr Lys Cys Lys Val Ser Asn Lys
                        420                 425                 430

Ala Leu Pro Ala Pro Ile Glu Lys Thr Ile Ser Lys Ala Lys Gly Gln
                        435                 440                 445

Pro Arg Glu Pro Gln Val Tyr Thr Leu Pro Pro Ser Arg Asp Glu Leu
                        450                 455                 460

Thr Lys Asn Gln Val Ser Leu Thr Cys Leu Val Lys Gly Phe Tyr Pro
        465                 470                 475                 480

Ser Asp Ile Ala Val Glu Trp Glu Ser Asn Gly Gln Pro Glu Asn Asn
                        485                 490                 495
```

```
Tyr Lys Thr Thr Pro Pro Val Leu Asp Ser Asp Gly Ser Phe Phe Leu
            500                 505                 510

Tyr Ser Lys Leu Thr Val Asp Lys Ser Arg Trp Gln Gln Gly Asn Val
        515                 520                 525

Phe Ser Cys Ser Val Met His Glu Ala Leu His Asn His Tyr Thr Gln
    530                 535                 540

Lys Ser Leu Ser Leu Ser Pro Gly Lys
545                 550
```

<210> SEQ ID NO 10
<211> LENGTH: 1662
<212> TYPE: DNA
<213> ORGANISM: Artificial Sequence
<220> FEATURE:
<223> OTHER INFORMATION: Synthetic construct

<400> SEQUENCE: 10

```
atggagacag acacactcct gctatgggta ctgctgctct ggttccagg  ttccactggt     60
gacgcggccc agccggccag gcgcgccttg cccgcccagg tggcattta  ccctacgcc    120
ccggagcccg ggagcacatg ccggctcaga gaatactatg accagacagc tcagatgtgc    180
tgcagcaaat gctcgccggg ccaacatgca aaagtcttct gtaccaagac ctcggacacc    240
gtgtgtgact cctgtgagga cagcacatac acccagctct ggaactgggt tcccgagtgc    300
ttgagctgtg gctcccgctg tagctctgac caggtggaaa ctcaagcctg cactcgggaa    360
cagaaccgca tctgcacctg caggcccggc tggtactgcg cgctgagcaa gcaggagggg    420
tgccggctgt gcgcgccgct gcgcaagtgc cgcccgggct cggcgtggc  cagaccagga    480
actgaaacat cagacgtggt gtgcaagccc tgtgccccgg gacgttctc  caacacgact    540
tcatccacgg atatttgcag gccccaccag atctgtaacg tggtggccat ccctgggaat    600
gcaagcatgg atgcagtctg cacgtccacg tccccccaccc ggagtatggc cccaggggca    660
gtacacttac cccagccagt gtccacacga tcccaacaca cgcagccaac tccagaaccc    720
agcactgctc caagcacctc cttcctgctc ccaatgggcc ccagcccccc agctgaaggg    780
agcactggcg acgcggccgc tgagcccaaa tctggtgaca aaactcacac atgcccaccg    840
tgcccagcac ctgaactcct ggagggcca  cctggtcccc caggtcctcc aggaccccca    900
gggccctg  acctccagg  tgagaagggt gagaaaggag atccaggtcc taagggagac    960
cctggtccac caggacctcc tggccctccc gggccgcctg accccccagg ccctcctggt   1020
ggaaccggtc cgtcagtctt cctcttcccc caaaaaccca aggacaccct catgatctcc   1080
cggaccctg  aggtcacatg cgtggtggtg gacgtgagcc acgaagaccc tgaggtcaag   1140
ttcaactggt acgtggacgg cgtggaggtg cataatgcca agacaaagcc gcgggaggag   1200
cagtacaaca gcacgtaccg tgtggtcagc gtcctcaccg tcctgcacca ggactggctg   1260
aatggcaagg agtacaagtg caaggtctcc aacaaagccc tcccagcccc catcgagaaa   1320
accatctcca aagccaaagg gcagccccga gaaccacagg tgtacaccct gcccccatcc   1380
cgggatgagc tgaccaagaa ccaggtcagc ctgacctgcc tggtcaaagg cttctatccc   1440
agcgacatcg ccgtggagtg ggagagcaat gggcagccgg agaacaacta caagaccacg   1500
cctcccgtgc tggactccga cggctccttc ttcctctaca gcaagctcac cgtggacaag   1560
agcaggtggc agcaggggaa cgtcttctca tgctccgtga tgcatgaggc tctgcacaac   1620
cactacacgc agaagagcct ctccctgtct ccgggtaaat ga                      1662
```

<210> SEQ ID NO 11

<211> LENGTH: 553
<212> TYPE: PRT
<213> ORGANISM: Artificial Sequence
<220> FEATURE:
<223> OTHER INFORMATION: Synthetic construct

<400> SEQUENCE: 11

Met Glu Thr Asp Thr Leu Leu Leu Trp Val Leu Leu Leu Trp Val Pro
1               5                   10                  15

Gly Ser Thr Gly Asp Ala Ala Gln Pro Ala Arg Arg Ala Leu Pro Ala
            20                  25                  30

Gln Val Ala Phe Thr Pro Tyr Ala Pro Glu Pro Gly Ser Thr Cys Arg
        35                  40                  45

Leu Arg Glu Tyr Tyr Asp Gln Thr Ala Gln Met Cys Cys Ser Lys Cys
    50                  55                  60

Ser Pro Gly Gln His Ala Lys Val Phe Cys Thr Lys Thr Ser Asp Thr
65                  70                  75                  80

Val Cys Asp Ser Cys Glu Asp Ser Thr Tyr Thr Gln Leu Trp Asn Trp
                85                  90                  95

Val Pro Glu Cys Leu Ser Cys Gly Ser Arg Cys Ser Ser Asp Gln Val
            100                 105                 110

Glu Thr Gln Ala Cys Thr Arg Glu Gln Asn Arg Ile Cys Thr Cys Arg
        115                 120                 125

Pro Gly Trp Tyr Cys Ala Leu Ser Lys Gln Glu Gly Cys Arg Leu Cys
    130                 135                 140

Ala Pro Leu Arg Lys Cys Arg Pro Gly Phe Gly Val Ala Arg Pro Gly
145                 150                 155                 160

Thr Glu Thr Ser Asp Val Val Cys Lys Pro Cys Ala Pro Gly Thr Phe
                165                 170                 175

Ser Asn Thr Thr Ser Ser Thr Asp Ile Cys Arg Pro His Gln Ile Cys
            180                 185                 190

Asn Val Val Ala Ile Pro Gly Asn Ala Ser Met Asp Ala Val Cys Thr
        195                 200                 205

Ser Thr Ser Pro Thr Arg Ser Met Ala Pro Gly Ala Val His Leu Pro
    210                 215                 220

Gln Pro Val Ser Thr Arg Ser Gln His Thr Gln Pro Thr Pro Glu Pro
225                 230                 235                 240

Ser Thr Ala Pro Ser Thr Ser Phe Leu Leu Pro Met Gly Pro Ser Pro
                245                 250                 255

Pro Ala Glu Gly Ser Thr Gly Asp Ala Ala Ala Glu Pro Lys Ser Gly
            260                 265                 270

Asp Lys Thr His Thr Cys Pro Pro Cys Pro Ala Pro Glu Leu Leu Gly
        275                 280                 285

Gly Pro Pro Gly Pro Pro Gly Pro Pro Gly Pro Pro Gly Pro Pro Gly
    290                 295                 300

Pro Pro Gly Glu Lys Gly Glu Lys Gly Asp Pro Gly Pro Lys Gly Asp
305                 310                 315                 320

Pro Gly Pro Pro Gly Pro Pro Gly Pro Pro Gly Pro Pro Gly Pro Pro
                325                 330                 335

Gly Pro Pro Gly Gly Thr Gly Pro Ser Val Phe Leu Phe Pro Pro Lys
            340                 345                 350

Pro Lys Asp Thr Leu Met Ile Ser Arg Thr Pro Glu Val Thr Cys Val
        355                 360                 365

Val Val Asp Val Ser His Glu Asp Pro Glu Val Lys Phe Asn Trp Tyr
    370                 375                 380

```
Val Asp Gly Val Glu Val His Asn Ala Lys Thr Lys Pro Arg Glu Glu
385                 390                 395                 400

Gln Tyr Asn Ser Thr Tyr Arg Val Val Ser Val Leu Thr Val Leu His
            405                 410                 415

Gln Asp Trp Leu Asn Gly Lys Glu Tyr Lys Cys Lys Val Ser Asn Lys
        420                 425                 430

Ala Leu Pro Ala Pro Ile Glu Lys Thr Ile Ser Lys Ala Lys Gly Gln
    435                 440                 445

Pro Arg Glu Pro Gln Val Tyr Thr Leu Pro Pro Ser Arg Asp Glu Leu
450                 455                 460

Thr Lys Asn Gln Val Ser Leu Ser Cys Ala Val Lys Gly Phe Tyr Pro
465                 470                 475                 480

Ser Asp Ile Ala Val Glu Trp Glu Ser Asn Gly Gln Pro Glu Asn Asn
            485                 490                 495

Tyr Lys Thr Thr Pro Pro Val Leu Asp Ser Asp Gly Ser Phe Phe Leu
        500                 505                 510

Val Ser Lys Leu Thr Val Asp Lys Ser Arg Trp Gln Gln Gly Asn Val
    515                 520                 525

Phe Ser Cys Ser Val Met His Glu Ala Leu His Asn His Tyr Thr Gln
530                 535                 540

Lys Ser Leu Ser Leu Ser Pro Gly Lys
545                 550

<210> SEQ ID NO 12
<211> LENGTH: 1662
<212> TYPE: DNA
<213> ORGANISM: Artificial Sequence
<220> FEATURE:
<223> OTHER INFORMATION: Synthetic construct

<400> SEQUENCE: 12
atggagacag acacactcct gctatgggta ctgctgctct ggttccagg ttccactggt      60 gacgcggccc agccggccag gcgcgccttg cccgcccagg tggcatttac accctacgcc     120
ccggagcccg ggagcacatg ccggctcaga gaatactatg accagacagc tcagatgtgc     180
tgcagcaaat gctcgccggg ccaacatgca aaagtcttct gtaccaagac tcggacacc      240 gtgtgtgact cctgtgagga cagcacatac acccagctct ggaactgggt tcccgagtgc     300
ttgagctgtg gctcccgctg tagctctgac caggtggaaa ctcaagcctg cactcgggaa     360
cagaaccgca tctgcacctg caggcccggc tggtactgcg cgctgagcaa gcaggagggg     420
tgccggctgt gcgcgccgct gcgcaagtgc cgcccgggct tcggcgtggc cagaccagga     480
actgaaacat cagacgtggt gtgcaagccc tgtgccccgg gacgttctc caacacgact      540 tcatccacgg atatttgcag gccccaccag atctgtaacg tggtggccat ccctgggaat     600
gcaagcatgg atgcagtctg cacgtccacg tcccccaccc ggagtatggc cccaggggca     660
gtacacttac cccagccagt gtccacacga tcccaacaca cgcagccaac tccagaaccc     720
agcactgctc caagcacctc cttcctgctc caatgggcc ccagcccccc agctgaaggg     780
agcactggcg acgcggccgc tgagcccaaa tctggtgaca aaactcacac atgcccaccg     840
tgcccagcac ctgaactcct ggagggcca cctggtcccc caggtcctcc aggacccca      900 gggcccctg acctccagg tgagaagggt gagaaggag atccaggtcc taaggagac        960 cctggtccac caggacctcc tggccctccc gggccgcctg accccccagg ccctcctggt     1020
ggaaccggtc gtcagtctt cctcttcccc ccaaaaccca aggacacct catgatctcc      1080 cggacccctg aggtcacatg cgtggtggtg gacgtgagcc acgaagaccc tgaggtcaag     1140
```

```
ttcaactggt acgtggacgg cgtggaggtg cataatgcca agacaaagcc gcgggaggag    1200
cagtacaaca gcacgtaccg tgtggtcagc gtcctcaccg tcctgcacca ggactggctg    1260
aatggcaagg agtacaagtg caaggtctcc aacaaagccc tcccagcccc catcgagaaa    1320
accatctcca agccaaagg gcagccccga gaaccacagg tgtacaccct gcccccatcc    1380
cgggatgagc tgaccaagaa ccaggtcagc ctgtcctgcg cggtcaaagg cttctatccc    1440
agcgacatcg ccgtggagtg ggagagcaat gggcagccgg agaacaacta caagaccacg    1500
cctcccgtgc tggactccga cggctccttc ttcctcgtca gcaagctcac cgtggacaag    1560
agcaggtggc agcaggggaa cgtcttctca tgctccgtga tgcatgaggc tctgcacaac    1620
cactacacgc agaagagcct ctccctgtct ccgggtaaat ga                      1662
```

<210> SEQ ID NO 13
<211> LENGTH: 447
<212> TYPE: PRT
<213> ORGANISM: Artificial Sequence
<220> FEATURE:
<223> OTHER INFORMATION: Synthetic construct

<400> SEQUENCE: 13

```
Met Glu Thr Asp Thr Leu Leu Leu Trp Val Leu Leu Trp Val Pro
1               5                   10                  15

Gly Ser Thr Gly Asp Ala Ala Gln Pro Ala Arg Arg Ala Gln Val Gln
            20                  25                  30

Leu Leu Glu Ser Gly Gly Gly Leu Val Gln Pro Gly Gly Ser Leu Arg
        35                  40                  45

Leu Ser Cys Ala Ala Ser Gly Val Ser Ile Thr Ala Glu Ser Met Ser
    50                  55                  60

Trp Val Arg Gln Ala Pro Gly Lys Gly Leu Glu Trp Val Ser Thr Ile
65                  70                  75                  80

Thr Met Arg Asp Gly Ser Thr Tyr Tyr Ala Asp Ser Val Lys Gly Arg
                85                  90                  95

Phe Thr Ile Ser Arg Asp Asn Ser Lys Asn Thr Leu Tyr Leu Gln Met
            100                 105                 110

Asn Ser Leu Arg Ala Glu Asp Thr Ala Val Tyr Tyr Cys Ala Arg Ala
        115                 120                 125

Arg Ala Met Tyr Pro Leu Arg Ser Ser Gln Leu Glu Ser Trp Gly Gln
    130                 135                 140

Gly Thr Leu Val Thr Val Ser Ser Ala Ala Gly Gly Gly Gly Ser
145                 150                 155                 160

Gly Pro Pro Gly Pro Pro Gly Pro Pro Gly Pro Pro Gly Pro Pro Gly
                165                 170                 175

Pro Pro Gly Glu Lys Gly Glu Lys Gly Asp Pro Gly Pro Lys Gly Asp
            180                 185                 190

Pro Gly Pro Pro Gly Pro Pro Gly Pro Pro Gly Pro Pro Gly Pro Pro
        195                 200                 205

Gly Pro Pro Gly Gly Thr Gly Glu Pro Lys Ser Gly Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270
```

```
Val Lys Phe Asn Trp Tyr Val Asp Gly Val Glu Val His Asn Ala Lys
    275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly Lys
        435                 440                 445

<210> SEQ ID NO 14
<211> LENGTH: 1344
<212> TYPE: DNA
<213> ORGANISM: Artificial Sequence
<220> FEATURE:
<223> OTHER INFORMATION: Synthetic construct

<400> SEQUENCE: 14
atggagacag acacactcct gctatgggta ctgctgctct ggttccagg ttccactggt      60 gacgcggccc agccggccag gcgcgcccag gtgcagctgt tggagtctgg gggaggcttg    120
gtacagcctg gggggtccct gcgtctctcc tgtgcagcct ccggagttag cattaccgct    180
gagtctatga gctgggtccg ccaggctcca gggaagggtc tagagtgggt atcaaccatt    240
acgatgcgag acgtagcac atactacgca gactccgtga agggccggtt caccatctcc    300
cgtgacaatt ccaagaacac gctgtatctg caaatgaaca gcctgcgtgc cgaggacacc    360
gcggtatatt attgcgcgag agctagggct atgtatcctt gcgttcgtc gcagttggag    420 tcttggggtc agggaaccct ggtcaccgtc tcgagcgcgg ccgctggtgg aggcggttca    480
gggccacctg gtcccccagg tcctccagga cccccagggc ccctggacc tccaggtgag    540 aagggtgaga aggagatcc aggtcctaag ggagaccctg gtccaccagg acctcctggc    600 cctcccggc cgcctggacc cccaggccct cctggtggaa ccggtgagcc caaatctggt    660
gacaaaactc acacatgccc accgtgccca gcacctgaac tcctgggggg accgtcagtc    720
ttcctcttcc ccccaaaacc caaggacacc ctcatgatct cccggacccc tgaggtcaca    780
tgcgtggtgg tggacgtgag ccacgaagac cctgaggtca agttcaactg gtacgtggac    840
ggcgtggagg tgcataatgc caagacaaag ccgcgggagg agcagtacaa cagcacgtac    900
cgtgtggtca gcgtcctcac cgtcctgcac caggactggc tgaatggcaa ggagtacaag    960
tgcaaggtct ccaacaaagc cctcccagcc ccatcgaga aaccatctc caaagccaaa    1020 gggcagcccc gagaaccaca ggtgtacacc ctgcccccat cccgggatga gctgaccaag    1080
aaccaggtca gcctgacctg cctggtcaaa ggcttctatc ccagcgacat cgccgtggag    1140
```

```
tgggagagca atgggcagcc ggagaacaac tacaagacca cgcctcccgt gctggactcc    1200
gacggctcct tcttcctcta cagcaagctc accgtggaca agagcaggtg gcagcagggg    1260
aacgtcttct catgctccgt gatgcatgag gctctgcaca accactacac gcagaagagc    1320
ctctccctgt ctccgggtaa atga                                            1344
```

<210> SEQ ID NO 15
<211> LENGTH: 20
<212> TYPE: PRT
<213> ORGANISM: Artificial Sequence
<220> FEATURE:
<223> OTHER INFORMATION: Synthetic Signal Sequence

<400> SEQUENCE: 15

Met Glu Thr Asp Thr Leu Leu Leu Trp Val Leu Leu Leu Trp Val Pro
1               5                   10                  15

Gly Ser Thr Gly
            20

<210> SEQ ID NO 16
<211> LENGTH: 247
<212> TYPE: PRT
<213> ORGANISM: Artificial Sequence
<220> FEATURE:
<223> OTHER INFORMATION: Synthetic TNF_RII EC Domain

<400> SEQUENCE: 16

Asp Ala Ala Gln Pro Ala Arg Arg Ala Leu Pro Ala Gln Val Ala Phe
1               5                   10                  15

Thr Pro Tyr Ala Pro Glu Pro Gly Ser Thr Cys Arg Leu Arg Glu Tyr
            20                  25                  30

Tyr Asp Gln Thr Ala Gln Met Cys Cys Ser Lys Cys Ser Pro Gly Gln
        35                  40                  45

His Ala Lys Val Phe Cys Thr Lys Thr Ser Asp Thr Val Cys Asp Ser
    50                  55                  60

Cys Glu Asp Ser Thr Tyr Thr Gln Leu Trp Asn Trp Val Pro Glu Cys
65                  70                  75                  80

Leu Ser Cys Gly Ser Arg Cys Ser Ser Asp Gln Val Glu Thr Gln Ala
                85                  90                  95

Cys Thr Arg Glu Gln Asn Arg Ile Cys Thr Cys Arg Pro Gly Trp Tyr
            100                 105                 110

Cys Ala Leu Ser Lys Gln Glu Gly Cys Arg Leu Cys Ala Pro Leu Arg
        115                 120                 125

Lys Cys Arg Pro Gly Phe Gly Val Ala Arg Pro Gly Thr Glu Thr Ser
    130                 135                 140

Asp Val Val Cys Lys Pro Cys Ala Pro Gly Thr Phe Ser Asn Thr Thr
145                 150                 155                 160

Ser Ser Thr Asp Ile Cys Arg Pro His Gln Ile Cys Asn Val Val Ala
                165                 170                 175

Ile Pro Gly Asn Ala Ser Met Asp Ala Val Cys Thr Ser Thr Ser Pro
            180                 185                 190

Thr Arg Ser Met Ala Pro Gly Ala Val His Leu Pro Gln Pro Val Ser
        195                 200                 205

Thr Arg Ser Gln His Thr Gln Pro Thr Pro Glu Pro Ser Thr Ala Pro
    210                 215                 220

Ser Thr Ser Phe Leu Leu Pro Met Gly Pro Ser Pro Pro Ala Glu Gly
225                 230                 235                 240

```
Ser Thr Gly Asp Ala Ala Ala
            245

<210> SEQ ID NO 17
<211> LENGTH: 132
<212> TYPE: PRT
<213> ORGANISM: Artificial Sequence
<220> FEATURE:
<223> OTHER INFORMATION: Synthetic VH domain of anti-beta-galactosidase

<400> SEQUENCE: 17

Asp Ala Ala Gln Pro Ala Arg Arg Ala Gln Val Gln Leu Leu Glu Ser
1               5                   10                  15

Gly Gly Gly Leu Val Gln Pro Gly Gly Ser Leu Arg Leu Ser Cys Ala
            20                  25                  30

Ala Ser Gly Val Ser Ile Thr Ala Glu Ser Met Ser Trp Val Arg Gln
        35                  40                  45

Ala Pro Gly Lys Gly Leu Glu Trp Val Ser Thr Ile Thr Met Arg Asp
    50                  55                  60

Gly Ser Thr Tyr Tyr Ala Asp Ser Val Lys Gly Arg Phe Thr Ile Ser
65                  70                  75                  80

Arg Asp Asn Ser Lys Asn Thr Leu Tyr Leu Gln Met Asn Ser Leu Arg
                85                  90                  95

Ala Glu Asp Thr Ala Val Tyr Tyr Cys Ala Arg Ala Arg Ala Met Tyr
            100                 105                 110

Pro Leu Arg Ser Ser Gln Leu Glu Ser Trp Gly Gln Gly Thr Leu Val
        115                 120                 125

Thr Val Ser Ser
    130

<210> SEQ ID NO 18
<211> LENGTH: 8
<212> TYPE: PRT
<213> ORGANISM: Artificial Sequence
<220> FEATURE:
<223> OTHER INFORMATION: Synthetic Linker

<400> SEQUENCE: 18

Ala Ala Ala Gly Gly Gly Gly Ser
1               5

<210> SEQ ID NO 19
<211> LENGTH: 15
<212> TYPE: PRT
<213> ORGANISM: Artificial Sequence
<220> FEATURE:
<223> OTHER INFORMATION: Synthetic Hinge Region Version 1

<400> SEQUENCE: 19

Glu Pro Lys Ser Gly Asp Lys Thr His Thr Cys Pro Pro Cys Pro
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: Synthetic Hinge Region Version 2

<400> SEQUENCE: 20

Glu Pro Lys Ser Cys Asp Lys Thr His Thr Cys Pro Pro Cys Pro
1               5                   10                  15
```

```
<210> SEQ ID NO 21
<211> LENGTH: 30
<212> TYPE: PRT
<213> ORGANISM: Artificial Sequence
<220> FEATURE:
<223> OTHER INFORMATION: Synthetic Collagen-like domain Version 1

<400> SEQUENCE: 21

Gly Pro Pro Gly Pro Pro Gly Pro Pro Gly Pro Pro Gly Pro Pro Gly
1               5                   10                  15

Pro Pro Gly Pro Pro Gly Pro Pro Gly Pro Pro Gly Pro Pro
            20                  25                  30

<210> SEQ ID NO 22
<211> LENGTH: 51
<212> TYPE: PRT
<213> ORGANISM: Artificial Sequence
<220> FEATURE:
<223> OTHER INFORMATION: Synthetic Collagen-like domain Version 2

<400> SEQUENCE: 22

Gly Pro Pro Gly Pro Pro Gly Pro Pro Gly Pro Pro Gly Pro Pro Gly
1               5                   10                  15

Pro Pro Gly Glu Lys Gly Glu Lys Gly Asp Pro Gly Pro Lys Gly Asp
            20                  25                  30

Pro Gly Pro Pro Gly Pro Pro Gly Pro Pro Gly Pro Pro Gly Pro Pro
        35                  40                  45

Gly Pro Pro
    50

<210> SEQ ID NO 23
<211> LENGTH: 39
<212> TYPE: PRT
<213> ORGANISM: Artificial Sequence
<220> FEATURE:
<223> OTHER INFORMATION: Synthetic Collagen-like domain Version 3

<400> SEQUENCE: 23

Gly Pro Pro Gly Pro Pro Gly Pro Pro Gly Pro Pro Gly Glu Lys Gly
1               5                   10                  15

Glu Lys Gly Asp Pro Gly Pro Lys Gly Asp Ile Gly Pro Pro Gly Pro
            20                  25                  30

Pro Gly Pro Pro Gly Pro Pro
        35

<210> SEQ ID NO 24
<211> LENGTH: 42
<212> TYPE: PRT
<213> ORGANISM: Artificial Sequence
<220> FEATURE:
<223> OTHER INFORMATION: Synthetic Collagen-like domain Version 4

<400> SEQUENCE: 24

Gly Pro Pro Gly Pro Pro Gly Pro Pro Gly Pro Pro Gly Pro Pro Gly
1               5                   10                  15

Glu Lys Gly Glu Lys Gly Asp Pro Gly Pro Lys Gly Asp Ile Gly Pro
            20                  25                  30

Pro Gly Pro Pro Gly Pro Pro Gly Pro Pro
        35                  40

<210> SEQ ID NO 25
<211> LENGTH: 121
<212> TYPE: PRT
<213> ORGANISM: Artificial Sequence
```

```
<220> FEATURE:
<223> OTHER INFORMATION: Synthetic Collagen-like domain Version 8

<400> SEQUENCE: 25

Gly Pro Pro Gly Pro Pro Gly Pro Pro Gly Pro Pro Gly Thr Lys Gly
1               5                   10                  15

Glu Lys Gly Glu Pro Gly Gln Gly Leu Arg Gly Leu Gln Gly Pro Gln
            20                  25                  30

Gly Glu Lys Gly Asp Arg Gly Leu Thr Gly Gln Thr Gly Pro Pro Gly
        35                  40                  45

Ala Pro Gly Ile Arg Gly Ile Pro Gly Val Lys Gly Asp Arg Gly Gln
    50                  55                  60

Ile Gly Phe Pro Gly Gly Arg Gly Asn Pro Gly Ala Pro Gly Lys Pro
65                  70                  75                  80

Gly Arg Ser Gly Ser Pro Gly Pro Lys Gly Gln Lys Gly Glu Lys Gly
                85                  90                  95

Ser Val Gly Pro Pro Gly Pro Pro Gly Pro Pro Gly Pro Pro Gly Pro
            100                 105                 110

Pro Gly Pro Cys Cys Gly Gly Thr Gly
        115                 120

<210> SEQ ID NO 26
<211> LENGTH: 8
<212> TYPE: PRT
<213> ORGANISM: Artificial Sequence
<220> FEATURE:
<223> OTHER INFORMATION: Synthetic Disulfide knot of type XXI Collagen

<400> SEQUENCE: 26

Gly Ile Cys Asp Pro Ser Leu Cys
1               5

<210> SEQ ID NO 27
<211> LENGTH: 210
<212> TYPE: PRT
<213> ORGANISM: Homo sapiens
<220> FEATURE:
<221> NAME/KEY: misc_feature
<223> OTHER INFORMATION: CH2 and CH3 domains of human IgG1 Version 1

<400> SEQUENCE: 27

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
            100                 105                 110

Thr Leu Pro Pro Ser Arg Asp Glu Leu Thr Lys Asn Gln Val Ser Leu
        115                 120                 125

Thr Cys Leu Val Lys Gly Phe Tyr Pro Ser Asp Ile Ala Val Glu Trp
    130                 135                 140
```

```
Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210

<210> SEQ ID NO 28
<211> LENGTH: 210
<212> TYPE: PRT
<213> ORGANISM: Homo sapiens
<220> FEATURE:
<221> NAME/KEY: misc_feature
<223> OTHER INFORMATION: CH2 and CH3 domains of human IgG1 Version 2

<400> SEQUENCE: 28

Pro Ser Val Phe Leu Phe Pro Pro Lys Pro Lys Asp Thr Leu Met Ile
1               5                   10                  15

Ser Arg Thr Pro Glu Val Thr Cys Val Val Val Asp Val Ser His Glu
            20                  25                  30

Asp Pro Glu Val Lys Phe Asn Trp Tyr Val Asp Gly Val Glu Val His
        35                  40                  45

Asn Ala Lys Thr Lys Pro Arg Glu Glu Gln Tyr Asn Ser Thr Tyr Arg
    50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
            100                 105                 110

Thr Leu Pro Pro Ser Arg Asp Glu Leu Thr Lys Asn Gln Val Ser Leu
        115                 120                 125

Thr Cys Leu Val Lys Gly Phe Tyr Pro Ser Asp Ile Ala Val Glu Trp
    130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210

<210> SEQ ID NO 29
<211> LENGTH: 210
<212> TYPE: PRT
<213> ORGANISM: Homo sapiens
<220> FEATURE:
<221> NAME/KEY: misc_feature
<223> OTHER INFORMATION: CH2 and CH3 domains of human IgG1 Version 3

<400> SEQUENCE: 29

Pro Ser Val Phe Leu Phe Pro Pro Lys Pro Lys Asp Thr Leu Met Ile
```

```
  1               5                  10                 15
Ser Arg Thr Pro Glu Val Thr Cys Val Val Asp Val Ser His Glu
                20                  25                 30

Asp Pro Glu Val Lys Phe Asn Trp Tyr Val Asp Gly Val Glu Val His
                35                  40                 45

Asn Ala Lys Thr Lys Pro Arg Glu Glu Gln Tyr Asn Ser Thr Tyr Arg
 50                 55                 60

Val Val Ser Val Leu Thr Val Leu His Gln Asp Trp Leu Asn Gly Lys
 65                  70                 75                  80

Glu Tyr Lys Cys Lys Val Ser Asn Lys Ala Leu Pro Ala Pro Ile Glu
                85                  90                 95

Lys Thr Ile Ser Lys Ala Lys Gly Gln Pro Arg Glu Pro Gln Val Tyr
                100                 105                110

Thr Leu Pro Pro Ser Arg Asp Glu Leu Thr Lys Asn Gln Val Ser Leu
                115                 120                125

Thr Cys Leu Val Lys Gly Phe Tyr Pro Ser Asp Ile Ala Val Glu Trp
                130                 135                140

Glu Ser Asn Gly Gln Pro Glu Asn Asn Tyr Lys Thr Thr Pro Pro Val
145                 150                 155                160

Leu Asp Ser Asp Gly Ser Phe Phe Leu Tyr Ser Lys Leu Thr Val Asp
                165                 170                175

Lys Ser Arg Trp Gln Gln Gly Asn Val Phe Ser Cys Ser Val Met His
                180                 185                190

Glu Ala Leu His Asn His Tyr Thr Gln Lys Ser Leu Ser Leu Ser Pro
                195                 200                205

Gly Lys
    210

<210> SEQ ID NO 30
<211> LENGTH: 210
<212> TYPE: PRT
<213> ORGANISM: Homo sapiens
<220> FEATURE:
<221> NAME/KEY: misc_feature
<223> OTHER INFORMATION: CH2 and CH3 domains of human IgG1 Version 4

<400> SEQUENCE: 30

Pro Ser Val Phe Leu Phe Pro Pro Lys Pro Lys Asp Thr Leu Met Ile
1                5                  10                 15

Ser Arg Thr Pro Glu Val Thr Cys Val Val Asp Val Ser His Glu
                20                  25                 30

Asp Pro Glu Val Lys Phe Asn Trp Tyr Val Asp Gly Val Glu Val His
                35                  40                 45

Asn Ala Lys Thr Lys Pro Arg Glu Glu Gln Tyr Asn Ser Thr Tyr Arg
 50                 55                 60

Val Val Ser Val Leu Thr Val Leu His Gln Asp Trp Leu Asn Gly Lys
 65                  70                 75                  80

Glu Tyr Lys Cys Lys Val Ser Asn Lys Ala Leu Pro Ala Pro Ile Glu
                85                  90                 95

Lys Thr Ile Ser Lys Ala Lys Gly Gln Pro Arg Glu Pro Gln Val Tyr
                100                 105                110

Thr Leu Pro Pro Ser Arg Asp Glu Leu Thr Lys Asn Gln Val Ser Leu
                115                 120                125

Thr Cys Leu Val Lys Gly Phe Tyr Pro Ser Asp Ile Ala Val Glu Trp
                130                 135                140

Glu Ser Asn Gly Gln Pro Glu Asn Asn Tyr Lys Thr Thr Pro Pro Val
```

```
145                 150                 155                 160
Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
                180                 185                 190

Glu Ala Leu His Asn His Tyr Thr Gln Lys Ser Leu Ser Leu Ser Pro
                195                 200                 205

Gly Lys
    210

<210> SEQ ID NO 31
<211> LENGTH: 210
<212> TYPE: PRT
<213> ORGANISM: Homo sapiens
<220> FEATURE:
<221> NAME/KEY: misc_feature
<223> OTHER INFORMATION: CH2 and CH3 domains of human IgG1 Version 5

<400> SEQUENCE: 31

Pro Ser Val Phe Leu Phe Pro Pro Lys Pro Lys Asp Thr Leu Met Ile
1               5                   10                  15

Ser Arg Thr Pro Glu Val Thr Cys Val Val Asp Val Ser His Glu
                20                  25                  30

Asp Pro Glu Val Lys Phe Asn Trp Tyr Val Asp Gly Val Glu Val His
                35                  40                  45

Asn Ala Lys Thr Lys Pro Arg Glu Glu Gln Tyr Asn Ser Thr Tyr Arg
50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
                100                 105                 110

Thr Leu Pro Pro Ser Arg Asp Glu Leu Thr Lys Asn Gln Val Ser Leu
                115                 120                 125

Thr Cys Leu Val Lys Gly Phe Tyr Pro Ser Asp Ile Ala Val Glu Trp
                130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Tyr Ser Lys Leu Thr Val Asp
                165                 170                 175

Lys Ser Arg Trp Gln Gln Gly Asn Val Phe Ser Cys Ser Val Met His
                180                 185                 190

Glu Ala Leu His Asn His Tyr Thr Gln Lys Ser Leu Ser Leu Ser Pro
                195                 200                 205

Gly Lys
    210

<210> SEQ ID NO 32
<211> LENGTH: 210
<212> TYPE: PRT
<213> ORGANISM: Homo sapiens
<220> FEATURE:
<221> NAME/KEY: misc_feature
<223> OTHER INFORMATION: Mutated CH2 and CH3 Version 1

<400> SEQUENCE: 32

Pro Ser Val Phe Leu Phe Pro Pro Lys Pro Lys Asp Thr Leu Met Ile
1               5                   10                  15
```

```
Ser Arg Thr Pro Glu Val Thr Cys Val Val Asp Val Ser His Glu
        20                  25                  30

Asp Pro Glu Val Lys Phe Asn Trp Tyr Val Asp Gly Val Glu Val His
            35                  40                  45

Asn Ala Lys Thr Lys Pro Arg Glu Glu Gln Tyr Asn Ser Thr Tyr Arg
        50                  55                  60

Val Val Ser Val Leu Thr Val Leu His Gln Asp Trp Leu Asn Gly Lys
65                  70                  75                  80

Glu Tyr Lys Cys Lys Val Ser Asn Lys Ala Leu Pro Ala Pro Ile Glu
                85                  90                  95

Lys Thr Ile Ser Lys Ala Lys Gly Gln Pro Arg Glu Pro Gln Val Tyr
            100                 105                 110

Thr Leu Pro Pro Ser Arg Asp Glu Leu Thr Lys Asn Gln Val Ser Leu
        115                 120                 125

Ser Cys Ala Val Lys Gly Phe Tyr Pro Ser Asp Ile Ala Val Glu Trp
130                 135                 140

Glu Ser Asn Gly Gln Pro Glu Asn Asn Tyr Lys Thr Thr Pro Pro Val
145                 150                 155                 160

Leu Asp Ser Asp Gly Ser Phe Phe Leu Val Ser Lys Leu Thr Val Asp
                165                 170                 175

Lys Ser Arg Trp Gln Gln Gly Asn Val Phe Ser Cys Ser Val Met His
            180                 185                 190

Glu Ala Leu His Asn His Tyr Thr Gln Lys Ser Leu Ser Leu Ser Pro
        195                 200                 205

Gly Lys
    210

<210> SEQ ID NO 33
<211> LENGTH: 30
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(30)
<223> OTHER INFORMATION: Each Xaa is Hyp

<400> SEQUENCE: 33

Gly Pro Xaa Gly Pro Xaa Gly Pro Xaa Gly Pro Xaa Gly Pro Xaa Gly
1               5                   10                  15

Pro Xaa Gly Pro Xaa Gly Pro Xaa Gly Pro Xaa Gly Pro Xaa
            20                  25                  30

<210> SEQ ID NO 34
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa may be Glu, Phe, Gln, Pro, Arg, Thr or Val
<220> FEATURE:
<221> NAME/KEY: misc_feature
<222> LOCATION: (6)..(6)
<223> OTHER INFORMATION: Asp may or may not be present

<400> SEQUENCE: 34

Gly Xaa Lys Gly Glu Asp
1               5
```

<210> SEQ ID NO 35
<211> LENGTH: 51
<212> TYPE: PRT
<213> ORGANISM: Artificial Sequence
<220> FEATURE:
<223> OTHER INFORMATION: Synthetic peptide

<400> SEQUENCE: 35

Gly Pro Pro Gly Pro Pro Gly Pro Pro Gly Pro Pro Gly Pro Pro Gly
1               5                   10                  15

Pro Pro Gly Glu Lys Gly Glu Lys Gly Asp Pro Gly Pro Lys Gly Asp
            20                  25                  30

Ile Gly Pro Pro Gly Pro Pro Gly Pro Pro Gly Pro Pro Gly Pro Pro
        35                  40                  45

Gly Pro Pro
    50

<210> SEQ ID NO 36
<211> LENGTH: 63
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (4)..(18)
<223> OTHER INFORMATION: Any "Gly-Pro-Pro" maybe present or absent
<220> FEATURE:
<221> NAME/KEY: misc_feature
<222> LOCATION: (46)..(63)
<223> OTHER INFORMATION: Any "Gly-Pro-Pro" maybe present or absent

<400> SEQUENCE: 36

Gly Pro Pro Gly Pro Pro Gly Pro Pro Gly Pro Pro Gly Pro Pro Gly
1               5                   10                  15

Pro Pro Gly Glu Lys Gly Glu Lys Gly Asp Pro Gly Pro Lys Gly Asp
            20                  25                  30

Pro Gly Pro Pro Gly Pro Pro Gly Pro Pro Gly Pro Pro Gly Pro Pro
        35                  40                  45

Gly Pro Pro Gly Pro Pro Gly Pro Pro Gly Pro Pro Gly Pro Pro
    50                  55                  60

<210> SEQ ID NO 37
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Gly-Pro-Pro may repeat indefinitely

<400> SEQUENCE: 37

Gly Pro Pro Gly Ile Cys Asp Pro Ser Leu Cys Thr Gly
1               5                   10

<210> SEQ ID NO 38
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)

```
<223> OTHER INFORMATION: Gly-Pro-Pro may repeat indefinitely
<220> FEATURE:
<221> NAME/KEY: misc_feature
<222> LOCATION: (19)..(21)
<223> OTHER INFORMATION: Gly-Pro-Pro may repeat indefinitely

<400> SEQUENCE: 38

Gly Pro Pro Gly Glu Lys Gly Glu Lys Gly Asp Pro Gly Pro Lys Gly
1               5                   10                  15

Asp Pro Gly Pro Pro Gly Gly Thr Gly
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Gly-Pro-Pro may repeat indefinitely
<220> FEATURE:
<221> NAME/KEY: misc_feature
<222> LOCATION: (19)..(21)
<223> OTHER INFORMATION: Gly-Pro-Pro may repeat indefinitely

<400> SEQUENCE: 39

Gly Pro Pro Gly Glu Lys Gly Glu Lys Gly Asp Pro Gly Pro Lys Gly
1               5                   10                  15

Asp Ile Gly Pro Pro Gly Gly Thr Gly
            20                  25

<210> SEQ ID NO 40
<211> LENGTH: 5
<212> TYPE: PRT
<213> ORGANISM: Artificial Sequence
<220> FEATURE:
<223> OTHER INFORMATION: Synthetic peptide

<400> SEQUENCE: 40

Gly Glu Lys Gly Glu
1               5

<210> SEQ ID NO 41
<211> LENGTH: 5
<212> TYPE: PRT
<213> ORGANISM: Artificial Sequence
<220> FEATURE:
<223> OTHER INFORMATION: Synthetic peptide

<400> SEQUENCE: 41

Gly Glu Lys Gly Asp
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic peptide

<400> SEQUENCE: 42

Gly Pro Lys Gly Asp
1               5

<210> SEQ ID NO 43
<211> LENGTH: 5
```

```
<212> TYPE: PRT
<213> ORGANISM: Artificial Sequence
<220> FEATURE:
<223> OTHER INFORMATION: Synthetic peptide

<400> SEQUENCE: 43

Gly Thr Lys Gly Glu
1               5

<210> SEQ ID NO 44
<211> LENGTH: 5
<212> TYPE: PRT
<213> ORGANISM: Artificial Sequence
<220> FEATURE:
<223> OTHER INFORMATION: Synthetic peptide

<400> SEQUENCE: 44

Gly Val Lys Gly Asp
1               5

<210> SEQ ID NO 45
<211> LENGTH: 5
<212> TYPE: PRT
<213> ORGANISM: Artificial Sequence
<220> FEATURE:
<223> OTHER INFORMATION: Synthetic peptide

<400> SEQUENCE: 45

Gly Gln Lys Gly Glu
1               5

<210> SEQ ID NO 46
<211> LENGTH: 23
<212> TYPE: PRT
<213> ORGANISM: Homo sapiens
<220> FEATURE:
<221> NAME/KEY: misc_feature
<223> OTHER INFORMATION: Human IgG1

<400> SEQUENCE: 46

Glu Pro Lys Ser Cys Asp Lys Thr His Thr Cys Pro Pro Cys Pro Ala
1               5                   10                  15

Pro Glu Leu Leu Gly Gly Pro
            20

<210> SEQ ID NO 47
<211> LENGTH: 19
<212> TYPE: PRT
<213> ORGANISM: Homo sapiens
<220> FEATURE:
<221> NAME/KEY: misc_feature
<223> OTHER INFORMATION: Human IgG2

<400> SEQUENCE: 47

Glu Arg Lys Cys Cys Val Glu Cys Pro Pro Cys Pro Ala Pro Pro Val
1               5                   10                  15

Ala Gly Pro

<210> SEQ ID NO 48
<211> LENGTH: 25
<212> TYPE: PRT
<213> ORGANISM: Homo sapiens
<220> FEATURE:
<221> NAME/KEY: misc_feature
<223> OTHER INFORMATION: Human IgG3

<400> SEQUENCE: 48
```

```
Glu Leu Lys Thr Pro Leu Gly Asp Thr Thr His Thr Cys Pro Arg Cys
1               5                   10                  15

Pro Ala Pro Glu Leu Leu Gly Gly Pro
            20                  25

<210> SEQ ID NO 49
<211> LENGTH: 20
<212> TYPE: PRT
<213> ORGANISM: Homo sapiens
<220> FEATURE:
<221> NAME/KEY: misc_feature
<223> OTHER INFORMATION: Human IgG4

<400> SEQUENCE: 49

Glu Ser Lys Tyr Gly Pro Pro Cys Pro Ser Cys Pro Ala Pro Glu Phe
1               5                   10                  15

Leu Gly Gly Pro
            20

<210> SEQ ID NO 50
<211> LENGTH: 5
<212> TYPE: PRT
<213> ORGANISM: Artificial Sequence
<220> FEATURE:
<223> OTHER INFORMATION: Synthetic peptide

<400> SEQUENCE: 50

Gly Gly Gly Gly Ser
1               5

<210> SEQ ID NO 51
<211> LENGTH: 15
<212> TYPE: PRT
<213> ORGANISM: Artificial Sequence
<220> FEATURE:
<223> OTHER INFORMATION: Synthetic peptide

<400> SEQUENCE: 51

Gly Gly Gly Gly Ser Gly Gly Gly Ser Gly Gly Gly Ser
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: Synthetic peptide

<400> SEQUENCE: 52

Gly Gly Ser Gly Gly Ser Gly Gly Gly Ser Gly Gly Gly Gly Ser
1               5                   10                  15

<210> SEQ ID NO 53
<211> LENGTH: 8
<212> TYPE: PRT
<213> ORGANISM: Artificial Sequence
<220> FEATURE:
<223> OTHER INFORMATION: Synthetic peptide

<400> SEQUENCE: 53

Gly Gly Ala Gly Ala Gly Ala Gly
1               5

<210> SEQ ID NO 54
<211> LENGTH: 15
<212> TYPE: PRT
<213> ORGANISM: Artificial Sequence
```

```
<220> FEATURE:
<223> OTHER INFORMATION: Synthetic peptide

<400> SEQUENCE: 54

Arg Gly Arg Gly Arg Gly Arg Gly Arg Gly Arg Gly Gly Ser
1               5                   10                  15

<210> SEQ ID NO 55
<211> LENGTH: 45
<212> TYPE: PRT
<213> ORGANISM: Artificial Sequence
<220> FEATURE:
<223> OTHER INFORMATION: Synthetic peptide
<220> FEATURE:
<221> NAME/KEY: MOD_RES
<222> LOCATION: (1)..(45)
<223> OTHER INFORMATION: Each Lys is glycosylated
<220> FEATURE:
<221> NAME/KEY: misc_feature
<222> LOCATION: (1)..(45)
<223> OTHER INFORMATION: Every Xaa is any amino acid

<400> SEQUENCE: 55

Arg Asp Gly Thr Pro Gly Glu Lys Gly Glu Lys Gly Asp Xaa Gly Leu
1               5                   10                  15

Xaa Gly Pro Gly Glu Xaa Gly Xaa Xaa Gly Xaa Xaa Gly Xaa Glu Gly
            20                  25                  30

Pro Arg Gly Phe Pro Gly Xaa Xaa Gly Arg Lys Gly Glu
        35                  40                  45

<210> SEQ ID NO 56
<211> LENGTH: 8
<212> TYPE: PRT
<213> ORGANISM: Artificial Sequence
<220> FEATURE:
<223> OTHER INFORMATION: Synthetic peptide

<400> SEQUENCE: 56

Gly Glu Lys Gly Glu Lys Gly Asp
1               5

<210> SEQ ID NO 57
<211> LENGTH: 4
<212> TYPE: PRT
<213> ORGANISM: Artificial Sequence
<220> FEATURE:
<223> OTHER INFORMATION: Synthetic peptide

<400> SEQUENCE: 57

Gly Pro Gly Glu
1

<210> SEQ ID NO 58
<211> LENGTH: 5
<212> TYPE: PRT
<213> ORGANISM: Artificial Sequence
<220> FEATURE:
<223> OTHER INFORMATION: Synthetic peptide

<400> SEQUENCE: 58

Gly Arg Lys Gly Glu
1               5

<210> SEQ ID NO 59
<211> LENGTH: 15
<212> TYPE: PRT
<213> ORGANISM: Artificial Sequence
<220> FEATURE:
```

<223> OTHER INFORMATION: Synthetic peptide

<400> SEQUENCE: 59

Gly Glu Lys Gly Glu Lys Gly Asp Pro Gly Pro Lys Gly Asp Pro
1               5                   10                  15

<210> SEQ ID NO 60
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(3)
<223> OTHER INFORMATION: Gly-Pro-Pro may repeat indefinitely
<220> FEATURE:
<221> NAME/KEY: misc_feature
<222> LOCATION: (19)..(21)
<223> OTHER INFORMATION: Gly-Pro-Pro may repeat indefinitely

<400> SEQUENCE: 60

Gly Pro Pro Gly Glu Lys Gly Glu Lys Gly Asp Pro Gly Pro Lys Gly
1               5                   10                  15

Asp Pro Gly Pro Pro
            20

<210> SEQ ID NO 61
<211> LENGTH: 172
<212> TYPE: PRT
<213> ORGANISM: Artificial Sequence
<220> FEATURE:
<223> OTHER INFORMATION: Synthetic

<400> SEQUENCE: 61

Ala Thr Pro Ala Pro Lys Ser Cys Pro Glu Arg His Tyr Trp Ala Gln
1               5                   10                  15

Gly Lys Leu Cys Cys Gln Met Cys Glu Pro Gly Thr Phe Leu Val Lys
            20                  25                  30

Asp Cys Asp Gln His Arg Lys Ala Ala Gln Cys Asp Pro Cys Ile Pro
        35                  40                  45

Gly Val Ser Phe Ser Pro Asp His His Thr Arg Pro His Cys Glu Ser
    50                  55                  60

Cys Arg His Cys Asn Ser Gly Leu Leu Val Arg Asn Cys Thr Ile Thr
65                  70                  75                  80

Ala Asn Ala Glu Cys Ala Cys Arg Asn Gly Trp Gln Cys Arg Asp Lys
                85                  90                  95

Glu Cys Thr Glu Cys Asp Pro Leu Pro Asn Pro Ser Leu Thr Ala Arg
            100                 105                 110

Ser Ser Gln Ala Leu Ser Pro His Pro Gln Pro Thr His Leu Pro Tyr
        115                 120                 125

Val Ser Glu Met Leu Glu Ala Arg Thr Ala Gly His Met Gln Thr Leu
    130                 135                 140

Ala Asp Phe Arg Gln Leu Pro Ala Arg Thr Leu Ser Thr His Trp Pro
145                 150                 155                 160

Pro Gln Arg Ser Leu Cys Ser Ser Asp Phe Ile Arg
                165                 170

<210> SEQ ID NO 62
<211> LENGTH: 173
<212> TYPE: PRT
<213> ORGANISM: Artificial Sequence
<220> FEATURE:

<223> OTHER INFORMATION: Synthetic

<400> SEQUENCE: 62

```
Glu Pro Pro Thr Ala Cys Arg Glu Lys Gln Tyr Leu Ile Asn Ser Gln
1               5                   10                  15

Cys Cys Ser Leu Cys Gln Pro Gly Gln Lys Leu Val Ser Asp Cys Thr
            20                  25                  30

Glu Phe Thr Glu Thr Glu Cys Leu Pro Cys Gly Glu Ser Glu Phe Leu
        35                  40                  45

Asp Thr Trp Asn Arg Glu Thr His Cys His Gln His Lys Tyr Cys Asp
    50                  55                  60

Pro Asn Leu Gly Leu Arg Val Gln Gln Lys Gly Thr Ser Glu Thr Asp
65                  70                  75                  80

Thr Ile Cys Thr Cys Glu Glu Gly Trp His Cys Thr Ser Glu Ala Cys
                85                  90                  95

Glu Ser Cys Val Leu His Arg Ser Cys Ser Pro Gly Phe Gly Val Lys
            100                 105                 110

Gln Ile Ala Thr Gly Val Ser Asp Thr Ile Cys Glu Pro Cys Pro Val
        115                 120                 125

Gly Phe Phe Ser Asn Val Ser Ser Ala Phe Glu Lys Cys His Pro Trp
    130                 135                 140

Thr Ser Cys Glu Thr Lys Asp Leu Val Val Gln Gln Ala Gly Thr Asn
145                 150                 155                 160

Lys Thr Asp Val Val Cys Gly Pro Gln Asp Arg Leu Arg
                165                 170
```

<210> SEQ ID NO 63
<211> LENGTH: 148
<212> TYPE: PRT
<213> ORGANISM: Artificial Sequence
<220> FEATURE:
<223> OTHER INFORMATION: Synthetic

<400> SEQUENCE: 63

```
Gln Val Thr Asp Ile Asn Ser Lys Gly Leu Glu Leu Arg Lys Thr Val
1               5                   10                  15

Thr Thr Val Glu Thr Gln Asn Leu Glu Gly Leu His His Asp Gly Gln
            20                  25                  30

Phe Cys His Lys Pro Cys Pro Pro Gly Glu Arg Lys Ala Arg Asp Cys
        35                  40                  45

Thr Val Asn Gly Asp Glu Pro Asp Cys Val Pro Cys Gln Glu Gly Lys
    50                  55                  60

Glu Tyr Thr Asp Lys Ala His Phe Ser Ser Lys Cys Arg Arg Cys Arg
65                  70                  75                  80

Leu Cys Asp Glu Gly His Gly Leu Glu Val Glu Ile Asn Cys Thr Arg
                85                  90                  95

Thr Gln Asn Thr Lys Cys Arg Cys Lys Pro Asn Phe Phe Cys Asn Ser
            100                 105                 110

Thr Val Cys Glu His Cys Asp Pro Cys Thr Lys Cys Glu His Gly Ile
        115                 120                 125

Ile Lys Glu Cys Thr Leu Thr Ser Asn Thr Lys Cys Lys Glu Glu Gly
    130                 135                 140

Ser Arg Ser Asn
145
```

<210> SEQ ID NO 64
<211> LENGTH: 197

```
<212> TYPE: PRT
<213> ORGANISM: Artificial Sequence
<220> FEATURE:
<223> OTHER INFORMATION: Synthetic

<400> SEQUENCE: 64

Gln Ala Val Pro Pro Tyr Ala Ser Glu Asn Gln Thr Cys Arg Asp Gln
1               5                   10                  15

Glu Lys Glu Tyr Tyr Glu Pro Gln His Arg Ile Cys Cys Ser Arg Cys
            20                  25                  30

Pro Pro Gly Thr Tyr Val Ser Ala Lys Cys Ser Arg Ile Arg Asp Thr
        35                  40                  45

Val Cys Ala Thr Cys Ala Glu Asn Ser Tyr Asn Glu His Trp Asn Tyr
    50                  55                  60

Leu Thr Ile Cys Gln Leu Cys Arg Pro Cys Asp Pro Val Met Gly Leu
65                  70                  75                  80

Glu Glu Ile Ala Pro Cys Thr Ser Lys Arg Lys Thr Gln Cys Arg Cys
                85                  90                  95

Gln Pro Gly Met Phe Cys Ala Ala Trp Ala Leu Glu Cys Thr His Cys
            100                 105                 110

Glu Leu Leu Ser Asp Cys Pro Pro Gly Thr Glu Ala Glu Leu Lys Asp
        115                 120                 125

Glu Val Gly Lys Gly Asn Asn His Cys Val Pro Cys Lys Ala Gly His
    130                 135                 140

Phe Gln Asn Thr Ser Ser Pro Ser Ala Arg Cys Gln Pro His Thr Arg
145                 150                 155                 160

Cys Glu Asn Gln Gly Leu Val Glu Ala Ala Pro Gly Thr Ala Gln Ser
                165                 170                 175

Asp Thr Thr Cys Lys Asn Pro Leu Glu Pro Leu Pro Pro Glu Met Ser
            180                 185                 190

Gly Thr Met Leu Met
        195

<210> SEQ ID NO 65
<211> LENGTH: 222
<212> TYPE: PRT
<213> ORGANISM: Artificial Sequence
<220> FEATURE:
<223> OTHER INFORMATION: Synthetic

<400> SEQUENCE: 65

Lys Glu Ala Cys Pro Thr Gly Leu Tyr Thr His Ser Gly Glu Cys Cys
1               5                   10                  15

Lys Ala Cys Asn Leu Gly Glu Gly Val Ala Gln Pro Cys Gly Ala Asn
            20                  25                  30

Gln Thr Val Cys Glu Pro Cys Leu Asp Ser Val Thr Phe Ser Asp Val
        35                  40                  45

Val Ser Ala Thr Glu Pro Cys Lys Pro Cys Thr Glu Cys Val Gly Leu
    50                  55                  60

Gln Ser Met Ser Ala Pro Cys Val Glu Ala Asp Asp Ala Val Cys Arg
65                  70                  75                  80

Cys Ala Tyr Gly Tyr Tyr Gln Asp Glu Thr Thr Gly Arg Cys Glu Ala
                85                  90                  95

Cys Arg Val Cys Glu Ala Gly Ser Gly Leu Val Phe Ser Cys Gln Asp
            100                 105                 110

Lys Gln Asn Thr Val Cys Glu Glu Cys Pro Asp Gly Thr Tyr Ser Asp
        115                 120                 125
```

Glu Ala Asn His Val Asp Pro Cys Leu Pro Cys Thr Val Cys Glu Asp
            130                 135                 140

Thr Glu Arg Gln Leu Arg Glu Cys Thr Arg Trp Ala Asp Ala Glu Cys
145                 150                 155                 160

Glu Glu Ile Pro Gly Arg Trp Ile Thr Arg Ser Thr Pro Pro Glu Gly
                165                 170                 175

Ser Asp Ser Thr Ala Pro Ser Thr Gln Glu Pro Glu Ala Pro Pro Glu
            180                 185                 190

Gln Asp Leu Ile Ala Ser Thr Val Ala Gly Val Val Thr Thr Val Met
            195                 200                 205

Gly Ser Ser Gln Pro Val Val Thr Arg Gly Thr Thr Asp Asn
            210                 215                 220

<210> SEQ ID NO 66
<211> LENGTH: 190
<212> TYPE: PRT
<213> ORGANISM: Artificial Sequence
<220> FEATURE:
<223> OTHER INFORMATION: Synthetic

<400> SEQUENCE: 66

Ile Tyr Pro Ser Gly Val Ile Gly Leu Val Pro His Leu Gly Asp Arg
1               5                   10                  15

Glu Lys Arg Asp Ser Val Cys Pro Gln Gly Lys Tyr Ile His Pro Gln
            20                  25                  30

Asn Asn Ser Ile Cys Cys Thr Lys Cys His Lys Gly Thr Tyr Leu Tyr
        35                  40                  45

Asn Asp Cys Pro Gly Pro Gly Gln Asp Thr Asp Cys Arg Glu Cys Glu
50                  55                  60

Ser Gly Ser Phe Thr Ala Ser Glu Asn His Leu Arg His Cys Leu Ser
65                  70                  75                  80

Cys Ser Lys Cys Arg Lys Glu Met Gly Gln Val Glu Ile Ser Ser Cys
                85                  90                  95

Thr Val Asp Arg Asp Thr Val Cys Gly Cys Arg Lys Asn Gln Tyr Arg
            100                 105                 110

His Tyr Trp Ser Glu Asn Leu Phe Gln Cys Phe Asn Cys Ser Leu Cys
        115                 120                 125

Leu Asn Gly Thr Val His Leu Ser Cys Gln Glu Lys Gln Asn Thr Val
130                 135                 140

Cys Thr Cys His Ala Gly Phe Phe Leu Arg Glu Asn Glu Cys Val Ser
145                 150                 155                 160

Cys Ser Asn Cys Lys Lys Ser Leu Glu Cys Thr Lys Leu Cys Leu Pro
                165                 170                 175

Gln Ile Glu Asn Val Lys Gly Thr Glu Asp Ser Gly Thr Thr
            180                 185                 190

<210> SEQ ID NO 67
<211> LENGTH: 235
<212> TYPE: PRT
<213> ORGANISM: Artificial Sequence
<220> FEATURE:
<223> OTHER INFORMATION: Synthetic

<400> SEQUENCE: 67

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

```
Ser Lys Cys Ser Pro Gly Gln His Ala Lys Val Phe Cys Thr Lys Thr
     35                  40                  45

Ser Asp Thr Val Cys Asp Ser Cys Glu Asp Ser Thr Tyr Thr Gln Leu
 50                  55                  60

Trp Asn Trp Val Pro Glu Cys Leu Ser Cys Gly Ser Arg Cys Ser Ser
 65                  70                  75                  80

Asp Gln Val Glu Thr Gln Ala Cys Thr Arg Glu Gln Asn Arg Ile Cys
                 85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
210                 215                 220

Pro Ser Pro Pro Ala Glu Gly Ser Thr Gly Asp
225                 230                 235

<210> SEQ ID NO 68
<211> LENGTH: 186
<212> TYPE: PRT
<213> ORGANISM: Artificial Sequence
<220> FEATURE:
<223> OTHER INFORMATION: Synthetic

<400> SEQUENCE: 68

Leu His Cys Val Gly Asp Thr Tyr Pro Ser Asn Asp Arg Cys Cys His
 1               5                  10                  15

Glu Cys Arg Pro Gly Asn Gly Met Val Ser Arg Cys Ser Arg Ser Gln
             20                  25                  30

Asn Thr Val Cys Arg Pro Cys Gly Pro Gly Phe Tyr Asn Asp Val Val
         35                  40                  45

Ser Ser Lys Pro Cys Lys Pro Cys Thr Trp Cys Asn Leu Arg Ser Gly
 50                  55                  60

Ser Glu Arg Lys Gln Leu Cys Thr Ala Thr Gln Asp Thr Val Cys Arg
 65                  70                  75                  80

Cys Arg Ala Gly Thr Gln Pro Leu Asp Ser Tyr Lys Pro Gly Val Asp
                 85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
```

```
                   165                 170                 175

Arg Pro Val Glu Val Pro Gly Gly Arg Ala
            180                 185

<210> SEQ ID NO 69
<211> LENGTH: 271
<212> TYPE: PRT
<213> ORGANISM: Artificial Sequence
<220> FEATURE:
<223> OTHER INFORMATION: Synthetic

<400> SEQUENCE: 69

Val Ala Glu Thr Pro Thr Tyr Pro Trp Arg Asp Ala Glu Thr Gly Glu
1               5                   10                  15

Arg Leu Val Cys Ala Gln Cys Pro Pro Gly Thr Phe Val Gln Arg Pro
            20                  25                  30

Cys Arg Arg Asp Ser Pro Thr Thr Cys Gly Pro Cys Pro Pro Arg His
        35                  40                  45

Tyr Thr Gln Phe Trp Asn Tyr Leu Glu Arg Cys Arg Tyr Cys Asn Val
    50                  55                  60

Leu Cys Gly Glu Arg Glu Glu Ala Arg Ala Cys His Ala Thr His
65                  70                  75                  80

Asn Arg Ala Cys Arg Cys Arg Thr Gly Phe Phe Ala His Ala Gly Phe
                85                  90                  95

Cys Leu Glu His Ala Ser Cys Pro Pro Gly Ala Gly Val Ile Ala Pro
            100                 105                 110

Gly Thr Pro Ser Gln Asn Thr Gln Cys Gln Pro Cys Pro Pro Gly Thr
        115                 120                 125

Phe Ser Ala Ser Ser Ser Ser Glu Gln Cys Gln Pro His Arg Asn
    130                 135                 140

Cys Thr Ala Leu Gly Leu Ala Leu Asn Val Pro Gly Ser Ser Ser His
145                 150                 155                 160

Asp Thr Leu Cys Thr Ser Cys Thr Gly Phe Pro Leu Ser Thr Arg Val
                165                 170                 175

Pro Gly Ala Glu Glu Cys Glu Arg Ala Val Ile Asp Phe Val Ala Phe
            180                 185                 190

Gln Asp Ile Ser Ile Lys Arg Leu Gln Arg Leu Leu Gln Ala Leu Glu
        195                 200                 205

Ala Pro Glu Gly Trp Gly Pro Thr Pro Arg Ala Gly Arg Ala Ala Leu
    210                 215                 220

Gln Leu Lys Leu Arg Arg Arg Leu Thr Glu Leu Leu Gly Ala Gln Asp
225                 230                 235                 240

Gly Ala Leu Leu Val Arg Leu Leu Gln Ala Leu Arg Val Ala Arg Met
                245                 250                 255

Pro Gly Leu Glu Arg Ser Val Arg Glu Arg Phe Leu Pro Val His
            260                 265                 270

<210> SEQ ID NO 70
<211> LENGTH: 361
<212> TYPE: PRT
<213> ORGANISM: Artificial Sequence
<220> FEATURE:
<223> OTHER INFORMATION: Synthetic

<400> SEQUENCE: 70

Phe Pro Gln Asp Arg Pro Phe Glu Asp Thr Cys His Gly Asn Pro Ser
1               5                   10                  15

His Tyr Tyr Asp Lys Ala Val Arg Arg Cys Cys Tyr Arg Cys Pro Met
```

```
                20                  25                  30
Gly Leu Phe Pro Thr Gln Gln Cys Pro Gln Arg Pro Thr Asp Cys Arg
            35                  40                  45

Lys Gln Cys Glu Pro Asp Tyr Tyr Leu Asp Glu Ala Asp Arg Cys Thr
 50                  55                  60

Ala Cys Val Thr Cys Ser Arg Asp Asp Leu Val Glu Lys Thr Pro Cys
 65                  70                  75                  80

Ala Trp Asn Ser Ser Arg Val Cys Glu Cys Arg Pro Gly Met Phe Cys
            85                  90                  95

Ser Thr Ser Ala Val Asn Ser Cys Ala Arg Cys Phe Phe His Ser Val
            100                 105                 110

Cys Pro Ala Gly Met Ile Val Lys Phe Pro Gly Thr Ala Gln Lys Asn
            115                 120                 125

Thr Val Cys Glu Pro Ala Ser Pro Gly Val Ser Pro Ala Cys Ala Ser
            130                 135                 140

Pro Glu Asn Cys Lys Glu Pro Ser Ser Gly Thr Ile Pro Gln Ala Lys
145                 150                 155                 160

Pro Thr Pro Val Ser Pro Ala Thr Ser Ala Ser Thr Met Pro Val
            165                 170                 175

Arg Gly Gly Thr Arg Leu Ala Gln Glu Ala Ala Ser Lys Leu Thr Arg
            180                 185                 190

Ala Pro Asp Ser Pro Ser Ser Val Gly Arg Pro Ser Ser Asp Pro Gly
            195                 200                 205

Leu Ser Pro Thr Gln Pro Cys Pro Glu Gly Ser Gly Asp Cys Arg Lys
            210                 215                 220

Gln Cys Glu Pro Asp Tyr Tyr Leu Asp Glu Ala Gly Arg Cys Thr Ala
225                 230                 235                 240

Cys Val Ser Cys Ser Arg Asp Asp Leu Val Glu Lys Thr Pro Cys Ala
            245                 250                 255

Trp Asn Ser Ser Arg Thr Cys Glu Cys Arg Pro Gly Met Ile Cys Ala
            260                 265                 270

Thr Ser Ala Thr Asn Ser Cys Ala Arg Cys Val Pro Tyr Pro Ile Cys
            275                 280                 285

Ala Ala Glu Thr Val Thr Lys Pro Gln Asp Met Ala Glu Lys Asp Thr
            290                 295                 300

Thr Phe Glu Ala Pro Pro Leu Gly Thr Gln Pro Asp Cys Asn Pro Thr
305                 310                 315                 320

Pro Glu Asn Gly Glu Ala Pro Ala Ser Thr Ser Pro Thr Gln Ser Leu
            325                 330                 335

Leu Val Asp Ser Gln Ala Ser Lys Thr Leu Pro Ile Pro Thr Ser Ala
            340                 345                 350

Pro Val Ala Leu Ser Ser Thr Gly Lys
            355                 360

<210> SEQ ID NO 71
<211> LENGTH: 163
<212> TYPE: PRT
<213> ORGANISM: Artificial Sequence
<220> FEATURE:
<223> OTHER INFORMATION: Synthetic

<400> SEQUENCE: 71

Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30
```

```
Ala Gly Gly Gln Arg Thr Cys Asp Ile Cys Arg Gln Cys Lys Gly Val
            35                  40                  45

Phe Arg Thr Arg Lys Glu Cys Ser Ser Thr Ser Asn Ala Glu Cys Asp
 50                  55                  60

Cys Thr Pro Gly Phe His Cys Leu Gly Ala Gly Cys Ser Met Cys Glu
 65                  70                  75                  80

Gln Asp Cys Lys Gln Gly Gln Glu Leu Thr Lys Lys Gly Cys Lys Asp
                 85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
            115                 120                 125

Lys Glu Arg Asp Val Val Cys Gly Pro Ser Pro Ala Asp Leu Ser Pro
            130                 135                 140

Gly Ala Ser Ser Val Thr Pro Pro Ala Pro Ala Arg Glu Pro Gly His
145                 150                 155                 160

Ser Pro Gln

<210> SEQ ID NO 72
<211> LENGTH: 216
<212> TYPE: PRT
<213> ORGANISM: Artificial Sequence
<220> FEATURE:
<223> OTHER INFORMATION: Synthetic

<400> SEQUENCE: 72

Ala Ser Gly Thr Glu Ala Ala Ala Thr Pro Ser Lys Val Trp Gly
 1               5                  10                  15

Ser Ser Ala Gly Arg Ile Glu Pro Arg Gly Gly Arg Gly Ala Leu
            20                  25                  30

Pro Thr Ser Met Gly Gln His Gly Pro Ser Ala Arg Ala Arg Ala Gly
            35                  40                  45

Arg Ala Pro Gly Pro Arg Pro Ala Arg Glu Ala Ser Pro Arg Leu Arg
 50                  55                  60

Val His Lys Thr Phe Lys Phe Val Val Val Gly Val Leu Leu Gln Val
 65                  70                  75                  80

Val Pro Ser Ser Ala Ala Thr Ile Lys Leu His Asp Gln Ser Ile Gly
            85                  90                  95

Thr Gln Gln Trp Glu His Ser Pro Leu Gly Glu Leu Cys Pro Pro Gly
            100                 105                 110

Ser His Arg Ser Glu His Pro Gly Ala Cys Asn Arg Cys Thr Glu Gly
            115                 120                 125

Val Gly Tyr Thr Asn Ala Ser Asn Asn Leu Phe Ala Cys Leu Pro Cys
            130                 135                 140

Thr Ala Cys Lys Ser Asp Glu Glu Glu Arg Ser Pro Cys Thr Thr Thr
145                 150                 155                 160

Arg Asn Thr Ala Cys Gln Cys Lys Pro Gly Thr Phe Arg Asn Asp Asn
            165                 170                 175

Ser Ala Glu Met Cys Arg Lys Cys Ser Arg Gly Cys Pro Arg Gly Met
            180                 185                 190

Val Lys Val Lys Asp Cys Thr Pro Trp Ser Asp Ile Glu Cys Val His
            195                 200                 205

Lys Glu Ser Gly Asn Gly His Asn
    210                 215
```

```
<210> SEQ ID NO 73
<211> LENGTH: 155
<212> TYPE: PRT
<213> ORGANISM: Artificial Sequence
<220> FEATURE:
<223> OTHER INFORMATION: Synthetic

<400> SEQUENCE: 73

Ile Thr Gln Gln Asp Leu Ala Pro Gln Gln Arg Ala Ala Pro Gln Gln
1               5                   10                  15

Lys Arg Ser Ser Pro Ser Glu Gly Leu Cys Pro Pro Gly His His Ile
            20                  25                  30

Ser Glu Asp Gly Arg Asp Cys Ile Ser Cys Lys Tyr Gly Gln Asp Tyr
        35                  40                  45

Ser Thr His Trp Asn Asp Leu Leu Phe Cys Leu Arg Cys Thr Arg Cys
    50                  55                  60

Asp Ser Gly Glu Val Glu Leu Ser Pro Cys Thr Thr Thr Arg Asn Thr
65                  70                  75                  80

Val Cys Gln Cys Glu Glu Gly Thr Phe Arg Glu Asp Ser Pro Glu
    85                  90                  95

Met Cys Arg Lys Cys Arg Thr Gly Cys Pro Arg Gly Met Val Lys Val
            100                 105                 110

Gly Asp Cys Thr Pro Trp Ser Asp Ile Glu Cys Val His Lys Glu Ser
        115                 120                 125

Gly Thr Lys His Ser Gly Glu Val Pro Ala Val Glu Thr Val Thr
    130                 135                 140

Ser Ser Pro Gly Thr Pro Ala Ser Pro Cys Ser
145                 150                 155

<210> SEQ ID NO 74
<211> LENGTH: 211
<212> TYPE: PRT
<213> ORGANISM: Artificial Sequence
<220> FEATURE:
<223> OTHER INFORMATION: Synthetic

<400> SEQUENCE: 74

Ala Thr Thr Ala Arg Gln Glu Glu Val Pro Gln Gln Thr Val Ala Pro
1               5                   10                  15

Gln Gln Gln Arg His Ser Phe Lys Gly Glu Glu Cys Pro Ala Gly Ser
            20                  25                  30

His Arg Ser Glu His Thr Gly Ala Cys Asn Pro Cys Thr Glu Gly Val
        35                  40                  45

Asp Tyr Thr Asn Ala Ser Asn Asn Glu Pro Ser Cys Phe Pro Cys Thr
    50                  55                  60

Val Cys Lys Ser Asp Gln Lys His Lys Ser Ser Cys Thr Met Thr Arg
65                  70                  75                  80

Asp Thr Val Cys Gln Cys Lys Glu Gly Thr Phe Arg Asn Glu Asn Ser
            85                  90                  95

Pro Glu Met Cys Arg Lys Cys Ser Arg Cys Pro Ser Gly Glu Val Gln
            100                 105                 110

Val Ser Asn Cys Thr Ser Trp Asp Asp Ile Gln Cys Val Glu Glu Phe
        115                 120                 125

Gly Ala Asn Ala Thr Val Glu Thr Pro Ala Ala Glu Glu Thr Met Asn
    130                 135                 140

Thr Ser Pro Gly Thr Pro Ala Pro Ala Ala Glu Glu Thr Met Asn Thr
145                 150                 155                 160

Ser Pro Gly Thr Pro Ala Pro Ala Ala Glu Glu Thr Met Thr Thr Ser
```

```
                    165                 170                 175
Pro Gly Thr Pro Ala Pro Ala Ala Glu Glu Thr Met Thr Thr Ser Pro
            180                 185                 190
Gly Thr Pro Ala Pro Ala Ala Glu Glu Thr Met Ile Thr Ser Pro Gly
            195                 200                 205
Thr Pro Ala
    210

<210> SEQ ID NO 75
<211> LENGTH: 156
<212> TYPE: PRT
<213> ORGANISM: Artificial Sequence
<220> FEATURE:
<223> OTHER INFORMATION: Synthetic

<400> SEQUENCE: 75

Ala Thr Ile Pro Arg Gln Asp Glu Val Pro Gln Gln Thr Val Ala Pro
1               5                  10                  15
Gln Gln Gln Arg Arg Ser Leu Lys Glu Glu Cys Pro Ala Gly Ser
            20                  25                  30
His Arg Ser Glu Tyr Thr Gly Ala Cys Asn Pro Cys Thr Glu Gly Val
        35                  40                  45
Asp Tyr Thr Ile Ala Ser Asn Asn Leu Pro Ser Cys Leu Leu Cys Thr
    50                  55                  60
Val Cys Lys Ser Gly Gln Thr Asn Lys Ser Ser Cys Thr Thr Thr Arg
65                  70                  75                  80
Asp Thr Val Cys Gln Cys Glu Lys Gly Ser Phe Gln Asp Lys Asn Ser
                85                  90                  95
Pro Glu Met Cys Arg Thr Cys Arg Thr Gly Cys Pro Arg Gly Met Val
            100                 105                 110
Lys Val Ser Asn Cys Thr Pro Arg Ser Asp Ile Lys Cys Lys Asn Glu
        115                 120                 125
Ser Ala Ala Ser Ser Thr Gly Lys Thr Pro Ala Ala Glu Glu Thr Val
    130                 135                 140
Thr Thr Ile Leu Gly Met Leu Ala Ser Pro Tyr His
145                 150                 155

<210> SEQ ID NO 76
<211> LENGTH: 183
<212> TYPE: PRT
<213> ORGANISM: Artificial Sequence
<220> FEATURE:
<223> OTHER INFORMATION: Synthetic

<400> SEQUENCE: 76

Ile Ala Pro Pro Cys Thr Ser Glu Lys His Tyr Glu His Leu Gly Arg
1               5                  10                  15
Cys Cys Asn Lys Cys Glu Pro Gly Lys Tyr Met Ser Ser Lys Cys Thr
            20                  25                  30
Thr Thr Ser Asp Ser Val Cys Leu Pro Cys Gly Pro Asp Glu Tyr Leu
        35                  40                  45
Asp Ser Trp Asn Glu Glu Asp Lys Cys Leu Leu His Lys Val Cys Asp
    50                  55                  60
Thr Gly Lys Ala Leu Val Ala Val Ala Gly Asn Ser Thr Thr Pro
65                  70                  75                  80
Arg Arg Cys Ala Cys Thr Ala Gly Tyr His Trp Ser Gln Asp Cys Glu
                85                  90                  95
Cys Cys Arg Arg Asn Thr Glu Cys Ala Pro Gly Leu Gly Ala Gln His
```

```
            100                 105                 110
Pro Leu Gln Leu Asn Lys Asp Thr Val Cys Lys Pro Cys Leu Ala Gly
            115                 120                 125

Tyr Phe Ser Asp Ala Phe Ser Ser Thr Asp Lys Cys Arg Pro Trp Thr
            130                 135                 140

Asn Cys Thr Phe Leu Gly Lys Arg Val Glu His His Gly Thr Glu Lys
145                 150                 155                 160

Ser Asp Ala Val Cys Ser Ser Ser Leu Pro Ala Arg Lys Pro Pro Asn
                165                 170                 175

Glu Pro His Val Tyr Leu Pro
            180

<210> SEQ ID NO 77
<211> LENGTH: 380
<212> TYPE: PRT
<213> ORGANISM: Artificial Sequence
<220> FEATURE:
<223> OTHER INFORMATION: Synthetic

<400> SEQUENCE: 77

Glu Thr Phe Pro Pro Lys Tyr Leu His Tyr Asp Glu Glu Thr Ser His
1               5                   10                  15

Gln Leu Leu Cys Asp Lys Cys Pro Pro Gly Thr Tyr Leu Lys Gln His
            20                  25                  30

Cys Thr Ala Lys Trp Lys Thr Val Cys Ala Pro Cys Pro Asp His Tyr
            35                  40                  45

Tyr Thr Asp Ser Trp His Thr Ser Asp Glu Cys Leu Tyr Cys Ser Pro
50                  55                  60

Val Cys Lys Glu Leu Gln Tyr Val Lys Gln Glu Cys Asn Arg Thr His
65                  70                  75                  80

Asn Arg Val Cys Glu Cys Lys Glu Gly Arg Tyr Leu Glu Ile Glu Phe
                85                  90                  95

Cys Leu Lys His Arg Ser Cys Pro Pro Gly Phe Gly Val Val Gln Ala
            100                 105                 110

Gly Thr Pro Glu Arg Asn Thr Val Cys Lys Arg Cys Pro Asp Gly Phe
            115                 120                 125

Phe Ser Asn Glu Thr Ser Ser Lys Ala Pro Cys Arg Lys His Thr Asn
            130                 135                 140

Cys Ser Val Phe Gly Leu Leu Leu Thr Gln Lys Gly Asn Ala Thr His
145                 150                 155                 160

Asp Asn Ile Cys Ser Gly Asn Ser Glu Ser Thr Gln Lys Cys Gly Ile
                165                 170                 175

Asp Val Thr Leu Cys Glu Glu Ala Phe Phe Arg Phe Ala Val Pro Thr
            180                 185                 190

Lys Phe Thr Pro Asn Trp Leu Ser Val Leu Val Asp Asn Leu Pro Gly
            195                 200                 205

Thr Lys Val Asn Ala Glu Ser Val Glu Arg Ile Lys Arg Gln His Ser
            210                 215                 220

Ser Gln Glu Gln Thr Phe Gln Leu Leu Lys Leu Trp Lys His Gln Asn
225                 230                 235                 240

Lys Asp Gln Asp Ile Val Lys Lys Ile Ile Gln Asp Ile Asp Leu Cys
                245                 250                 255

Glu Asn Ser Val Gln Arg His Ile Gly His Ala Asn Leu Thr Phe Glu
            260                 265                 270

Gln Leu Arg Ser Leu Met Glu Ser Leu Pro Gly Lys Lys Val Gly Ala
            275                 280                 285
```

```
Glu Asp Ile Glu Lys Thr Ile Lys Ala Cys Lys Pro Ser Asp Gln Ile
            290                 295                 300

Leu Lys Leu Leu Ser Leu Trp Arg Ile Lys Asn Gly Asp Gln Asp Thr
305                 310                 315                 320

Leu Lys Gly Leu Met His Ala Leu Lys His Ser Lys Thr Tyr His Phe
                325                 330                 335

Pro Lys Thr Val Thr Gln Ser Leu Lys Lys Thr Ile Arg Phe Leu His
            340                 345                 350

Ser Phe Thr Met Tyr Lys Leu Tyr Gln Lys Leu Phe Leu Glu Met Ile
                355                 360                 365

Gly Asn Gln Val Gln Ser Val Lys Ile Ser Cys Leu
            370                 375                 380

<210> SEQ ID NO 78
<211> LENGTH: 53
<212> TYPE: PRT
<213> ORGANISM: Artificial Sequence
<220> FEATURE:
<223> OTHER INFORMATION: Synthetic

<400> SEQUENCE: 78

Glu Gln Ala Pro Gly Thr Ala Pro Cys Ser Arg Gly Ser Ser Trp Ser
1               5                   10                  15

Ala Asp Leu Asp Lys Cys Met Asp Cys Ala Ser Cys Arg Ala Arg Pro
            20                  25                  30

His Ser Asp Phe Cys Leu Gly Cys Ala Ala Pro Pro Ala Pro Phe
            35                  40                  45

Arg Leu Leu Trp Pro
    50

<210> SEQ ID NO 79
<211> LENGTH: 165
<212> TYPE: PRT
<213> ORGANISM: Artificial Sequence
<220> FEATURE:
<223> OTHER INFORMATION: Synthetic

<400> SEQUENCE: 79

Met Ser Gly Leu Gly Arg Ser Arg Arg Gly Gly Arg Ser Arg Val Asp
1               5                   10                  15

Gln Glu Glu Arg Phe Pro Gln Gly Leu Trp Thr Gly Val Ala Met Arg
            20                  25                  30

Ser Cys Pro Glu Glu Gln Tyr Trp Asp Pro Leu Leu Gly Thr Cys Met
            35                  40                  45

Ser Cys Lys Thr Ile Cys Asn His Gln Ser Gln Arg Thr Cys Ala Ala
        50                  55                  60

Phe Cys Arg Ser Leu Ser Cys Arg Lys Glu Gln Gly Lys Phe Tyr Asp
65                  70                  75                  80

His Leu Leu Arg Asp Cys Ile Ser Cys Ala Ser Ile Cys Gly Gln His
                85                  90                  95

Pro Lys Gln Cys Ala Tyr Phe Cys Glu Asn Lys Leu Arg Ser Pro Val
            100                 105                 110

Asn Leu Pro Pro Glu Leu Arg Arg Gln Arg Ser Gly Glu Val Glu Asn
            115                 120                 125

Asn Ser Asp Asn Ser Gly Arg Tyr Gln Gly Leu Glu His Arg Gly Ser
        130                 135                 140

Glu Ala Ser Pro Ala Leu Pro Gly Leu Lys Leu Ser Ala Asp Gln Val
145                 150                 155                 160
```

Ala Leu Val Tyr Ser
            165

<210> SEQ ID NO 80
<211> LENGTH: 78
<212> TYPE: PRT
<213> ORGANISM: Artificial Sequence
<220> FEATURE:
<223> OTHER INFORMATION: Synthetic

<400> SEQUENCE: 80

Met Arg Arg Gly Pro Arg Ser Leu Arg Gly Arg Asp Ala Pro Ala Pro
1               5                   10                  15

Thr Pro Cys Val Pro Ala Glu Cys Phe Asp Leu Leu Val Arg His Cys
            20                  25                  30

Val Ala Cys Gly Leu Leu Arg Thr Pro Arg Pro Lys Pro Ala Gly Ala
        35                  40                  45

Ser Ser Pro Ala Pro Arg Thr Ala Leu Gln Pro Gln Glu Ser Val Gly
    50                  55                  60

Ala Gly Ala Gly Glu Ala Ala Leu Pro Leu Pro Gly Leu Leu
65                  70                  75

<210> SEQ ID NO 81
<211> LENGTH: 164
<212> TYPE: PRT
<213> ORGANISM: Artificial Sequence
<220> FEATURE:
<223> OTHER INFORMATION: Synthetic

<400> SEQUENCE: 81

Leu Pro Ser Cys Lys Glu Asp Glu Tyr Pro Val Gly Ser Glu Cys Cys
1               5                   10                  15

Pro Lys Cys Ser Pro Gly Tyr Arg Val Lys Glu Ala Cys Gly Glu Leu
            20                  25                  30

Thr Gly Thr Val Cys Glu Pro Cys Pro Pro Gly Thr Tyr Ile Ala His
        35                  40                  45

Leu Asn Gly Leu Ser Lys Cys Leu Gln Cys Gln Met Cys Asp Pro Ala
    50                  55                  60

Met Gly Leu Arg Ala Ser Arg Asn Cys Ser Arg Thr Glu Asn Ala Val
65                  70                  75                  80

Cys Gly Cys Ser Pro Gly His Phe Cys Ile Val Gln Asp Gly Asp His
                85                  90                  95

Cys Ala Ala Cys Arg Ala Tyr Ala Thr Ser Ser Pro Gly Gln Arg Val
            100                 105                 110

Gln Lys Gly Gly Thr Glu Ser Gln Asp Thr Leu Cys Gln Asn Cys Pro
        115                 120                 125

Pro Gly Thr Phe Ser Pro Asn Gly Thr Leu Glu Glu Cys Gln His Gln
    130                 135                 140

Thr Lys Cys Ser Trp Leu Val Thr Lys Ala Gly Ala Gly Thr Ser Ser
145                 150                 155                 160

Ser His Trp Val

<210> SEQ ID NO 82
<211> LENGTH: 54
<212> TYPE: PRT
<213> ORGANISM: Artificial Sequence
<220> FEATURE:
<223> OTHER INFORMATION: Synthetic

<400> SEQUENCE: 82

```
Met Leu Gln Met Ala Gly Gln Cys Ser Gln Asn Glu Tyr Phe Asp Ser
1               5                   10                  15

Leu Leu His Ala Cys Ile Pro Cys Gln Leu Arg Cys Ser Ser Asn Thr
            20                  25                  30

Pro Pro Leu Thr Cys Gln Arg Tyr Cys Asn Ala Ser Val Thr Asn Ser
            35                  40                  45

Val Lys Gly Thr Asn Ala
        50
```

<210> SEQ ID NO 83
<211> LENGTH: 137
<212> TYPE: PRT
<213> ORGANISM: Artificial Sequence
<220> FEATURE:
<223> OTHER INFORMATION: Synthetic

<400> SEQUENCE: 83

```
Gln Arg Pro Thr Gly Gly Pro Gly Cys Gly Pro Gly Arg Leu Leu Leu
1               5                   10                  15

Gly Thr Gly Thr Asp Ala Arg Cys Cys Arg Val His Thr Thr Arg Cys
            20                  25                  30

Cys Arg Asp Tyr Pro Gly Glu Glu Cys Cys Ser Glu Trp Asp Cys Met
            35                  40                  45

Cys Val Gln Pro Glu Phe His Cys Gly Asp Pro Cys Cys Thr Thr Cys
        50                  55                  60

Arg His His Pro Cys Pro Pro Gly Gln Gly Val Gln Ser Gln Gly Lys
65                  70                  75                  80

Phe Ser Phe Gly Phe Gln Cys Ile Asp Cys Ala Ser Gly Thr Phe Ser
                85                  90                  95

Gly Gly His Glu Gly His Cys Lys Pro Trp Thr Asp Cys Thr Gln Phe
            100                 105                 110

Gly Phe Leu Thr Val Phe Pro Gly Asn Lys Thr His Asn Ala Val Cys
            115                 120                 125

Val Pro Gly Ser Pro Pro Ala Glu Pro
            130                 135
```

<210> SEQ ID NO 84
<211> LENGTH: 141
<212> TYPE: PRT
<213> ORGANISM: Artificial Sequence
<220> FEATURE:
<223> OTHER INFORMATION: Synthetic

<400> SEQUENCE: 84

```
Glu Ser Gly Asp Cys Arg Gln Gln Glu Phe Arg Asp Arg Ser Gly Asn
1               5                   10                  15

Cys Val Pro Cys Asn Gln Cys Gly Pro Gly Met Glu Leu Ser Lys Glu
            20                  25                  30

Cys Gly Phe Gly Tyr Gly Glu Asp Ala Gln Cys Val Thr Cys Arg Leu
            35                  40                  45

His Arg Phe Lys Glu Asp Trp Gly Phe Gln Lys Cys Lys Pro Cys Leu
        50                  55                  60

Asp Cys Ala Val Val Asn Arg Phe Gln Lys Ala Asn Cys Ser Ala Thr
65                  70                  75                  80

Ser Asp Ala Ile Cys Gly Asp Cys Leu Pro Gly Phe Tyr Arg Lys Thr
                85                  90                  95

Lys Leu Val Gly Phe Gln Asp Met Glu Cys Val Pro Cys Gly Asp Pro
            100                 105                 110
```

```
Pro Pro Pro Tyr Glu Pro His Cys Ala Ser Lys Val Asn Leu Val Lys
        115                 120                 125

Ile Ala Ser Thr Ala Ser Ser Pro Arg Asp Thr Ala Leu
    130                 135                 140

<210> SEQ ID NO 85
<211> LENGTH: 308
<212> TYPE: PRT
<213> ORGANISM: Artificial Sequence
<220> FEATURE:
<223> OTHER INFORMATION: Synthetic

<400> SEQUENCE: 85

Gln Pro Glu Gln Lys Ala Ser Asn Leu Ile Gly Thr Tyr Arg His Val
1               5                   10                  15

Asp Arg Ala Thr Gly Gln Val Leu Thr Cys Asp Lys Cys Pro Ala Gly
            20                  25                  30

Thr Tyr Val Ser Glu His Cys Thr Asn Thr Ser Leu Arg Val Cys Ser
        35                  40                  45

Ser Cys Pro Val Gly Thr Phe Thr Arg His Glu Asn Gly Ile Glu Lys
    50                  55                  60

Cys His Asp Cys Ser Gln Pro Cys Pro Trp Pro Met Ile Glu Lys Leu
65                  70                  75                  80

Pro Cys Ala Ala Leu Thr Asp Arg Glu Cys Thr Cys Pro Pro Gly Met
                85                  90                  95

Phe Gln Ser Asn Ala Thr Cys Ala Pro His Thr Val Cys Pro Val Gly
            100                 105                 110

Trp Gly Val Arg Lys Lys Gly Thr Glu Thr Glu Asp Val Arg Cys Lys
        115                 120                 125

Gln Cys Ala Arg Gly Thr Phe Ser Asp Val Pro Ser Ser Val Met Lys
    130                 135                 140

Cys Lys Ala Tyr Thr Asp Cys Leu Ser Gln Asn Leu Val Val Ile Lys
145                 150                 155                 160

Pro Gly Thr Lys Glu Thr Asp Asn Val Cys Gly Thr Leu Pro Ser Phe
                165                 170                 175

Ser Ser Ser Thr Ser Pro Ser Pro Gly Thr Ala Ile Phe Pro Arg Pro
            180                 185                 190

Glu His Met Glu Thr His Glu Val Pro Ser Ser Thr Tyr Val Pro Lys
        195                 200                 205

Gly Met Asn Ser Thr Glu Ser Asn Ser Ser Ala Ser Val Arg Pro Lys
    210                 215                 220

Val Leu Ser Ser Ile Gln Glu Gly Thr Val Pro Asp Asn Thr Ser Ser
225                 230                 235                 240

Ala Arg Gly Lys Glu Asp Val Asn Lys Thr Leu Pro Asn Leu Gln Val
                245                 250                 255

Val Asn His Gln Gln Gly Pro His His Arg His Ile Leu Lys Leu Leu
            260                 265                 270

Pro Ser Met Glu Ala Thr Gly Gly Glu Lys Ser Ser Thr Pro Ile Lys
        275                 280                 285

Gly Pro Lys Arg Gly His Pro Arg Gln Asn Leu His Lys His Phe Asp
    290                 295                 300

Ile Asn Glu His
305

<210> SEQ ID NO 86
<211> LENGTH: 175
```

```
<212> TYPE: PRT
<213> ORGANISM: Artificial Sequence
<220> FEATURE:
<223> OTHER INFORMATION: Synthetic

<400> SEQUENCE: 86

Gln Gly Gly Thr Arg Ser Pro Arg Cys Asp Cys Ala Gly Asp Phe His
1               5                   10                  15

Lys Lys Ile Gly Leu Phe Cys Cys Arg Gly Cys Pro Ala Gly His Tyr
            20                  25                  30

Leu Lys Ala Pro Cys Thr Glu Pro Cys Gly Asn Ser Thr Cys Leu Val
        35                  40                  45

Cys Pro Gln Asp Thr Phe Leu Ala Trp Glu Asn His His Asn Ser Glu
    50                  55                  60

Cys Ala Arg Cys Gln Ala Cys Asp Glu Gln Ala Ser Gln Val Ala Leu
65                  70                  75                  80

Glu Asn Cys Ser Ala Val Ala Asp Thr Arg Cys Gly Cys Lys Pro Gly
                85                  90                  95

Trp Phe Val Glu Cys Gln Val Ser Gln Cys Val Ser Ser Ser Pro Phe
            100                 105                 110

Tyr Cys Gln Pro Cys Leu Asp Cys Gly Ala Leu His Arg His Thr Arg
            115                 120                 125

Leu Leu Cys Ser Arg Arg Asp Thr Asp Cys Gly Thr Cys Leu Pro Gly
            130                 135                 140

Phe Tyr Glu His Gly Asp Gly Cys Val Ser Cys Pro Thr Ser Thr Leu
145                 150                 155                 160

Gly Ser Cys Pro Glu Arg Cys Ala Ala Val Cys Gly Trp Arg Gln
                165                 170                 175
```

TNF RECEPTOR FC FUSION PROTEINS AND IN VIVO METHODS OF USE

The present application claims priority under 35 U.S.C. §119 to Taiwanese patent application serial number 100148544, filed on Dec. 26, 2011, the entire contents of which are hereby expressly incorporated by reference.

TECHNICAL FIELD

The technical field relates to a Fc fusion protein.

BACKGROUND

Tumor necrosis factor-α (TNFα) is a key regulator of inflammatory responses and has been implicated in many pathological conditions, such as rheumatoid arthritis, inflammatory bowel disease, psoriatic arthritis, vasculitis, ankylosing spondylitis, and juvenile chronic arthritis.

TNFα is present on the cell surface as a homotrimeric protein in which each subunit is initially translated as a 26 kD type II transmembrane precursor protein by cells of the immune system, including macrophages and monocytes. After being cleaved at a site proximal to the transmembrane domain of TNFα by TNFα converting enzyme (TACE), a soluble trimeric form of TNFα (17 kD) is released into the blood and exerts its activity by binding to two structurally distinct type I and type II TNF receptors (TNFRI and TNFRII) on effector cells.

The transmembrane form of TNFα plays a dual role in transmitting signals as a ligand and as a receptor which relays signals back to the cell. Therefore, transmembrane TNFα plays an important role in local inflammation in a cell-to-cell contact manner.

Anti-TNFα agents, including infliximab, adalimumab, etanercept and certolizumab pegol, bind to transmembrane TNFα on transmembrane TNFα-transfected cells with similar binding affinities, but their binding affinities are weaker than for soluble TNFα (Kaymakcalan, Z., P. Sakorafas, et al. (2009). "Comparisons of affinities, avidities, and complement activation of adalimumab, infliximab, and etanercept in binding to soluble and membrane tumor necrosis factor." Clin. Immunol. 131(2): 308-316.). Previous reports indicated that infliximab, adalimumab and etanercept similarly bind to transmembrane TNFα on TNFα producing cells, and infliximab and adalimumab (two monoclonal antibodies) seem to transmit stronger inhibitory signals through transmembrane TNFα than etanercept (Nesbitt, A., G. Fossati, et al. (2007). "Mechanism of action of certolizumab pegol (CDP870): in vitro comparison with other anti-tumor necrosis factor alpha agents." *Inflamm Bowel Dis* 13(11): 1323-1332.). The binding effects of these antagonists on the transmembrane form of TNFα are different, and may cause different results on clinical diseases (Taylor, P. C. (2010). "Pharmacology of TNF blockade in rheumatoid arthritis and other chronic inflammatory diseases." *Curr Opin Pharmacol* 10(3): 308-315.).

Unlike anti-TNFα antibodies, etanercept is not clinically effective for the pathogenesis of granulomatous diseases, in which the transmembrane TNFα may play a critical role (Mitoma, H., T. Horiuchi, et al. (2008). "Mechanisms for cytotoxic effects of anti-tumor necrosis factor agents on transmembrane tumor necrosis factor alpha-expressing cells: comparison among infliximab, etanercept, and adalimumab." Arthritis Rheum 58(5): 1248-1257.). Etanercept is a dimeric molecule composed of the extracellular domain of TNF receptor 2 (p75 TNF receptor) and the Fc fragment of human IgG$_1$. It is currently being used for the treatment of rheumatoid arthritis. However, 25% to 38% of patients show no response. This is suspected to be partially due to insufficient affinity of this protein to TNFα. The bivalent etanercept molecule forms a 1:1 complex with the TNFα trimer in which two of the three receptor binding sites on TNFα are occupied by etanercept, and the third receptor binding site is open (Scallon, B., A. Cai, et al. (2002). "Binding and functional comparisons of two types of tumor necrosis factor antagonists." J Pharmacol Exp Ther 301(2): 418-426.). Cells expressing transmembrane TNFα that bind etanercept are not lysed in vitro in the presence or absence of complement (Arora, T., R. Padaki, et al. "Differences in binding and effector functions between classes of TNF antagonists." Cytokine 45(2): 124-131. (2009).). Previous reports show that etanercept exhibits a relative low affinity toward the transmembrane TNFα as compared with infliximab. It is hypothesized that the induction of apoptosis by high-affinity TNFα binding agents such as sTNFR1 or anti-TNFα antibody infliximab is due to ligation of transmembrane TNFα and not to the neutralization of secreted TNFα, which can be a survival factor for monocytic cells. Therefore, enhancement of the binding strength of the bivalent etanercept to transmembrane TNFα may be a solution for increasing the efficacy in the treatment of both rheumatoid arthritis and, possibly, Crohn's disease.

Functional affinity (avidity) is a measure of the overall binding strength of an antigen with many antigenic determinants and multivalent antibodies. Polymerization of antigen-binding partners greatly increases their availability (or valency) for binding to a group of specific identical ligands in very close proximity to a target cell. TNFα family receptors form homotrimers when bound to their cognate ligands. The effect of oligomerization of soluble chimeric receptors on their affinity to their ligands has been studied. It was found that the best results were not obtained with a trimer, as expected, but with pentamers. Trimers are as efficient as dimers, but five times less efficient than the pentamers (Holler, N., T. Kataoka, et al. (2000). "Development of improved soluble inhibitors of FasL and CD40L based on oligomerized receptors." J Immunol Methods 237(1-2): 159-173.).

Trivalent assembly of a heterologous target-binding domain by using a trimerization domain has been reported. Examples of trimerizing domains include C-propeptide of procollagens, coiled-coil neck domain of collectin family proteins, C-terminal portion of FasL and bacteriophage T4 fibritin foldon domain (Hoppe, H. J., P. N. Barlow, et al. (1994). "A parallel three stranded alpha-helical bundle at the nucleation site of collagen triple-helix formation." FEBS Lett 344(2-3): 191-195.; Frank, S., R. A. Kammerer, et al. (2001). "Stabilization of short collagen-like triple helices by protein engineering." J Mol Biol 308(5): 1081-1089; Holler, N., A. Tardivel, et al. (2003). "Two adjacent trimeric Fas ligands are required for Fas signaling and formation of a death-inducing signaling complex." Mol Cell Biol 23(4): 1428-1440.).

The target binding domain of these trimerized heterologous target-binding protein assemblies can be protein hormones, cytokines, lymphokines, growth factors, lectins, enzymes and soluble receptor fragments; or adhesion molecules, such as selectins and integrins.

A short alpha-helical collagen-like peptide capable of self-trimerization and propagation of the heterologous fusion proteins from either the C- or N-terminal direction has been reported in EP1798240B1. In comparison with the immunoglobulin G (IgG) molecules, there are disadvantages with these trimeric fusion molecules when they are used for therapeutic applications. The disadvantages include: (1) Downstream process—unlike immunoglobulin G (IgG) molecules which can be easily purified by affinity chromatographies on protein A or G-conjugated resins through binding to the Fc fragment of IgG, resulting in more than 98% in homogeneity of the product at the first step of purification scheme, purification of the above fusion proteins for therapeutic applications is a challenge since no commercial affinity columns are available; (2) Low serum half-life—the Fc fragment of the IgG molecule has an increased systemic half-life resulting from the binding of Fc to the neonatal Fc receptor (FcRn), which is present in endothelial cells that line blood vessels. Upon binding to FcRn, IgG is protected from degradation and re-cycled into circulation, keeping the molecule in circulation longer. The pharmacokinetic properties of these trimeric fusion proteins have been improved as the Fc fragment binds to the FcRn and is responsible for maintaining the long half-life of trimeric fusion proteins in circulation.

It is possible to introduce an Fc fragment to one end of the trimeric molecule to become a trimeric Fc fusion protein. It is speculated that such a trimeric Fc fusion protein can be purified more efficiently using protein A-conjugated resins; most importantly, it may confer a longer plasma half-life, resolving both purification and pharmacokinetics issues. Methods to generate trimeric Fc fusion proteins have been described by fusion of an Fc fragment with different TNF homology domains in an N-terminal to C-terminal direction and then expressed in mammalian cells as secretory fusion proteins (Muller, N., A. Wyzgol, et al. (2008). "Activity of soluble OX40 ligand is enhanced by oligomerization and cell surface immobilization." Febs J 275(9): 2296-2304. Wyzgol, A., N. Muller, et al. (2009). "Trimer stabilization, oligomerization, and antibody-mediated cell surface immobilization improve the activity of soluble trimers of CD27L, CD40L, 41BBL, and glucocorticoid-induced TNF receptor ligand." J Immunol 183(3): 1851-1861.). The TNF homology domain (THD) is located at the C-terminus of the TNF ligand family, and is responsible for trimerization of TNF ligands and the binding of their cognate receptors. The results indicated that when Fc fused with different THDs, the dimerization force of the Fc domain and the trimerization force of the different THD compete each other, resulting in different oligomerization patterns of dimer, trimer or hexamers. The production of homogeneous trimeric or hexameric Fc-THD fusions was hampered by the intrinsic low trimerization capability of the THD and a second trimeric coiled-coil domain of tenascin-C (TNC) was introduced in-between the Fc and THD domains to stabilize the homo-oligomeric structure. U.S. Patent Application Publication U.S. 2005/0255547 described that a hexameric polypeptide might be assembled by fusion of an extracellular domain of a TNF receptor family protein with a hexameric moiety, wherein the hexameric moiety can be either a "true" hexamer, or a combination of "dimer of trimer" or "trimer of dimer". Unfortunately, no examples are available to demonstrate the assembly of such a stable hexameric structure. In order to obtain a predominantly trimeric or/and hexameric Fc-containing fusion molecule, a novel trimerizing domain is needed to drive and stabilize the trimeric assembly of the fusion partners when a stable dimerizing Fc fragment is present.

The sequence Gly-Pro-Hyp is the most stable and common triplet in collagen and the peptide (Gly-Pro-Hyp)$_{10}$ (SEQ ID NO: 33) can self-associate into a highly stable triple helical structure in vitro (Chopra, R. K. and V. S. Ananthanarayanan (1982). "Conformational implications of enzymatic proline hydroxylation in collagen." Proc Natl Acad Sci USA 79(23): 7180-7184; Yang, W., V. C. Chan, et al. (1997). "Gly-Pro-Arg confers stability similar to Gly-Pro-Hyp in the collagen triple-helix of host-guest peptides." J Biol Chem 272(46): 28837-28840). Previously, a short collagen-like peptide (Gly-Pro-Pro)$_{10}$ (SEQ ID NO: 21) was adopted to drive the trimerization of its monomeric fusion partners by expression of the recombinant cDNA construct in a mammalian system (Fan, C. Y., C. C. Huang, et al. (2008). "Production of multivalent protein binders using a self-trimerizing collagen-like peptide scaffold." Faseb J 22(11): 3795-3804.). It is not known whether (Gly-Pro-Pro)$_{10}$ (SEQ ID NO: 21) is still capable of initiating trimeric assembly of its fusion partners in mammalian cells when a stable dimerization domain, such as the IgG Fc fragment, is introduced at either the N- or C-terminal end.

Thus, there is a need for a TNFα inhibiting molecule which is stable in circulation, binds to transmembrane TNFα with suitable avidity to be effective, and which forms a stable trimer or hexamer structure, even in the presence of protein domains which tend to form dimers.

SUMMARY

The embodiment of the invention is directed to a fusion protein comprising three or six monomer polypeptides, wherein each monomer polypeptide independently comprises:
 (a) an extracellular domain of a TNF receptor family or a single domain antibody,
 (b) a collagen-like domain comprising at least 8 G-P-X1 blocks, wherein X1 may be P or O and a trimerizing motif,
 (c) optionally, a hinge region of IgG or a glycine linker, and
 (d) an Fc domain comprising the CH2 and CH3 regions of human IgG.

The embodiment of the invention also encompasses a nucleic acid encoding a monomer polypeptide of any of the trimeric or hexameric fusion proteins above.

The embodiment of the invention is also directed to an expression vector that expresses the trimeric or hexameric fusion protein. The embodiment of the invention also is directed to a host cell comprising said expression vector.

The embodiment of the invention includes methods of lowering the level of TNFα signaling in vivo comprising administering to a patient in need thereof an effective amount of a protein comprising:
 a fusion protein having three or six monomer polypeptides, wherein each polypeptide comprises:
  (a) an extracellular domain of a TNF receptor family or a single domain antibody,
  (b) a collagen-like domain comprising at least 8 G-P-X1 blocks, wherein X1 may be P or O and a trimerizing motif,
  (c) optionally, a hinge region of IgG or a glycine linker, and (d) an Fc domain comprising the CH2 and CH3 regions of human IgG.

The embodiment of the invention also includes methods of treating one or more of rheumatoid arthritis, inflammatory bowel disease, psoriatic arthritis, vasculitis, ankylosing spondylitis, and juvenile chronic arthritis comprising administering to a patient in need thereof an effective amount of a composition comprising:
 a fusion protein comprising three or six monomer polypeptides, wherein each polypeptide comprises:
  (a) an extracellular domain of a TNF receptor family or a single domain antibody,
  (b) a collagen-like domain comprising at least 8 G-P-X1 blocks, wherein X1 may be P or O and a trimerizing motif,
  (c) optionally, a hinge region of IgG or a glycine linker, and (d) a Fc domain comprising the CH2 and CH3 regions of human IgG, in a pharmaceutically acceptable carrier.

The embodiment of the invention also encompasses a kit comprising the fusion proteins discussed above.

BRIEF DESCRIPTION OF THE DRAWING

FIGS. 2A-E depict the structural characterization of the various Fc fusion molecules purified from culture media by protein A column chromatographies according to the embodiments.

DETAILED DESCRIPTION

Figure 1:
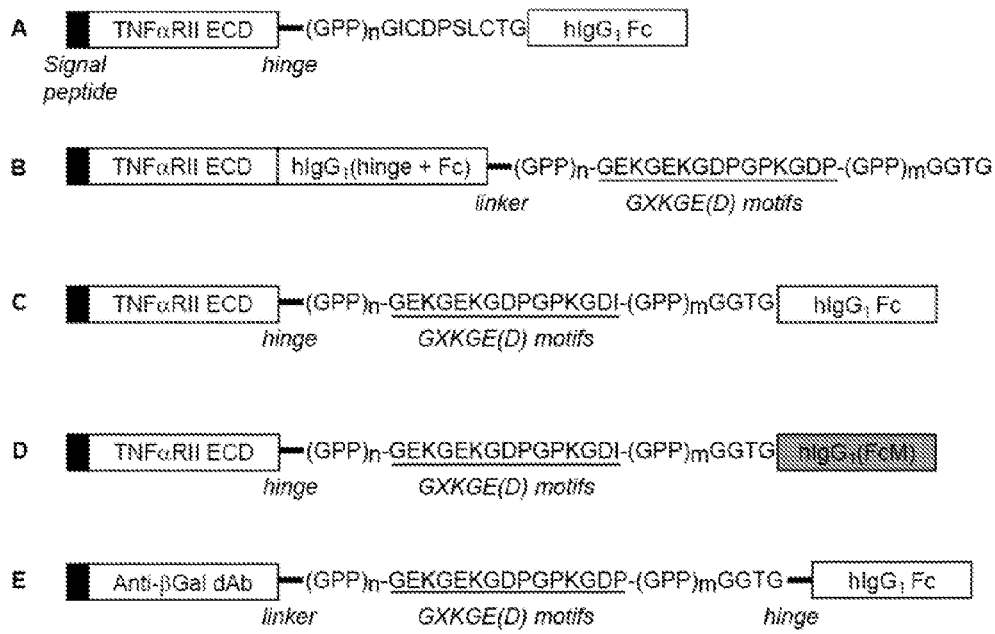
FIG. 1 is a schematic representation of different formats of Fc fusion molecules according to the embodiments. The GXKGE(D) motifs (SEQ ID NO: 34) vary in each format. Format A reflects a collagen-like domain including a disulfide knot, SEQ ID NO: 22. Format B reflects a collagen-like domain of SEQ ID NO: 22. Format C reflects a collagen-like domain of one of SEQ ID NO: 23 (n=4, m=4), SEQ ID NO: 24 (n=5, m=4), or SEQ ID NO: 25 (n=6, m=6). Format D has a collagen-like domain of SEQ ID NO: 35. Format E has a collagen-like domain of SEQ ID NO: 22
Figure 3:
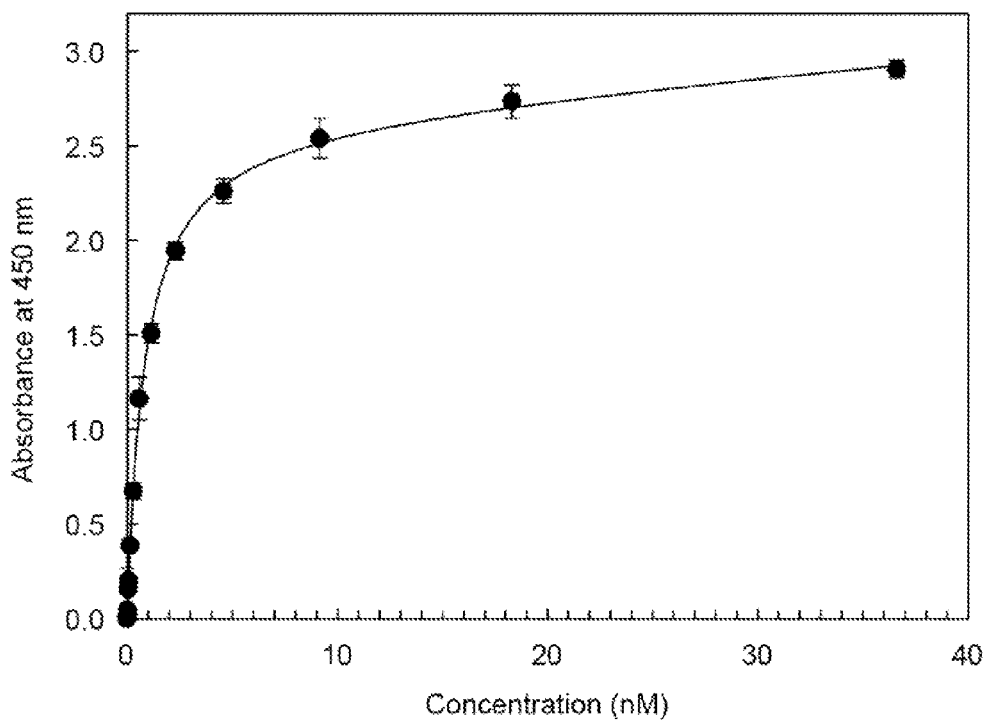
FIG. 3 depicts the binding of bGalCS6hFc to β-galactosidase by ELISA according to the embodiments.
Figure 4:
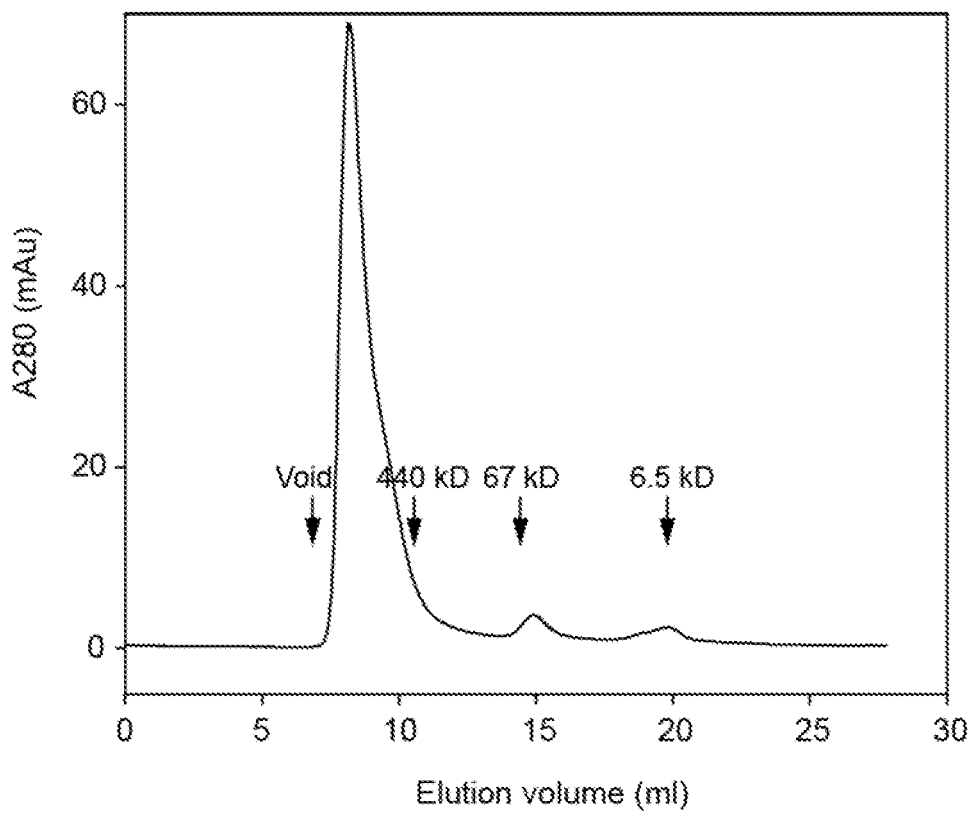
FIG. 4 depicts the separation of EnbCS6hFc by gel filtration according to the embodiments.

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

The embodiments of the invention relate to compositions, methods, and kits comprising a fusion protein. The fusion proteins of the embodiments of the invention are stable in circulation, bind to transmembrane TNFα with suitable avidity to be effective in vitro and in vivo, and form a stable trimer or hexamer structure, even in the presence of molecules which tend to form dimers.

The fusion proteins of the embodiments of the present invention comprise monomer polypeptides which in one embodiment have at least a binding domain, optionally a hinge region, a collagen-like domain and the Fc domain of a human IgG. In one embodiment, the fusion proteins comprise monomer polypeptides which have at least an extracellular domain of a TNF receptor family, optionally a hinge region, a collagen-like domain, and the Fc domain of human IgG$_1$. In one embodiment, the monomer polypeptides have at least the V$_H$ domain of an antibody, a linker, a collagen-like domain, optionally a hinge region of human IgG, and the Fc domain of human IgG$_1$.

I. General Structure

A. Binding Domain a. TNF Receptor Protein Family

In one embodiment, a collagen-like domain can be fused in-frame to a binding domain in a fusion polypeptide, such that the collagen-like domain drives trimerization of the fusion polypeptide, which retains its ability to bind its ligand. The binding domain can be, for example, a cytokine domain, a cytokine receptor domain, or an antibody domain. In one embodiment, the binding domain is an extracellular domain of a TNF receptor protein family. In one embodiment, the binding domain is an extracellular domain of a TNFα receptor. In one embodiment, a collagen-like domain can be fused in-frame to the extracellular domain of TNFαRII to generate a monomer polypeptide which then assembles into a trimeric or hexameric fusion protein.

b. Single Domain Antibody

In one embodiment, the fusion protein binding region can be a region of an antibody. In one embodiment, the region is an antigen-binding fragment of an antibody. In one embodiment, the fusion protein binding region can be the V$_H$ domain of an antibody. In one embodiment the fusion protein binding region is the V$_H$ domain of anti-β-galactosidase (β-gal).

B. Hinge Region

The fusion proteins of the embodiments of the present invention optionally include a "hinge region." In one embodiment, the hinge region is an approximately 4-15 amino acid long sequence. It may be the hinge region of a human IgG or a glycine linker. In one embodiment, the hinge region of a human IgG is the hinge region of human IgG$_1$, IgG$_2$, IgG$_3$ or human IgG$_4$ with the following sequences.

| Amino acid sequences of the hinge region of human Immunoglobulins | | |
|---|---|---|
| SEQ ID NO: 46 | Human IgG$_1$ | EPKSCDKTHTCPPCPAPEL LGGP |
| SEQ ID NO: 47 | Human IgG$_2$ | ERKCCVECPPCPAPPVAGP |
| SEQ ID NO: 48 | Human IgG$_3$ | ELKTPLGDTTHTCPRCPAP ELLGGP |
| SEQ ID NO: 49 | Human IgG$_4$ | ESKYGPPCPSCPAPEFLGGP |

The "hinge region" is optional, and, even if present need not have a trimerizing effect on the claimed fusion peptides. However, it may also be designed to assist or emphasize the trimerizing tendencies of the collagen-like domain.

C. Collagen-Like Domain a. Basic Structure

Collagen is the most abundant protein in mammals. It is an extracellular matrix protein that contains one or more triple-helical regions (collagenous domains) with a repeating triplet sequence Gly-Pro-X, where X is frequently proline (amino acid code, P or Pro) or hydroxyproline (amino acid code, O or Hyp). The presence of such triplets allows three collagen polypeptide chains (α-chains) to fold into a triple-helical conformation. Many collagen-like proteins with collagenous domains are present in human serum and serve as an innate immune system in protection from infectious organisms. These include complement protein C1q, macrophage receptors, collectin family proteins—mannose binding lectin (MBL), ficolins and surfactant proteins A and D (SP-A and SP-D). A common structural feature among these "defense collagen" molecules is that all of them are in multi-trimeric protein units with a target-binding domain at the C-terminus. Consequently, multimerization significantly increases the functional affinity of the binding domain of these defense collagen molecules.

The sequence Gly-Pro-Hyp is the most stable and common triplet in collagen and the peptide (Gly-Pro-Hyp)$_{10}$ (SEQ ID NO: 33) can self-associate into a highly stable triple helical structure in vitro.

The stability of collagen trimers can be determined by measuring the melting temperature of the trimers. Many studies have examined the melting temperatures/stability of G-P-X1 repeats. Frank et al., (2001); Persikov et al., (2000) Biochemistry 39, 14960-14967; Persikov et al., (2004) Protein Sci. 13: 893-902; and Mohs et al., (2007) J. Biol. Chem. 282: 29757-29765. Based on these studies, the stability of various repeat structures can be predicted.

b. Trimerizing Motif

The present fusion proteins must be soluble heterologous proteins which form a trimer or a hexamer (dimer of trimers). One method to stabilize the trimer structure of the present fusion proteins is by increasing the repeat number of G-P-P triplet. However, the adhesion of human Glycoprotein VI on human platelets to cross-linked GPO triplet peptides increased with their GPO content (Smethurst, P. A., D. J. Onley, et al. (2007). "Structural basis for the platelet-collagen interaction: the smallest motif within collagen that recognizes and activates platelet Glycoprotein VI contains two glycine-proline-hydroxyproline triplets." J Biol Chem 282(2): 1296-1304.).

Another method to increase the stability of the trimer structure is to incorporate a trimerizing motif, such as a "GXKGE(D)" (SEQ ID NO: 34) motif. Examples of a trimerizing motif, including the "GXKGE(D)" (SEQ ID NO: 34) motif and variations thereof can be found in many proteins containing collagenous domain, including adiponectin, C1q/tumor necrosis factor-related proteins (CORPs) and collagen triple helix repeat containing 1 (Cthrc1).

Electrostatic interactions involving lysine make major contributions to collagen triple-helix stability (Persikov, A. V., J. A. Ramshaw, et al. (2005). "Electrostatic interactions involving lysine make major contributions to collagen triple-helix stability." Biochemistry 44(5): 1414-1422.). One analogous structure is the multimerization of adiponectin. Adiponectin includes four conserved trimerization domains. Studies have shown that adiponectin multimerization is dependent on hydroxylation and glycosylation of the lysine residues in the four conserved "GXKGE(D) motifs" (SEQ ID NO: 34) within the collagenous domain (Richards, A. A., T. Stephens, et al. (2006).

"Adiponectin multimerization is dependent on conserved lysines in the collagenous domain: evidence for regulation of multimerization by alterations in posttranslational modifications." Mol Endocrinol 20(7): 1673-1687.). Serum adiponectin consists of trimer, hexamer, and larger high-molecular-weight (HMW) multimers, and these HMW multimers appear to be the more bioactive forms. It is unclear whether the "GXKGE(D) motif" (SEQ ID NO: 34) is the driving force which stabilizes the trimeric structure through electrostatic interactions between the lysine and glutamate (or aspirate) residues. In the GXKGE(D) (SEQ ID NO: 34) motif, the X may be E, F, Q, P, R, T or V, and the motif may be repeated. However, mutation of modified lysines in the collagenous domain prevented formation of HMW multimer.

Hydroxylation and glycosylation of the four conserved lysine residues in the collagenous domain of adiponectin assists with trimer stabilizing. The glycosylation sites were mapped to several lysines (residues 68, 71, 80, and 104 of human adiponectin) located in the collagenous domain of adiponectin, each having the surrounding motif of GXKGE(D) (the "GXKGE(D) motif") (SEQ ID NO: 34). These four lysines were found to be hydroxylated and subsequently glycosylated. There is a possibility that this glycosylation has a potential role in the modulation of the insulin-sensitizing activity of adiponectin. J Biol Chem (2002) 277:19521.

The approaches described above are limited in their use because they may not support normal trimerizing and folding of a heterologous polypeptide, and may introduce a hetero-antigenic fragment associated with the risk of an immune response that could severely limit potential therapeutic applications. Thus, what is needed is an in vivo expression system capable of forming a thermally stable triple helical structure that drives the formation of a trimeric fusion protein, despite the presence of a strong dimerizing domain, enabling use of such trimerized polypeptides both in vitro and in vivo. The present fusion peptides may incorporate the specific features of each of these strategies into the more typical G-P-P/O repeat to stabilize the trimer structures.

D. Fc Domain

The present monomer polypeptides and fusion proteins also include the Fc domain of an IgG. Generally, an IgG is a dimeric structure. Accordingly, the inclusion of an Fc domain in a monomer polypeptide tends to promote dimeric structures.

However, the Fc domain increases the serum half-life of the present fusion proteins. Specifically in vivo, the Fc fragment domain binds the neonatal Fc receptor (FcRn), which is present on endothelial cells that line blood vessels. Upon binding to the FcRn, the fusion protein, like human IgG would be protected from degradation and re-cycled into circulation, keeping the molecule in circulation longer. The pharmacokinetic properties of the present trimeric fusion proteins have unexpectedly been improved, as shown by the binding of the Fc portion of the present fusion protein assemblies to FcRn.

Therefore, there is a need to reduce the dimerization propensity of the Fc domains. Destabilizing the dimerization power of the dimerization domains, which would not interfere the trimeric assembly of the fusion partners, is a way to obtain pure trimeric Fc fusion proteins. There are many non-covalent interactions between the two IgG1 Fc domains and are strong enough to maintain dimerization without the disulfide bonds. Change to the critical residues can weaken the dimerization force and lead to an increase in the population of monomeric Fc domain. For example, the strategy using sterically complementary "knobs-into-holes" mutations to redesign Ab heavy chains can also promote heterodimerization of IgG (Ridgway, J. B., L. G. Presta, et al. (1996). "'Knobs-into-holes' engineering of antibody CH3 domains for heavy chain heterodimerization." Protein Eng 9(7): 617-621.). Based on this strategy, structure-guided phage display was also used to select for combinations of interface residues of Fc CH3 domains that promote the formation of stable heterodimers (Atwell, S., J. B. Ridgway, et al. (1997). "Stable heterodimers from remodeling the domain interface of a homodimer using a phage display library." J Mol Biol 270(1): 26-35.). Previous research has been established that a T366S:L368A:Y407V mutant can form the most stable heterodimer of IgG and therefore indicates that this mutant has a weaker dimerization force than the non-mutant Fc domains. According to these results, the trimerizing domain fused with a mutant form of the Fc domain (FcM) obtains a pure trimeric FcM fusion protein.

E. Linker

The linker is a short peptide sequence which may be placed in between the Fc domain and the collagen-like domain or between the binding domain and the collagen-like domain. Preferably the linker is between 4 and 10 amino acids in length, and may have the sequence:

Alaalaalaglyglyglyglyser (SEQ ID NO: 18) or glyglyglyglyser (SEQ ID NO: 50).

Glycine Linker (G-linker): (GGGGS)$_3$ (SEQ ID NO: 51), the most commonly used linker of scFv contains a fifteen combination of glycine and serine residues.

GGSGGSGGGGSGGGS (SEQ ID NO: 52) U.S. Pat. No. 5,908,626: Hybrid with interferon-β and an immunoglobulin Fc joined by a peptide linker Glycine-alanine linker: GGAGAGAG (SEQ ID NO: 53)

Glycine-arginine linker: RGRGRGRGRGRGGGS (SEQ ID NO: 54).

F. Avidity

The soluble trimeric or hexameric fusion protein can bind a ligand in the binding domain. In one embodiment, the soluble trimeric or hexameric fusion protein has a functional affinity for its ligand of greater than $10^{-6}$ M. In one embodiment, the soluble trimeric or hexameric fusion protein has a functional affinity for its ligand of greater than $10^{-8}$ M. In one embodiment, the soluble trimeric or hexameric fusion protein has a functional affinity for its ligand of greater than $10^{-10}$ M. In certain embodiments, the soluble trimeric or hexameric fusion protein has a functional affinity (or affinity) for its ligand between $10^{-7}$ M and $10^{-12}$ M, between $10^{-8}$ M and $10^{-11}$ M, between $10^{-7}$ M and $10^{-10}$ M, between $10^{-8}$ M and $10^{-10}$ M, and between $10^{-9}$ M and $10^{-10}$ M.

G. Expression

In one embodiment, the trimeric or hexameric fusion protein is a soluble protein. A soluble protein is one that is soluble under physiological conditions. In one embodiment, the soluble trimeric or hexameric fusion protein is a secreted protein. A secreted fusion protein is one that is secreted by a cell. Secretion of a protein can be targeted by having a signal sequence on the polypeptide comprising the antibody domain.

Signal sequences may include:

(SEQ ID NO: 15)
MetGluThrAspThrLeuLeuLeuTrpValLeuLeuLeuTrpValPro

GlySerThrGly.

Mouse myeloma NS0 cells are a good expression system for recombinant collagen or collagen-like protein production and for the expression of the present fusion proteins. Additionally, CHO and CHO—S cells may be used for the recombinant collagen or collagen-like protein production and for the expression of the present fusion proteins.

The assembled fusion protein trimers of the embodiments of present invention include three monomer polypeptide sequences; a first, second and third fusion polypeptide. In one embodiment, the above-described first, second, and third fusion polypeptides are substantially identical, having at least 75% (e.g., any number between 75% and 100%, inclusive, e.g., 75%, 76% . . . 95%, 96%, 97%, 98%, or 99%) sequence identity to one another. A complex formed by three identical fusion polypeptides is a homotrimer. The three fusion polypeptides can be functional equivalents. A "functional equivalent" refers to a polypeptide derivative of a common polypeptide, e.g., a protein having one or more point mutations, insertions, deletions, truncations, a fusion protein, or a combination thereof, and retaining substantially the ability to form a triple helix coil and the activity of the heterologous domain, such as binding to a ligand. This is also the case with the hexamers, where there are six monomer polypeptide sequences. Again, each of the six monomer polypeptide sequences may be substantially identical. In one embodiment there are three copies of a first monomer fusion polypeptide sequence, and three copies of a second fusion polypeptide sequence. In one embodiment there may be two copies of a first fusion polypeptide sequence, two copies of a second fusion polypeptide sequence, and two copies of a third polypeptide sequence.

The percent identity can be determined, for example, by comparing sequence information using the GAP computer program, version 6.0 described by Devereux et al. (Nucl. Acids Res. 12:387, 1984) and available from the University of Wisconsin Genetics Computer Group (UWGCG). The GAP program utilizes the alignment method of Needleman and Wunsch (J. Mol. Biol. 48:443, 1970), as revised by Smith and Waterman (Adv. Appl. Math 2:482, 1981). The preferred default parameters for the GAP program include: (1) a unary comparison matrix (containing a value of 1 for identities and 0 for non-identities) for nucleotides, and the weighted comparison matrix of Gribskov and Burgess, Nucl. Acids Res. 14:6745, 1986, as described by Schwartz and Dayhoff, eds., Atlas of Protein Sequence and Structure, National Biomedical Research Foundation, pp. 353-358, 1979; (2) a penalty of 3.0 for each gap and an additional 0.10 penalty for each symbol in each gap; and (3) no penalty for end gaps.

Figure 9:
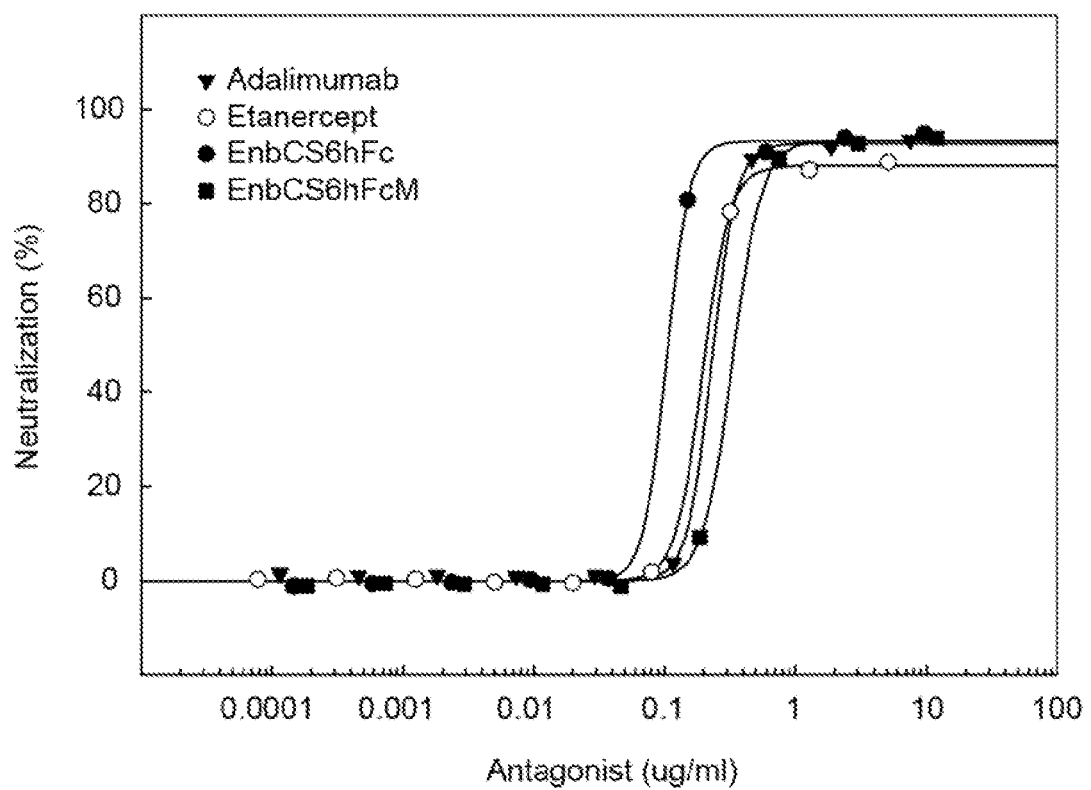
FIG. 9 depicts the neutralization activities of TNFα-mediated cytotoxicity in L929 cells by different TNFα antagonists according to the embodiments.
Figure 10:
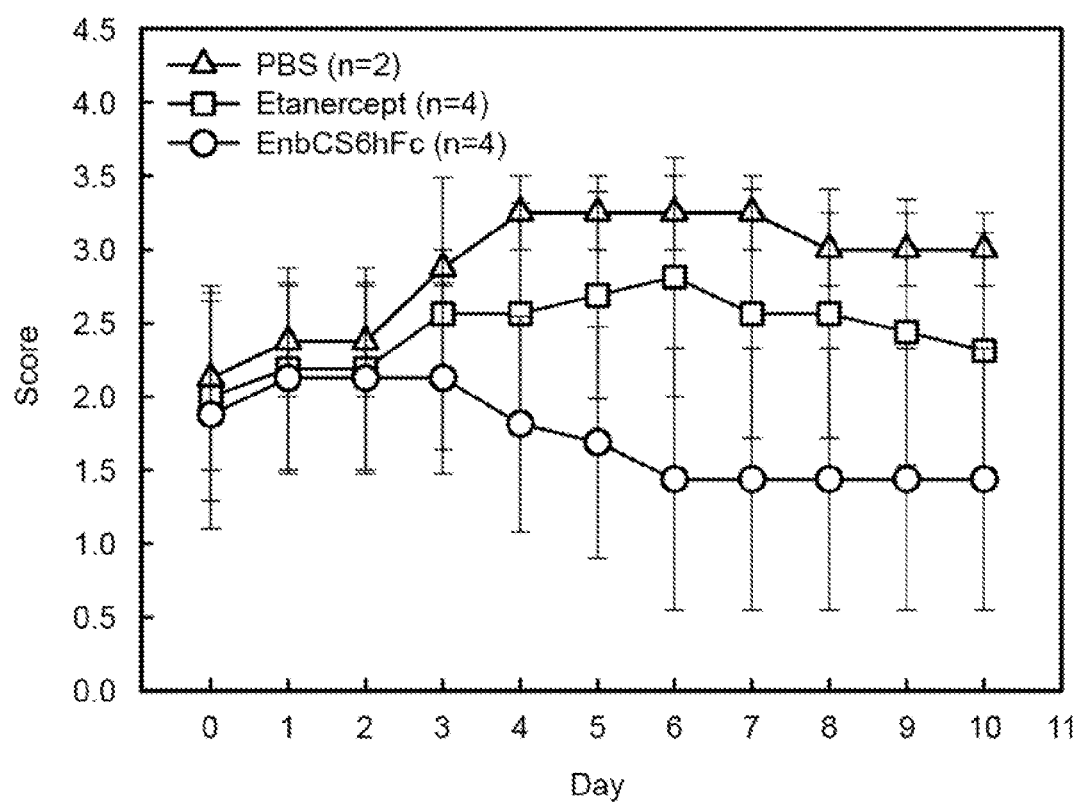
FIG. 10 depicts the efficacy of etanercept and EnbCS6hFc on arthritis mouse model according to the embodiments.

As used herein, the term "consensus sequence" refers to the sequence formed from the most frequently occurring amino acids (or nucleotides) in a family of related sequences (See e.g., Winnaker, From Genes to Clones (Verlagsgesellschaft, Weinheim, Germany 1987; see also Richards et al., FIG. 9). In a family of proteins, each position in the consensus sequence is occupied by the amino acid occurring most frequently at that position in the family. If two amino acids occur equally frequently, either can be included in the consensus sequence.

A heterologous polypeptide, nucleic acid, or gene is a polypeptide, nucleic acid, or gene that is associated with another polypeptide, nucleic acid, or gene with which it is not naturally associated. Two fused domains or sequences are heterologous to each other if they are not adjacent to each other in a naturally occurring protein or nucleic acid.

An "isolated" polypeptide or protein complex refers to a polypeptide or a protein complex substantially free from naturally associated molecules, i.e., it is at least 75% (i.e., any number between 75% and 100%, inclusive) pure by dry weight. Purity can be measured by any appropriate standard method, for example, by column chromatography, polyacrylamide gel electrophoresis, or HPLC analysis. An isolated polypeptide or protein complex of the embodiments of the invention can be purified from a natural source, produced by recombinant DNA techniques.

The three polypeptides that trimerize to form a trimeric fusion protein are non-contiguous. In another embodiment, the three polypeptides that trimerize to form a trimeric fusion protein are contiguous, i.e., translated as a single translation product. In this embodiment, the three polypeptides can be joined by two or more flexible hinge regions.

Binding Domain Number/Valence

A soluble trimeric or hexameric fusion peptide of the embodiments of the invention enjoys advantages over conventional TNF therapeutics. On the one hand, when two or more of the six binding domains are identical to each other, the protein complex can have 1-3 binding domains that are specific for one binding partner (e.g., antigen) in comparison with a conventional antibody or receptor, which has only one or two such domains. In other words, unlike a conventional antibody or receptor, which is only monovalent or divalent for an antigen, the protein complex can be di-, tri-, tetra-, penta-, or hexa-valent. As a result, it can be made to have affinities that are higher than a conventional antibody or receptor. Because of the higher affinities, smaller amounts of the protein complex and shorter incubation durations are needed than a conventional antibody to achieve the desired goals, for example, therapeutic effects, thereby lowering treatment costs and minimizing side effects (e.g., unwanted immune responses).

On the other hand, when two or more of the six domains are different from each other, a protein complex of this invention can have 2-6 binding domains that are specific for 2-6 different binding partners. Unifying multiple binding partner sites of different specificities into one unit, it has the ability to bring together multiple binding partners and therefore have desirable uses in therapy, tissue reconstruction, and assembly of active protein machinery (e.g., a multi-subunit enzyme) at the nanometer level.

The embodiments of the invention also encompasses an isolated nucleic acid that contains a sequence encoding the just-mentioned fusion polypeptide or a complement of the sequence. A nucleic acid refers to a DNA molecule (e.g., a cDNA or genomic DNA), an RNA molecule (e.g., an mRNA), or a DNA or RNA analog. A DNA or RNA analog can be synthesized from nucleotide analogs. The nucleic acid molecule can be single-stranded or double-stranded, but preferably is double-stranded DNA. An "isolated nucleic acid" is a nucleic acid, the structure of which is not identical to that of any naturally occurring nucleic acid or to that of any fragment of a naturally occurring genomic nucleic acid. The term therefore covers, for example, (a) a DNA which has the sequence of part of a naturally occurring genomic DNA molecule but is not flanked by both of the coding sequences that flank that part of the molecule in the genome of the organism in which it naturally occurs; (b) a nucleic acid incorporated into a vector or into the genomic DNA of a prokaryote or eukaryote in a manner such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. The nucleic acid described above can be used to express the polypeptide of this invention. For this purpose, one can operatively link the nucleic acid to suitable regulatory sequences to generate an expression vector.

A vector refers to a nucleic acid molecule capable of transporting another nucleic acid to which it has been linked. The vector can be capable of autonomous replication or integrate into a host DNA. Examples of a vector include a plasmid, cosmid, or viral vector. The vector of this invention includes a nucleic acid in a form suitable for expression of the nucleic acid in a host cell. Preferably the vector includes one or more regulatory sequences operatively linked to the nucleic acid sequence to be expressed. In one embodiment the expression vector is pSecTag2/Hygro (Invitrogen).

A "regulatory sequence" includes promoters, enhancers, and other expression control elements (e.g., polyadenylation signals). Regulatory sequences include those that direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vector can be introduced into host cells to produce the polypeptide of this invention. Also within the scope of the embodiments of the invention is a host cell that contains the above-described nucleic acid. Examples include E. coli cells, insect cells (e.g., using Drosophila S2 cells or baculovirus-infected insect cells), yeast cells, or mammalian cells (e.g., mouse myeloma NS0 cell). See e.g., Goeddel, (1990) Gene Expression Technology: Methods in Enzymology 185, Academic Press, San Diego, Calif.

The present monomer polypeptides or fusion proteins may also include nucleotide or protein sequences allowing for identification and purification. Such sequences can include restriction sites, tags, spacers, and other methods to purify or identify the nucleotide or protein sequence. Often such sequences are included in the nucleotide, and code for short amino acid sequences of 4-6 amino acids in length. They often appear in-between domains of the fusion proteins as artifacts, but do not materially affect the basic and novel characteristics of the invention so long as they do not prevent the assembly or maintenance of a trimer or hexamer structure.

To produce a fusion polypeptide of the embodiments of the invention, one can culture a host cell in a medium under conditions permitting expression of the polypeptide encoded by a nucleic acid of the embodiments of the invention, and purify the polypeptide from the cultured cell or the medium of the cell. Peptides containing collagen-like domains can be difficult to purify if there are no affinity tags. In the present fusion peptides, the Fc region assists with purification. Alternatively, the nucleic acid of this invention can be transcribed and translated in vitro, for example, using T7 promoter regulatory sequences and T7 polymerase.

To produce a protein complex of this invention, one can culture a host cell containing a first, second, and third nucleic acids respectively encoding the above-mentioned first, second, and third fusion polypeptides in a medium under a condition permitting expression of polypeptides encoded by the three nucleic acids and formation of a triple helix coil between the expressed polypeptides, and purifying the protein complex from the cultured cell or the medium of the cell. Preferably, the host cell is a eukaryotic cell containing an enzymatic activity that hydroxylates a proline residue.

For in vivo use in a human, a trimeric or hexameric fusion protein of the embodiments of the invention is of human origin. For example, it can include a human TNFαRII domain sequence fused in-frame to a collagen-like domain of human origin. Since many collagen-like proteins with collagenous domains are fairly stable in the blood, the scaffold domain fusion proteins should retain structural integrity in blood as well. Furthermore, the hinge region and Fc domains can be taken from a human IgG or humanized antibody.

The details of one or more embodiments of the invention are set forth in the accompanying drawing and the description below. Other features, objects, and advantages of the invention will be apparent from the description and drawing, and from the claims.

II. Specific Structure

A. Binding Domain a. TNF Receptor Protein Family

In one embodiment, a collagen-like domain can be fused in-frame to a binding domain in a fusion polypeptide, such that the collagen-like domain drives trimerization of the fusion polypeptide, which retains its ability to bind its ligand. The binding domain can be, for example, a cytokine domain, a cytokine receptor domain, or an antibody domain. In one embodiment, the binding domain is an extracellular domain of a TNF receptor protein family.

In one embodiment, the binding domain is an extracellular domain of a TNFα receptor family, including TNFR type I (p55), TNFR type II (p75), Fas (CD95), CD40, CD27, CD30, 4-1BB (CDw137), OX40 (CD134), LTBR, NGFR (CD271), DcR3, TRAILR-1 (CD261), TRAILR-2 (CD262), TRAILR-3 (CD263), TRAILR-4 (CD264), RANK (CD265), OPG (TR1), FN14 (CD266), TACI (CD267), BAFFR (CD268), HVEM (CD270), BCM (CD269), GITR (CD357), TAJ-alpha (TROY), DR6 (CD358) and DR3 (TRAMP). In one embodiment, the binding domain has at least 70% (e.g., any number between 70% and 100%, inclusive, e.g., 71%, 72% ... 95%, 96%, 97%, 98%, or 99%) to the extracellular domain of a TNFα receptor family. In one embodiment, a collagen-like domain can be fused in-frame to the extracellular domain of TNFαRII to generate a trimeric fusion protein. In one embodiment, the sequence of the binding domain is the extracellular domain of the TNFαRII having the following sequence:

(SEQ ID NO: 16)
AspAlaAlaGlnProAlaArgArgAlaLeuProAlaGlnValAlaPheThrProTyrAlaProGluProGlySerThrCys

ArgLeuArgGluTyrTyrAspGlnThrAlaGlnMetCysCysSerLysCysSerProGlyGlnHisAlaLysValPhe

CysThrLysThrSerAspThrValCysAspSerCysGluAspSerThrTyrThrGlnLeuTrpAsnTrpValProGluCys

LeuSerCysGlySerArgCysSerSerAspGlnValGluThrGlnAlaCysThrArgGluGlnAsnArgIleCysThrCys

ArgProGlyTrpTyrCysAlaLeuSerLysGlnGluGlyCysArgLeuCysAlaProLeuArgLysCysArgProGlyPhe

GlyValAlaArgProGlyThrGluThrSerAspValValCysLysProCysAlaProGlyThrPheSerAsnThrThrSer

SerThrAspIleCysArgProHisGlnIleCysAsnValValAlaIleProGlyAsnAlaSerMetAspAlaValCysThr

SerThrSerProThrArgSerMetAlaProGlyAlaValHisLeuProGlnProValSerThrArgSerGlnHisThrGln

ProThrProGluProSerThrAlaProSerThrSerPheLeuLeuProMetGlyProSerProProAlaGluGlySerThr

GlyAspAlaAlaAla.

Additional Extracellular domains and their sequences can be found in the Table below:

| Approved Symbol | Approved Name | Previous Symbols | Synonyms | Amino acid sequence of the extracellular domain |
|---|---|---|---|---|
| CD27 | CD27 molecule | TNFRSF7 | S152, Tp55 | ATPAPKSCPERHYWAQGKLCCQMCEPGTFLVKDCDQHRKAAQCDPCIPGVSFSPDHHTRPHCESCRHCNSGLLVRNCTITANAECACRNGWQCRDKECTECDPLPNPSLTARSSQALSPHPQPTHLPYVSEMLEARTAGHMQTLADFRQLPARTLSTHWPPQRSLCSSDFIR (SEQ ID NO: 61) |
| CD40 | CD40 molecule, TNF receptor superfamily member 5 | TNFRSF5 | p50, Bp50 | EPPTACREKQYLINSQCCSLCQPGQKLVSDCTEFTETECLPCGESEFLDTWNRETHCHQHKYCDPNLGLRVQQKGTSETDTICTCEEGWHCTSEACESCVLHRSCSPGFGVKQIATGVSDTICEPCPVGFFSNVSSAFEKCHPWTSCETKDLVVQQAGTNKTDVVCGPQDRLR (SEQ ID NO: 62) |
| FAS | Fas (TNF receptor superfamily, member 6) | FAS1, APT1, TNFRSF6 | CD95, APO-1 | QVTDINSKGLELRKTVTTVETQNLEGLHHDGQFCHKPCPPGERKARDCTVNGDEPDCVPCQEGKEYTDKAHFSSKCRRCRLCDEGHGLEVEINCTRTQNTKCRCKPNFFCNSTVCEHCDPCTKCEHGIIKECTLTSNTKCKEEGSRSN (SEQ ID NO: 63) |
| LTBR | lymphotoxin beta receptor (TNFR superfamily, member 3) | D12S370 | TNFCR, TNFR-RP, TNFR2-RP, TNF-R-III, TNFRSF3 | QAVPPYASENQTCRDQEKEYYEPQHRICCSRCPPGTYVSAKCSRIRDTVCATCAENSYNEHWNYLTICQLCRPCDPVMGLEEIAPCTSKRKTQCRCQPGMFCAAWALECTHCELLSDCPPGTEAELKDEVGKGNNHCVPCKAGHFQNTSSPSARCQPHTRCENQGLVEAAPGTAQSDTTCKNPLEPLPPEMSGTMLM (SEQ ID NO: 64) |
| NGFR | nerve growth factor receptor | | TNFRSF16, CD271, p75NTR | KEACPTGLYTHSGECCKACNLGEGVAQPCGANQTVCEPCLDSVTFSDVVSATEPCKPCTECVGLQSMSAPCVEADDAVCRCAYGYYQDETTGRCEACRVCEAGSGLVFSCQDKQNTVCEECPDGTYSDEANHVDPCLPCTVCEDTERQLRECTRWADAECEEIPGRWITRSTPPEGSDSTAPSTQEPEAPPEQDLIASTVAGVVTTVMGSSQPVVTRGTTDN (SEQ ID NO: 65) |
| TNFRSF1A | tumor necrosis factor | TNFR1 | TNF-R, TNFAR, TNFR60, | IYPSGVIGLVPHLGDREKRDSVCPQGKYIHPQNNSICCTKCHKGTYLYNDCPGPGQDTDCRECESGSFTASENHLRHCLSCSKCRKEMGQVEISSCTV |

| Approved Symbol | Approved Name | Previous Symbols | Synonyms | Amino acid sequence of the extracellular domain |
|---|---|---|---|---|
| | receptor superfamily, member 1A | | TNF-R-I, CD120a, TNF-R55 | DRDTVCGCRKNQYRHYWSENLFQCFNCSLCL NGTVHLSCQEKQNTVCTCHAGFFLRENECVSC SNCKKS LECTKLCLP QIENVKGTEDSGTT (SEQ ID NO: 66) |
| TNFRSF1B | tumor necrosis factor receptor superfamily, member 1B | TNFR2 | TNFBR, TNFR80, TNF-R75, TNF-R-II, p75, CD120b | LPAQVAFTPYAPEPGSTCRLREYYDQTAQMCC SKCSPGQHAKVFCTKTSDTVCDSCEDSTYTQL WNWVPECLSCGSRCSSDQVETQACTREQNRIC TCRPGWYCALSKQEGCRLCAPLRKCRPGFGVA RPGTETSDVVCKPCAPGTFSNTTSSTDICRPHQI CNVVAIPGNASMDAVCTSTSPTRSMAPGAVHL PQPVSTRSQHTQPTPEPSTAPSTSFLLPMGPSPP AEGSTGD (SEQ ID NO: 67) |
| TNFRSF4 | tumor necrosis factor receptor superfamily, member 4 | TXGP1L | ACT35, OX40, CD134 | LHCVGDTYPSNDRCCHECRPGNGMVSRCSRSQ NTVCRPCGPGFYNDVVSSKPCKPCTWCNLRSG SERKQLCTATQDTVCRCRAGTQPLDSYKPGVD CAPCPPGHFSPGDNQACKPWTNCTLAGKHTLQ PASNSSDAICEDRDPPATQPQETQGPPARPITVQ PTEAWPRTSQGPSTRPVEVPGGRA (SEQ ID NO: 68) |
| TNFRSF6B | tumor necrosis factor receptor superfamily, member 6b, decoy | | DcR3, DCR3, TR6, M68 | VAETPTYPWRDAETGERLVCAQCPPGTFVQRP CRRDSPTTCGPCPPRHYTQFWNYLERCRYCNV LCGEREEEARACHATHNRACRCRTGFFAHAGF CLEHASCPPGAGVIAPGTPSQNTQCQPCPPGTFS ASSSSSEQCQPHRNCTALGLALNVPGSSSHDTL CTSCTGFPLSTRVPGAEECERAVIDFVAFQDISI KRLQRLLQALEAPEGWGPTPRAGRAALQLKLR RRLTELLGAQDGALLVRLLQALRVARMPGLER SVRERFLPVH (SEQ ID NO: 69) |
| TNFRSF8 | tumor necrosis factor receptor superfamily, member 8 | CD30, D1S166E | KI-1 | FPQDRPFEDTCHGNPSHYYDKAVRRCCYRCPM GLFPTQQCPQRPTDCRKQCEPDYYLDEADRCT ACVTCSRDDLVEKTPCAWNSSRVCECRPGMFC STSAVNSCARCFFHSVCPAGMIVKFPGTAQKNT VCEPASPGVSPACASPENCKEPSSGTIPQAKPTP VSPATSSASTMPVRGGTRLAQEAASKLTRAPDS PSSVGRPSSDPGLSPTQPCPEGSGDCRKQCEPD YYLDEAGRCTACVSCSRDDLVEKTPCAWNSSR TCECRPGMICATSATNSCARCVPYPICAAETVT KPQDMAEKDTTFEAPPLGTQPDCNPTPENGEA PASTSPTQSLLVDSQASKTLPIPTSAPVALSSTG K (SEQ ID NO: 70) |
| TNFRSF9 | tumor necrosis factor receptor superfamily, member 9 | ILA | CD137, 4-1BB | LQDPCSNCPAGTFCDNNRNQICSPCPPNSFSSA GGQRTCDICRQCKGVFRTRKECSSTSNAECDCT PGFHCLGAGCSMCEQDCKQGQELTKKGCKDC CFGTFNDQKRGICRPWTNCSLDGKSVLVNGTK ERDVVCGPSPADLSPGASSVTPPAPAREPGHSP Q (SEQ ID NO: 71) |
| TNFRSF10A | tumor necrosis factor receptor superfamily, member 10a | | DR4, Apo2, TRAILR-1, CD261 | ASGTEAAAATPSKVWGSSAGRIEPRGGGRGAL PTSMGQHGPSARARAGRAPGPRPAREASPRLR VHKTFKFVVVGVLLQVVPSSAATIKLHDQSIGT QQWEHSPLGELCPPGSHRSEHPGACNRCTEGV GYTNASNNLFACLPCTACKSDEEERSPCTTTRN TACQCKPGTFRNDNSAEMCRKCSRGCPRGMV KVKDCTPWSDIECVHKESGNGHN (SEQ ID NO: 72) |
| TNFRSF10B | tumor necrosis factor receptor superfamily, member 10b | | DR5, KILLER, TRICK2A, TRAIL-R2, TRICKB, CD262 | ITQQDLAPQQRAAPQQKRSSPSEGLCPPGHHISE DGRDCISCKYGQDYSTHWNDLLFCLRCTRCDS GEVELSPCTTTRNTVCQCEEGTFREEDSPEMCR KCRTGCPRGMVKVGDCTPWSDIECVHKESGTK HSGEVPAVEETVTSSPGTPASPCS (SEQ ID NO: 73) |
| TNFRSF10C | tumor necrosis factor receptor superfamily, | | DcR1, TRAILR3, LIT, TRID, CD263 | ATTARQEEVPQQTVAPQQRHSFKGEECPAGS HRSEHTGACNPCTEGVDYTNASNNEPSCFPCT VCKSDQKHKSSCTMTRDTVCQCKEGTFRNENS PEMCRKCSRCPSGEVQVSNCTSWDDIQCVEEF GANATVETPAAEETMNTSPGTPAPAAEETMNT |

| Approved Symbol | Approved Name | Previous Symbols | Synonyms | Amino acid sequence of the extracellular domain |
|---|---|---|---|---|
| | member 10c, decoy without an intracellular domain | | | SPGTPAPAAEETMTTSPGTPAPAAEETMTTSPG TPAPAAEETMITSPGTPA (SEQ ID NO: 74) |
| TNFRSF10D | tumor necrosis factor receptor superfamily, member 10d, decoy with truncated death domain | | DcR2, TRUNDD, TRAILR4, CD264 | ATIPRQDEVPQQTVAPQQQRRSLKEEECPAGSH RSEYTGACNPCTEGVDYTIASNNLPSCLLCTVC KSGQTNKSSCTTTRDTVCQCEKGSFQDKNSPE MCRTCRTGCPRGMVKVSNCTPRSDIKCCKNESA ASSTGKTPAAEETVTTILGMLASPYH (SEQ ID NO: 75) |
| TNFRSF11A | tumor necrosis factor receptor superfamily, member 11a, NFKB activator | | RANK, CD265 | IAPPCTSEKHYEHLGRCCNKCEPGKYMSSKCTT TSDSVCLPCGPDEYLDSWNEEDKCLLHKVCDT GKALVAVVAGNSTTPRRCACTAGYHWSQDCE CCRRNTECAPGLGAQHPLQLNKDTVCKPCLAG YFSDAFSSTDKCRPWTNCTFLGKRVEHHGTEK SDAVCSSSLPARKPPNEPHVYLP (SEQ ID NO: 76) |
| TNFRSF11B | tumor necrosis factor receptor superfamily, member11b | OPG | OCIF, TR1 | ETFPPKYLHYDEETSHQLLCDKCPPGTYLKQHC TAKWKTVCAPCPDHYYTDSWHTSDECLYCSP VCKELQYVKQECNRTHNRVCECKEGRYLEIEF CLKHRSCPPGFGVVQAGTPERNTVCKRCPDGF FSNETSSKAPCRKHTNCSVFGLLLTQKGNATH DNICSGNSESTQKCGIDVTLCEEAFFRFAVPTKF TPNWLSVLVDNLPGTKVNAESVERIKRQHSSQ EQTFQLLKLWKHQNKDQDIVKKIIQDIDLCENS VQRHIGHANLTFEQLRSLMESLPGKKVGAEDIE KTIKACKPSDQILKLLSLWRIKNGDQDTLKGLM HALKHSKTYHFPKTVTQSLKKTIRFLHSFTMYK LYQKLFLEMIGNQVQSVKISCL (SEQ ID NO: 77) |
| TNFRSF12A | tumor necrosis factor receptor superfamily, member 12A | | FN14, TweakR, CD266 | EQAPGTAPCSRGSSWSADLDKCMDCASCRARP HSDFCLGCAAAPPAPFRLLWP (SEQ ID NO: 78) |
| TNFRSF13B | tumor necrosis factor receptor superfamily, member 13B | | TACI, CD267 | MSGLGRSRRGGRSRVDQEERFPQGLWTGVAM RSCPEEQYWDPLLGTCMSCKTICNHQSQRTCA AFCRSLSCRKEQGKFYDHLLRDCISCASICGQH PKQCAYFCENKLRSPVNLPPELRRQRSGEVENN SDNSGRYQGLEHRGSEASPALPGLKLSADQVA LVYS (SEQ ID NO: 79) |
| TNFRSF13C | tumor necrosis factor receptor superfamily, member 13C | | BAFFR, CD268 | MRRGPRSLRGRDAPAPTPCVPAECFDLLVRHC VACGLLRTPRPKPAGASSPAPRTALQPQESVGA GAGEAALPLPGLL (SEQ ID NO: 80) |
| TNFRSF14 | tumor necrosis factor receptor superfamily, member 14 | | HVEM, ATAR, TR2, LIGHTR, HVEA, CD270 | LPSCKEDEYPVGSECCPKCSPGYRVKEACGELT GTVCEPCPPGTYIAHLNGLSKCLQCQMCDPAM GLRASRNCSRTENAVCGCSPGHFCIVQDGDHC AACRAYATSSPGQRVQKGGTESQDTLCQNCPP GTFSPNGTLEECQHQTKCSWLVTICAGAGTSSS HWV (SEQ ID NO; 81) |
| TNFRSF17 | tumor necrosis factor receptor superfamily, member 17 | BCMA | BCM, CD269 | MLQMAGQCSQNEYFDSLLHACIPCQLRCSSNT PPLTCQRYCNASVTNSVKGTNA (SEQ ID NO: 82) |
| TNFRSF18 | tumor necrosis factor | | AITR, GITR, CD357 | QRPTGGPGCGPGRLLLGTGTDARCCRVHTTRC CRDYPGEECCSEWDCMCVQPEFHCGDPCCTTC RHHPCPPGQGVQSQGKFSFGFQCIDCASGTFSG |

| Approved Symbol | Approved Name | Previous Symbols | Synonyms | Amino acid sequence of the extracellular domain |
|---|---|---|---|---|
| | receptor superfamily, member 18 | | | GHEGHCKPWTDCTQFGFLTVFPGNKTHNAVC VPGSPPAEP (SEQ ID NO: 83) |
| TNFRSF19 | tumor necrosis factor receptor superfamily, member 19 | | TAJ-alpha, TROY, TAJ, TRADE | ESGDCRQQEFRDRSGNCVPCNQCGPGMELSKE CGFGYGEDAQCVTCRLHRFKEDWGFQKCKPC LDCAVVNRFQKANCSATSDAICGDCLPGFYRK TKLVGFQDMECVPCGDPPPPYEPHCASKVNLV KIASTASSPRDTAL (SEQ ID NO: 84) |
| TNFRSF21 | tumor necrosis factor receptor superfamily, member 21 | | DR6, CD358 | QPEQKASNLIGTYRHVDRATGQVLTCDKCPAG TYVSEHCTNTSLRVCSSCPVGTFTRHENGIEKC HDCSQPCPWPMIEKLPCAALTDRECTCPPGMF QSNATCAPHTVCPVGWGVRKKGTETEDVRCK QCARGTFSDVPSSVMKCKAYTDCLSQNLVVIK PGTKETDNVCGTLPSFSSSTSPSPGTAIFPRPEH METHEVPSSTYVPKGMNSTESNSSASVRPKVLS SIQEGTVPDNTSSARGKEDVNKTLPNLQVVNH QQGPHHRHILKLLPSMEATGGEKSSTPIKGPKR GHPRQNLHKHFDINEH (SEQ ID NO: 85) |
| TNFRSF25 | tumor necrosis factor receptor superfamily, member 25 | TNFRSF12 | DR3, TRAMP, WSL-1, LARD, WSL-LR, DDR3, TR3, APO-3 | QGGTRSPRCDCAGDFHKKIGLFCCRGCPAGHY LKAPCTEPCGNSTCLVCPQDTFLAWENHHNSE CARCQACDEQASQVALENCSAVADTRCGCKP GWFVECQVSQCVSSSPFYCQPCLDCGALHRHT RLLCSRRDTDCGTCLPGFYEHGDGCVSCPTSTL GSCPERCAAVCGWRQ (SEQ ID NO: 86) | b. Single Domain Antibody

Examples of antigen-binding fragments of the antibody include, but are not limited to: (i) a Fab fragment, a monovalent fragment consisting of the $V_L$, $V_H$, $C_L$, and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody; (v) a dAb fragment (Ward et al., (1989) Nature 341:544-546), which consists of a $V_H$ domain; (vi) an isolated complementarity determining region (CDR); and (vii) $V_L$ or $V_H$ domains. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to than monovalent molecules (known as single-chain Fv (scFv); see e.g., Bird et al. (1988) Science 242:423-426; and Huston et al. (1988) Proc. Natl. Acad. Sci. USA 85:5879-5883). Such single-chain antibodies are also encompassed within the term "antigen-binding fragment" of an antibody. These antibody fragments can be obtained using conventional techniques known to those with skill in the art, and the fragments are screened for utility in the same manner as are intact antibodies.

An antibody can be a monoclonal antibody. In one embodiment, the antibody can be recombinantly produced, e.g., produced by phage display or by combinatorial methods. Phage display and combinatorial methods for generating antibodies are known in the art (see e.g., Ladner et al. U.S. Pat. No. 5,223,409; Kang et al. International Publication No. WO 92/18619; Dower et al. International Publication No. 25 WO 91/17271; Winter et al. International Publication WO 92/20791; Markland et al. International Publication No. WO 92/15679; Breitling et al. International Publication WO 93/01288; McCafferty et al, International Publication No. WO 92/01047; Garrard et al. International Publication No. WO 92/09690; Ladner et al. International Publication No. WO 90/02809; Fuchs et al. (1991) Bio/Technology 9: 1370-1372; Hay et al. (1992) Hum Antibod Hybridomas 3: 81-85; Huse et al. (1989) Science 246: 1275-1281; Griffths et al. (1993) EMBO 12: 725-734; Hawkins et al. (1992) J Mol Biol 226: 889-896; Clackson et al. (1991) Nature 352: 624-628; Gram et al. (1992) Proc Natl Acad Sci USA 89: 3576-3580; Garrad et al. (1991) Bio/Technology 9: 1373-1377; Hoogenboom et al. (1991) Nuc Acid Res 19: 41334137; and Barbas et al. (1991) Proc Natl Acad Sci USA 88: 7978-7982, the contents of all of which are incorporated by reference herein).

In one embodiment, the antibody is a fully human antibody (e.g., an antibody made in a mouse which has been genetically engineered to produce an antibody from a human immunoglobulin sequence), or a non-human antibody, e.g., a rodent (mouse or rat), goat, primate (e.g., monkey), or camel antibody. Preferably, the non-human antibody is a rodent (mouse or rat antibody), Methods of producing rodent antibodies are known in the art.

Human monoclonal antibodies can be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT 15 publication WO 91/10741; Lonberg et al. International Application WO 92/03918; Kay et al. International Application 92/03917; Lonberg, et al. (1994) Nature 368: 856-859; Green, L. L. et al. (1994) Nature Genet. 7: 13-21; Morrison et al. (1994) Proc. Natl. Acad. Sci. USA 81: 6851-6855; Bruggeman et al. (1993)Year Immunol 7: 33-40; Tuaillon et al, (1993) Proc. Natl. Acad. Sci, USA 90: 3720-3724; Bruggeman et al. (1991) Eur J Immunol 21: 1323-1326).

An antibody can be one in which the variable region, or a portion thereof, e.g., the CDR's, are generated in a non-human organism, e.g., a rat or mouse. Chimeric, CDR-grafted, and humanized antibodies can be used. Antibodies generated in a non-human organism, e.g., a rat or mouse, and then modified, e.g., in the variable framework or constant region, to decrease antigenicity in a human are within the invention.

Chimeric antibodies can be produced by recombinant DNA techniques known in the art. For example, a gene encoding the Fc constant region of a murine (or other species) monoclonal antibody molecule is digested with restriction enzymes to remove the region encoding the murine Fc, and the equivalent portion of a gene encoding a human Fc constant region is substituted (see Robinson et al., International Patent Publication PCT/US86/02269; Akira, et al., European Patent Application 184, 187; Taniguchi, M., European Patent Application 171,496; Morrison et al., European Patent Application 173,494; Neuberger et al., International Application WO 86/01533; Cabilly et al. U.S. Pat. No. 4,816,567; Cabilly et al., European Patent Application 125,023; Better et al. (1988) Science 240: 1041-1043; Liu et al. (1987) Proc. Natl. Acad. Sci. USA 84: 3439-3443; Liu et al., (1987) J. Immunol. 139:3521-3526; Sun et al. (1987) Proc. Natl. Acad. Sci. USA 84: 214-218; Nishimura et al., (1987) Canc. Res. 47: 999-1005; Wood et al. et al (1985) Nature 314: 446-449; and Shaw et al., (1988) J. Natl Cancer Inst. 80: 1553-1559).

A humanized or CDR-grafted antibody will have at least one or two but generally all three recipient CDR's (of heavy and/or light immunoglobulin chains) replaced with a donor CDR. The antibody may be replaced with at least a portion of a non-human CDR or only some of the CDR's may be replaced with non-human CDR's. It is only necessary to replace the number of CDR's required for binding of the humanized antibody or a fragment thereof. Preferably, the donor will be a rodent antibody, e.g., a rat or mouse antibody, and the recipient will be a human framework or a human consensus framework. Typically, the immunoglobulin providing the CDR's is called the "donor" and the immunoglobulin providing the framework is called the "acceptor." In one embodiment, the donor immunoglobulin is a non-human (e.g., rodent). The acceptor framework is a naturally-occurring (e.g., a human) framework or a consensus framework, or a sequence about 85% or higher, preferably 90%, 95%, 99% or higher identical thereto.

In one embodiment the antigen binding region is the $V_H$ of anti-β-galactosidase. In one embodiment, the antigen binding region has the sequence of:

(SEQ ID NO: 19)
GluProLysSerGlyAspLysThrHisThrCysProProCysPro or (SEQ ID NO: 20)
GluProLysSerCysAspLysThrHisThrCysProProCysPro or one of the following:

| Amino acid sequences of the hinge region of human Immuno globulins | | |
|---|---|---|
| SEQ ID NO: 46 | Human IgG$_1$ | EPKSCDKTHTCPPCPAPELLGGP |
| SEQ ID NO: 47 | Human IgG$_2$ | ERKCCVECPPCPAPPVAGP |
| SEQ ID NO: 48 | Human IgG$_3$ | ELKTPLGDTTHTCPRCPAPELLGGP |
| SEQ ID NO: 49 | Human IgG$_4$ | ESKYGPPCPSCPAPEFLGGP |

In one embodiment, the "hinge region" comprises a glycine linker.

Examples of a Glycine Linker (G-linker) may include the following:

(GGGGS)$_3$ (SEQ ID NO: 51) The most commonly used linker of scFv contains a fifteen combination of glycine and serine residues.

GGSGGSGGGGSGGGGS (SEQ ID NO: 52), as shown in U.S. Pat. No. 5,908,626: Hybrid with interferon-β and an immunoglobulin Fc joined by a peptide linker.

RGRGRGRGRGRGGGS: (SEQ ID NO: 54) taken from scFv-RG3.

Generally, the sequence of the "hinge region" or glycine linker may have 1, 2, 3, 4, 5, 6, or 7, amino acid additions, deletions or substitutions, which do not materially affect the basic and novel characteristics of the invention, that is so long as they does not prevent the assembly or maintenance of a trimer or hexamer structure.

The "hinge region" or glycine linker is optional, and, even if present need not have a trimerizing effect on the claimed fusion peptides. However, it may also be designed to assist or emphasize the trimerizing tendencies of the collagen-like domain.

(SEQ ID NO: 17)

AspAlaAlaGlnProAlaArgArgAlaGlnValGlnLeuLeuGluSerGlyGlyGlyLeuValGlnProGlyGlySerLeu

ArgLeuSerCysAlaAlaSerGlyValSerIleThrAlaGluSerMetSerTrpValArgGlnAlaProGlyLysGlyLeu

GluTrpValSerThrIleThrMetArgAspGlySerThrTyrTyrAlaAspSerValLysGlyArgPheThrIleSerArg

AspAsnSerLysAsnThrLeuTyrLeuGlnMetAsnSerLeuArgAlaGluAspThrAlaValTyrTyrCysAlaArgAla

ArgAlaMetTyrProLeuArgSerSerGlnLeuGluSerTrpGlyGlnGlyThrLeuValThrValSerSer

B. Hinge Region or Glycine Linker

The fusion proteins of the present invention may include a "hinge region." In one embodiment, the hinge region is an approximately 4-15 amino acid long sequence. It may be the hinge region of a human IgG or a glycine linker. In one embodiment, the hinge region of a human IgG is the hinge region of human IgG$_1$ or human IgG$_2$.

In one embodiment, the "hinge region" has one of the following sequences:

C. Collagen-Like Domain
a. Basic Structure

As used herein the "collagen-like domain" may include the sequence of (G-P-X), more specifically (G-P-X1), where glycine (G), proline (P), X1 may be P or hydroxyproline (O). The general sequence (G-P-X) or amino acid "block" may be repeated from 4 to 150 times, with each repeat independently defining the X amino acids.

However, as discussed above there are concerns that an extended crosslinked G-P-O (specifically, where X1 is hydroxylated) triplet may contribute to platelet aggregation in vivo. Therefore, it is preferred that the G-P-O block not be repeated more than 15 times in sequence. That said, a G-P-O repeated block which is repeated 7 times, interrupted by a short imperfection or a trimer-stabilizing sequence joined to a G-P-O block repeated 8 times may not trigger such platelet activation.

The collagen-like domain can also include a perfect repeating G-P-P or G-P-O triplet, interrupted by a short imperfection, in which the first position of G or the third position P or O residue is missing, found in many naturally occurring collagens and proteins containing collagen-like domains. For example, human type XXI minicollagen, contains two imperfections, GF and KE, within the collagenous domain. Incorporating these types of "imperfections" does not materially affect the basic and novel characteristics of the invention so long as it does not prevent the assembly or maintenance of a trimer or hexamer structure.

When the (G-P-X) block incorporates "imperfections," the block might have a structure of (G-P-X1-X2-X3), where X1 may be P or O, where X2 may be independently present or absent, and if present is G, P, O, or K, and X3 is independently present or absent, and is independently G, P, O, E or F, with the proviso that if both are present only one of X2 and X3 may be G. Positions X2 and X3 arise out of "imperfections" that occur in natural collagenous domains, where either the first or the third amino acid of the G-P-P or G-P-O is absent or where alternate amino acids are incorporated into the collagen structure, such as the GF and KE imperfections found in human type XXI minicollagen. For instance a repeat of 10 of the blocks might look like:
(G-P-X1-X2-X3)(G-P-X4-X5-X6)(G-P-X7-X8-X9)(G-P-X10-X1'-X12)(G-P-X13-X14-X15)(G-P-X16-X17-X18)
(G-P-X19-X20-X21)(G-P-X22-X23-X24)(G-P-X25-X26-X27)(G-P-X28-X29-X30),
where X1, X4, X7, X10, X13, X16, X19, X22, X25, and X28 are each independently P or O; X2, X5, X8, X11, X14, X17, X20, X23, X26, and X29 are each independently present or absent, and if present is G, P, O, or K; and X3, X6, X9, X12, X15, X18, X21, X24, X27, and X30 are each independently present or absent, and if present, is independently G, P, O, E or F, with the proviso that if present, the second to last amino acid in the block and the last amino acid in the block are not both Gs, e.g., if all are present, then X2 and X3 are not both Gs, X5 and X6 are not both Gs, X8 and X9 are not both Gs, X11 and X12 are not both Gs, X14 and X15 are not both Gs, X17 and X18 are not both Gs, X20 and X21 are not both Gs, X23 and X24 are not both Gs, X26 and X27 are not both Gs, and X29 and X30 are not both Gs.

In one embodiment, the collagen-like domain comprises 10 (G-P-X1) blocks. In certain embodiments, the collagen-like domain comprises less than 5, 7, 8, 9, 10, 11, 12, 13, 14, 15, 16, 17, 18, 19, 20, 22, 25, 27, 30, 35, 40, 45, or 50 (G-P-X1) blocks. In certain embodiments, the collagen-like domain is less than 150, 125, 100, 90, 80, 70, 60, 50, or 40 amino acids in length. In one embodiment, the collagen-like domain consists essentially of 4-10 (G-P-X1) blocks, which promote self-trimerization. In one embodiment, the collagen like domain consists essentially of 10 (G-P-X1) blocks in a single amino acid sequence.

In one embodiment, a thermally stable short sequence of amino acids, such as (Gly-Pro-Pro)$_{10}$ (SEQ ID NO: 21) or (Gly-Pro-Hyp)$_{10}$ (SEQ ID NO: 33) is used as a collagen-like domain to drive the trimerization of the TNF receptor domain and/or the Fc domain by expressing the fusion construct in a system. This approach facilitates the adoption of the stable triple-helical structure, which affects protein valency, stability, and function in vivo. To obtain Gly-Pro-Hyp expression, prolines specified in the X1 position of Gly-P-X1 motif of collagen are generally post-translationally modified to 4-hydroxyproline by prolyl 4-hydroxylase (P4H) to stabilize the triple-helical structure of collagen. Prokaryotes and certain other expression systems (yeasts and insects) do not have the appropriate enzyme activity to modify the proline to hydroxyproline. Thus, methods have previously been found to obtain the appropriate post-translational modification to obtain the hydroxyproline in the collagen-like domain sequence.

Consequently for the purposes herein, a sequence recited as "G-P-P" represents an amino acid sequence encoded by a nucleotide sequence for "G-P-P" but which may be post-translationally modified to have the structure of "G-P-O." Thus, the structure "G-P-O" may be recited as either "G-P-P" or "G-P-O".

Percentage of Hydroxyproline

Some percentage of the total number of proline residues in the X1 position of the G-P-X1 or G-P-X1-X2-X3 block may be hydroxylated. The X3 position may also be hydroxylated. Additionally expression can be performed in Chinese hamster ovary (CHO) cells. For instance, when the trimeric soluble fusion protein comprises three polypeptides, and each polypeptide has a collagen-like domain that includes at least 10 G-P-X1 repeats, and wherein at least 5, at least 6, at least 7, at least 8, at least 9, or at least 10 of the X1 residues are hydroxyproline. Thus, the percentage of hydroxylation of the prolines is generally at least 50%, 60%, 70%, 80%, 90% or all of the prolines (e.g., any number between 50% and 100%, inclusive).

The self-trimerization of the collagen-like domain of the invention allows attachment of fusion partners to either terminus, as well as to both termini, simultaneously. This has important consequences as the self-trimerization of the fusion proteins may be employed to construct molecules that are able to interact (each end with a binding valency up to 3 or 6) simultaneously with multiple bulky binding partners. The present invention also demonstrates that the trimeric or hexameric fusion proteins can fold correctly and exhibit high solubility, avidity, and stability.

b. Trimerizing Motif

A sequence which promotes trimerization, oligomerization or stabilization of trimer/hexamer structure can be added to the fusion proteins to promote the association of the present fusion proteins into trimer or hexamer structures. In particular the trimerizing motif, which may include a ""GXKGE(D)" motif" (SEQ ID NO: 34) or variations thereof, which can be placed adjacent to, or inserted in between the blocks G-P-X1 of the collagen domain to promote the association of monomer polypeptides into the present fusion protein.

An interchain disulfide-bonded (Gly-Pro-Pro)$_{10}$ triplex has been explored in the context of (G-P-P)$_{10}$ trimers. This interchain disulfide bond was obtained in vitro by a redox-shuffling process of a disulfide knot of type III collagen either C- or N-terminal adjacent to the collagen-like peptide at 20° C. (Boudko et al., (2002) J Mol Biol 317: 459-470; Frank et al., (2003) J Biol Chem 278: 7747-7750). A disulfide knot or disulfide bond may be also component of a trimerizing motif.

In one embodiment, this trimerizing motif includes a "GXKGE(D) motif" (SEQ ID NO: 34) that is inserted into the collagen-like domain, or may be placed at either end of the collagen-like domain to improve self-trimerization of the present fusion proteins. In one embodiment, the GXKGED motif (SEQ ID NO: 34) or variations thereof are inserted in between blocks of the collagen-like domain. In one embodiment there are six blocks of (G-P-X1), the trimerizing motif, and six blocks of (G-P-X1). For the trimerizing motif, which includes variations on the GXKGE(D) (SEQ ID NO: 34) motif, sequences may be:

RDGTPGEKGEKGDXGLXG-PGEXGXXGXXGXEGPRGFPGXXGRKGE, where X is any amino acid, and each K is glycosylated (SEQ ID NO: 55) (e.g., the collagenous domain of adiponectin, which is conserved between mouse, human, bovine, monkey and dog species).

More specifically, the trimerizing motifs include: GEKGEKGD (SEQ ID NO: 56), GPGE (SEQ ID NO: 57), and/or GRKGE (SEQ ID NO: 58), wherein each lysine is hydroxylated and subsequently glycosylated.

In one embodiment, the collagenous domain including the trimerizing motif having variations on a GXKGE(D) (SEQ ID NO: 34) motif has the following sequence:

(SEQ ID NO: 25)
GPPGPPGPPGPPGTKGEKGEPGQGLRGLQGPQGEKGDRGLTGQTGPPG

APGIRGIPGVKGDRGQIGFPGGRGNPGAPGKPGRSGSPGPKGQKGEKG

SVGPPGPPGPPGPPGPCCGGTG.

In one embodiment, the collagenous binding domain including the GXKGE(D) (SEQ ID NO: 34) motif has one of the following sequences:

(SEQ ID NO: 23)
(GPP)$_4$-GEKGEKGDPGPKGDI-(GPP)$_4$, (SEQ ID NO: 24)
(GPP)$_5$-GEKGEKGDPGPKGDI-(GPP)$_4$, (SEQ ID NO: 35)
(GPP)$_6$-GEKGEKGDPGPKGDI-(GPP)$_6$.

The trimerizing motif described above or the "GXKGE(D) motif" (SEQ ID NO: 34) itself may include amino acid additions, so long as they do not prevent the trimerization of the collagen-like domain or the trimerization or hexamerization of the present fusion proteins.

D. Fc Domain

The present fusion protein includes a heavy and/or light chain constant region, e.g., the Fc region, to thereby form a heavy and/or light immunoglobulin chain, respectively. When the Fc domain is included in the present fusion proteins, it promotes dimerization of the fusion proteins, or, acting in concert with the trimerizing collagen-like domain, can promote hexamerization; associating proteins that are a dimer of a trimeric structure or a trimer of a dimeric structure. In one embodiment, the collagen-like domain trimerization tendency is enhanced with one or more oligomerizing domains to form trimer structures, and the competing dimerization force from the Fc domain assists with producing a dimer of a trimeric fusion protein, where each trimer's collagen-like domains form a triple-helix coiled structure.

The heavy chain constant region is comprised of three domains, CH1, CH2, and CH3. In one embodiment the Fc domain of human IgG1 includes the CH2 and CH3 domain of human IgG1. In one embodiment, the CH2 and CH3 domain is 210 amino acids long.

The Fc domain of the present fusion polypeptide monomers may have one of the following sequences:
Version 1:

(SEQ ID NO: 27)
ProSerValPheLeuPheProProLysProLysAspThrLeuMetIleSerArgThrProGluValThrCysValValVal

AspValSerHisGluAspProGluValLysPheAsnTrpTyrValAspGlyValGluValHisAsnAlaLysThrLysPro

ArgGluGluGlnTyrAsnSerThrTyrArgValValSerValLeuThrValLeuHisGlnAspTrpLeuAsnGlyLysGlu

TyrLysCysLysValSerAsnLysAlaLeuProAlaProIleGluLysThrIleSerLysAlaLysGlyGlnProArgGluPro

GlnValTyrThrLeuProProSerArgAspGluLeuThrLysAsnGlnValSerLeuThrCysLeuValLysGlyPheTyr

ProSerAspIleAlaValGluTrpGluSerAsnGlyGlnProGluAsnAsnTyrLysThrThrProProValLeuAspSer

AspGlySerPhePheLeuTyrSerLysLeuThrValAspLysSerArgTrpGlnGlnGlyAsnValPheSerCysSerVal

MetHisGluAlaLeuHisAsnHisTyrThrGlnLysSerLeuSerLeuSerProGlyLys

Version 2:

(SEQ ID NO: 28)
ProSerValPheLeuPheProProLysProLysAspThrLeuMetIleSerArgThrProGluValThrCysValValVal

AspValSerHisGluAspProGluValLysPheAsnTrpTyrValAspGlyValGluValHisAsnAlaLysThrLysPro

ArgGluGluGlnTyrAsnSerThrTyrArgValValSerValLeuThrValLeuHisGlnAspTrpLeuAsnGlyLysGlu

TyrLysCysLysValSerAsnLysAlaLeuProAlaProIleGluLysThrIleSerLysAlaLysGlyGlnProArgGluPro

GlnValTyrThrLeuProProSerArgAspGluLeuThrLysAsnGlnValSerLeuThrCysLeuValLysGlyPheTyr

ProSerAspIleAlaValGluTrpGluSerAsnGlyGlnProGluAsnAsnTyrLysThrThrProProValLeuAspSer

-continued

AspGlySerPhePheLeuTyrSerLysLeuThrValAspLysSerArgTrpGlnGlnGlyAsnValPheSerCysSerVal

MetHisGluAlaLeuHisAsnHisTyrThrGlnLysSerLeuSerLeuSerProGlyLys

Version 3:

(SEQ ID NO: 29)
ProSerValPheLeuPheProProLysProLysAspThrLeuMetIleSerArgThrProGluValThrCysValValVal

AspValSerHisGluAspProGluValLysPheAsnTrpTyrValAspGlyValGluValHisAsnAlaLysThrLysPro

ArgGluGluGlnTyrAsnSerThrTyrArgValValSerValLeuThrValLeuHisGlnAspTrpLeuAsnGlyLysGlu

TyrLysCysLysValSerAsnLysAlaLeuProAlaProIleGluLysThrIleSerLysAlaLysGlyGlnProArgGluPro

GlnValTyrThrLeuProProSerArgAspGluLeuThrLysAsnGlnValSerLeuThrCysLeuValLysGlyPheTyr

ProSerAspIleAlaValGluTrpGluSerAsnGlyGlnProGluAsnAsnTyrLysThrThrProProValLeuAspSer

AspGlySerPhePheLeuTyrSerLysLeuThrValAspLysSerArgTrpGlnGlnGlyAsnValPheSerCysSerVal

MetHisGluAlaLeuHisAsnHisTyrThrGlnLysSerLeuSerLeuSerProGlyLys

Version 4:

(SEQ ID NO: 30)
ProSerValPheLeuPheProProLysProLysAspThrLeuMetIleSerArgThrProGluValThrCysValValVal

AspValSerHisGluAspProGluValLysPheAsnTrpTyrValAspGlyValGluValHisAsnAlaLysThrLysPro

ArgGluGluGlnTyrAsnSerThrTyrArgValValSerValLeuThrValLeuHisGlnAspTrpLeuAsnGlyLysGlu

TyrLysCysLysValSerAsnLysAlaLeuProAlaProIleGluLysThrIleSerLysAlaLysGlyGlnProArgGluPro

GlnValTyrThrLeuProProSerArgAspGluLeuThrLysAsnGlnValSerLeuThrCysLeuValLysGlyPheTyr

ProSerAspIleAlaValGluTrpGluSerAsnGlyGlnProGluAsnAsnTyrLysThrThrProProValLeuAspSer

AspGlySerPhePheLeuTyrSerLysLeuThrValAspLysSerArgTrpGlnGlnGlyAsnValPheSerCysSerVal

MetHisGluAlaLeuHisAsnHisTyrThrGlnLysSerLeuSerLeuSerProGlyLys

Version 5:

(SEQ ID NO: 31)
ProSerValPheLeuPheProProLysProLysAspThrLeuMetIleSerArgThrProGluValThrCysValValVal

AspValSerHisGluAspProGluValLysPheAsnTrpTyrValAspGlyValGluValHisAsnAlaLysThrLysPro

ArgGluGluGlnTyrAsnSerThrTyrArgValValSerValLeuThrValLeuHisGlnAspTrpLeuAsnGlyLysGlu

TyrLysCysLysValSerAsnLysAlaLeuProAlaProIleGluLysThrIleSerLysAlaLysGlyGlnProArgGluPro

GlnValTyrThrLeuProProSerArgAspGluLeuThrLysAsnGlnValSerLeuThrCysLeuValLysGlyPheTyr

ProSerAspIleAlaValGluTrpGluSerAsnGlyGlnProGluAsnAsnTyrLysThrThrProProValLeuAspSer

AspGlySerPhePheLeuTyrSerLysLeuThrValAspLysSerArgTrpGlnGlnGlyAsnValPheSerCysSerVal

MetHisGluAlaLeuHisAsnHisTyrThrGlnLysSerLeuSerLeuSerProGlyLys

The Fc domain may have amino acid additions, deletions or substitutions, which do not materially affect the basic and novel characteristics of the invention, that is so long as they does not prevent the assembly or maintenance of a trimer or hexamer structure.

In one embodiment, the Fc domain sequence is a mutated CH2 and CH3 domain where one or more amino acids have been added, deleted or substituted from the non-mutated sequence. Preferably, the mutated sequence has at least 70%, (e.g., any number between 70% and 100%, inclusive) sequence homology at either the nucleotide or the amino acid level to one of the enumerated Fc domain sequences above. In one embodiment the mutated sequence has at least 90, 92, 95, 97, or 99% sequence homology at either the nucleotide or the amino acid level to one of the enumerated Fc domain sequences above.

In one embodiment the mutated Fc domain is a CH2 and CH3 sequence which has a mutation at one or more of amino acid residues 366, 368, or 407 of the human IgG1 Fc domain. In one embodiment the Fc domain has one or more of the following mutations: T366S:L368A:Y407V. In a preferred embodiment, the Fc domain has the following sequence:

(SEQ ID NO: 32)
ProSerValPheLeuPheProProLysProLysAspThrLeuMetIleSerArgThrProGluValThrCysValValValAsp

ValSerHisGluAspProGluValLysPheAsnTrpTyrValAspGlyValGluValHisAsnAlaLysThrLysProArgGlu

GluGlnTyrAsnSerThrTyrArgValValSerValLeuThrValLeuHisGlnAspTrpLeuAsnGlyLysGluTyrLys

CysLysValSerAsnLysAlaLeuProAlaProIleGluLysThrIleSerLysAlaLysGlyGlnProArgGluProGlnVal

TyrThrLeuProProSerArgAspGluLeuThrLysAsnGlnValSerLeuSerCysAlaValLysGlyPheTyrProSer

AspIleAlaValGluTrpGluSerAsnGlyGlnProGluAsnAsnTyrLysThrThrProProValLeuAspSerAspGlySer

PhePheLeuValSerLysLeuThrValAspLysSerArgTrpGlnGlnGlyAsnValPheSerCysSerValMetHisGluAla

LeuHisAsnHisTyrThrGlnLysSerLeuSerLeuSerProGlyLys.

E. Linker

The linker is a short peptide sequence which may be placed in between the Fc domain and the collagen-like domain or between the binding domain and the collagen-like domain. Preferably the linker is between 4 and 10 amino acids in length, and may have the sequence:

(SEQ ID NO: 18)
Alaalaalaglyglyglyglyglyser or (SEQ ID NO: 50)
glyglyglyglyser.

The linker may also be a glycine linker. Examples of a glycine linker suitable for using as a linker are as follows:

(GGGGS)$_3$ (SEQ ID NO: 51), is the most commonly used linker of scFv contains a fifteen combination of glycine and serine residues.

GGSGGSGGGGSGGGGS (SEQ ID NO: 52) U.S. Pat. No. 5,908,626: Hybrid with interferon-β and an immunoglobulin Fc joined by a peptide linker.

Glycine-alanine linker: GGAGAGAG (SEQ ID NO: 53).

Glycine-arginine linker: RGRGRGRGRGRGGGS (SEQ ID NO: 54).

The linker may have amino acid additions, deletions or substitutions, which do not materially affect the basic and novel characteristics of the invention, that is so long as they do not prevent the assembly or maintenance of a trimer or hexamer structure. Preferably, the linker may have 1, 2, or 3 amino acid additions, deletions or substitutions.

In a embodiment, the trimeric or hexameric fusion protein is a soluble protein. A soluble protein is one that is soluble under physiological conditions. In a embodiment, the soluble fusion protein is a secreted protein. A secreted fusion protein is one that is secreted by a cell. Secretion of a protein can be targeted by having a signal sequence on the polypeptide comprising the antibody domain.

Signal sequences may include:

(SEQ ID NO: 15)
MetGluThrAspThrLeuLeuLeuTrpValLeuLeuLeuTrpValPro

GlySerThrGly.

In the expressed and secreted protein the signal sequence is cleaved off. Thus, it is clear to one of skill in the art that the nucleotide sequences encoding the present fusion proteins may include a sequence coding for the signal sequence or not, depending on how the fusion protein is expected to be expressed.

The embodiments of invention also includes a nucleic acid which encodes a fusion polypeptide that forms a protein complex of this invention. The nucleic acid can be screened from phage display library or isolated (e.g., by RT-PCR) from cell lines expressing the above-described suitable antibodies or antibody derivatives. The nucleic acid can be functionally ligated into an expression vector. Cells transformed with the nucleic acid or vector can be used to produce the fusion polypeptide or protein complex of this invention. Cells useful for producing an antibody include insect cells and mammalian cells. These cells include, but are not limited to: myeloma NS0 cells, CHO cells, and lymphatic cells.

In one embodiment, the invention encompasses a method for generating a trimeric or hexameric soluble fusion protein by joining a nucleic acid encoding a collagen-like domain in-frame with a nucleic acid encoding a binding domain. In a preferred embodiment, the collagen-like domain comprises more than 10 G-P-X1 repeats. In one embodiment, the collagen-like domain comprises 10-30 G-P-X1 repeats; wherein G is glycine, P is proline, and X1 is P or O, and wherein at least 10 of the G-P-X1 repeats are G-P-P. In one embodiment, the collagen-like domain is joined in-frame with a nucleic acid encoding a binding domain for a ligand; and expressing the encoded polypeptide in a cell that hydroxyprolinates at least 5, at least 6, at least 7, at least 8, at least 9, or at least 10 of the G-P-P repeats at the X1 position; wherein the hydroxyprolinated collagen-like domains of three polypeptides interact with each other to form a trimeric soluble antibody that specifically binds to the ligand with a functional affinity of at least $10^{-7}$ M.

In one embodiment, the ligand for the trimeric soluble fusion protein is a TNF family protein. In one embodiment, the ligand for the trimeric soluble fusion protein is TNFα.

Collagen-like domains and the present fusion proteins can be expressed from vectors, preferably expression vectors, containing a nucleic acid encoding a polypeptide of the invention. As used herein, the term "vector" refers to a nucleic acid molecule capable of transporting another nucleic acid to which it has been linked and can include a plasmid, cosmid, or viral vector. The vector can be capable of autonomous replication or it can integrate into a host DNA. Viral vectors include, e.g., replication defective retroviruses, adenoviruses, and adeno-associated viruses. Expression of proteins in prokaryotes is most often carried out in E. coli with vectors containing constitutive or inducible promoters directing the expression of either fusion or non-fusion proteins.

Fusion vectors can add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin, and enterokinase.

To maximize recombinant protein expression in E. coli is to express the protein in a host bacteria with an impaired capacity to proteolytically cleave the recombinant protein (Gottesman, S., (1990) Gene Expression Technology: Methods in Enzymology 185, Academic Press, San Diego, Calif. 119 128). Another strategy is to alter the nucleic acid sequence of the nucleic acid to be inserted into an expression vector so that the individual codons for each amino acid are those preferentially utilized in E. coli (Wada et al., (1992) Nucleic Acids Res. 20: 2111 2118). Such alteration of nucleic acid sequences of the invention can be carried out by standard DNA synthesis techniques.

A host cell can be any prokaryotic or eukaryotic cell. The proteins of the invention can be expressed in bacterial cells (such as E. coli), insect cells, yeast, or mammalian cells (such as Chinese hamster ovary cells (CHO), COS cells (African green monkey kidney cells CV-1 origin SV40 cells; Gluzman (1981) Cell 23:175 182)), or NS0 cells. Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

The embodiments of invention encompasses a method for inhibiting the biological activity of a ligand comprising incubating a trimeric fusion polypeptide complex with a ligand; wherein the binding of the trimeric fusion polypeptide complex to the ligand inhibits the biological activity of the ligand.

In one embodiment, the soluble fusion protein has a functional affinity for its ligand of greater than $10^{-6}$ M. In one embodiment, the soluble fusion protein has a functional affinity for its ligand of greater than $10^{-8}$ M. In one embodiment, the soluble fusion protein has functional affinity for its ligand of greater than $10^{-10}$ M. In certain embodiments, the soluble trimeric fusion protein has a functional affinity for its ligand between $10^{-7}$ M and $10^{-12}$ M, between $10^{-8}$ M and $10^{-11}$ M, between $10^{-7}$ M and $10^{-10}$ M, between $10^{-8}$ M and $10^{-10}$ M, and between $10^{-9}$ M and $10^{-10}$ M.

In certain embodiments, the ligand for the trimeric soluble fusion protein is a human TNF family protein, preferably human TNFα.

A protein complex of the embodiments of the invention may be conjugated to a therapeutic moiety such as a cytotoxin, a therapeutic agent, or a radioactive ion. A cytotoxin or cytotoxic agent includes any agent that is detrimental to cells. Examples include taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, puromycin, maytansinoids, e.g., maytansinol (see U.S. Pat. No. 5,208,020), CC-1065 (see U.S. Pat. Nos. 5,475,092, 5,585,499, and 5,846,545) and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, CC-1065, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine, vinblastine, taxol and maytansinoids).

Radioactive ions contemplated in embodiments of the invention include, but are not limited to, $^{111}$Indium, $^{113}$Indium, $^{99}$Rhenium, $^{105}$Rhenium, $^{101}$Rhenium, $^{99}$Mtechnetium, $^{121}$Mtellurium, $^{122}$Mtellurium, $^{125}$Mtelluriunm, $^{165}$Thulium, $^{167}$Thulium, $^{168}$Thulium, $^{123}$Iodine, $^{125}$Iodine, $^{126}$Iodine, $^{131}$Iodine, $^{133}$Iodine, $^{81}$Krypton, $^{33}$Xenon, $^{90}$Yttrium, $^{213}$Bismuth, $^{77}$Bromine, $^{18}$Fluorine, $^{95}$Ruthenium, $^{97}$Ruthenium, $^{103}$Ruthenium, $^{105}$Ruthenium, $^{107}$Mercury, $^{203}$Mercury, $^{67}$Gallium, $^{68}$Gallium, $^{35}$Sulphur, and $^{14}$Carbon.

The conjugates can be used for modifying a given biological response by administering the conjugate to a host. The drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, β-interferon, nerve growth factor, platelet derived growth factor, tissue plasminogen activator; or, biological response modifiers such as, for example, lymphokines, interleukin-1 ("IL-1"), interleukin-2 ("IL-2"), interleukin-6 ("IL-6"), granulocyte macrophase colony stimulating factor ("GM-CSF"), granulocyte colony stimulating factor ("G-CSF"), or other growth factors.

In further embodiments of the invention, a fusion protein can be conjugated to a polymer. Such polymers include, but are not limited to polyethylene glycol, polypropylene glycol, and polyoxyethylated polyol.

The above-described protein complexes and conjugates, based on the specificity of the heterologous binding domains, can be used for treating various disorders, including cancers, inflammation diseases, metabolism diseases, fibrosis diseases, and cardiovascular diseases. The invention therefore features a method of treating such a disorder, e.g., by administering to a subject in need thereof an effective amount of a protein complex of the invention to treat the disorder. Subjects to be treated can be identified as having, or being at risk for acquiring, a condition characterized by the disorder. This method can be performed alone or in conjunction with other drugs or therapy. In a preferred embodiment, the present invention is used for treating disorders caused by or exacerbated by the presence of TNFα. In another embodiment, the present invention is used for modulating the biological activity of TNFα, modulating the level of TNFα signaling, or modulating the amount of unbound TNFα in a patient in need thereof. In a preferred embodiment, the present invention decreases the level of unbound TNFα or TNFα signaling.

Because of the multi-specific feature of a protein complex of this invention, one can use it to bridge molecules or cells that are normally are not associated with each other. This feature is particularly useful for cell-based therapies. In one example, one heterologous domain in the protein complex is capable of binding the neonatal Fc receptor (FcRn) which is present on endothelial cells, while another heterologous domain specifically binds to TNFα, permitting the protection of the present fusion proteins from degradation, and keeping the molecule in circulation longer. In this way, the protein complex can treat a disorder caused by or exacerbated by high levels of TNFα.

The term "treating" is defined as administration of a composition to a subject with the purpose to cure, alleviate, relieve, remedy, prevent, or ameliorate a disorder, the symptom of the disorder, the disease state secondary to the disorder, a disorder which is exacerbated by the ligand of the present protein, or the predisposition toward the disorder. An "effective amount" is an amount of the composition that is capable of producing a medically desirable result, e.g., as described above, in a treated subject.

In one in vivo approach, a therapeutic composition (e.g., a composition containing a protein complex the invention) is administered to a subject. Generally, the complex is suspended in a pharmaceutically-acceptable carrier (e.g., physiological saline) and administered orally or by intravenous infusion, or injected or implanted subcutaneously, intramuscularly, intrathecally, intraperitoneally, intrarectally, intravaginally, intranasally, intragastrically, intratracheally, or intrapulmonarily.

The dosage required depends on the choice of the route of administration; the nature of the formulation; the nature of the subject's illness; the subject's size, weight, surface area, age, and sex; other drugs being administered; and the judgment of the attending physician. Suitable dosages are in the range of 0.01-100.0 mg/kg. Suitable dosages are in the range of 0.01-100.0 mg/kg or more specifically 0.1-100, 0.1-75, 0.1-50, 0.1-25, 0.1-10, 0.5-100, 0.5-75, 0.5-50, 0.5-25, 0.5-10, 1-100, 1-75, 1-50, or 1-25 mg/kg. Preferable dosages include 1-10, 10-100, 10-75, 10-50, 10-25, 25-50, 50-75, 25-100, 25-50, 50-100, or 75-100 mg/kg. Most preferably, dosages can range from 1-2, 3-4, 5-6, 7-8, or 9-10 mg/kg.

Therapeutic compositions of the embodiments of the invention can be administered daily, one time, two times, or three times or more per week for between about 1 to 10 weeks, preferably between 2 to 8 weeks, more preferably between about 3 to 7 weeks, and even more preferably for about 4, 5, or 6 weeks. Variations in the needed dosage are to be expected in view of the variety of compositions available and the different efficiencies of various routes of administration. For example, oral administration would be expected to require higher dosages than administration by intravenous injection. Variations in these dosage levels can be adjusted using standard empirical routines for optimization as is well understood in the art. Encapsulation of the composition in a suitable delivery vehicle (e.g., polymeric microparticles or implantable devices) may increase the efficiency of delivery, particularly for oral delivery.

The pharmaceutically acceptable carrier includes a solvent, a dispersion medium, a coating, an antibacterial and antifungal agent, and an isotonic and absorption delaying agent. Specifically, these agents can include saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and agents for the adjustment of tonicity such as sodium chloride or dextrose. The pH of the pharmaceutical composition can be adjusted with acids or bases, such as hydrochloric acid or sodium hydroxide.

Also within the scope of the embodiments of the invention is a pharmaceutical composition that contains a pharmaceutically acceptable carrier and an effective amount of a protein complex of the embodiments of the invention. The pharmaceutical composition can be used to treat the disorders listed above. The pharmaceutically acceptable carrier includes a solvent, a dispersion medium, a coating, an antibacterial and antifungal agent, and an isotonic and absorption delaying agent. The pharmaceutical composition can be formulated into dosage forms for different administration routes utilizing conventional methods.

The efficacy of a composition of the embodiments of the invention can be evaluated both in vitro and in vivo. For in vivo studies, the composition can be injected into an animal (e.g., a mouse model) and its therapeutic effects are then accessed. Based on the results, an appropriate dosage range and administration route can be determined.

As used herein, the terms "directed against" and "specifically binds to" mean that the present fusion protein comprises an antibody domain, where the antibody or fragment of an antibody has a functional affinity of at least $10^{-6}$ M for its ligand.

In an embodiment of the invention, from N- to C-terminus, an extracellular domain of TNFαRII fused to a first collagen-like domain having the sequence of $(GPP)_{10}$ (SEQ ID NO: 21), which is in turn fused to the hinge region of IgG1 which is in turn fused to the Fc region of human IgG1.

Collagen-like domains or the present fusion proteins may include marker proteins and can be used in diagnostic and molecular imaging. In embodiments of the invention, collagen-like domain or the present fusion proteins that include marker proteins or radioactive ions, or other fusion moieties, can be packaged in a kit including the scaffold domain fusion protein and other reagents necessary for imaging of specific molecules. These reagents can include, but are not limited to, reagents for the preparation of biological samples and reagents for the visualization of the marker protein.

The embodiments of invention encompasses a method for detecting a ligand comprising incubating a trimeric soluble fusion protein comprising three polypeptides with the ligand and detecting the binding of the trimeric soluble fusion protein to the ligand. In a preferred embodiment, each polypeptide comprises a collagen-like domain comprising at least 10 G-P-X1 repeats; wherein G is glycine, P is proline, and X1 is any amino acid, wherein at least 10 of the G-P-X1 repeats are G-P-P or G-P-O, wherein at least 5, at least 6, at least 7, at least 8, at least 9, or at least 10 of the G-P-X1 repeats are G-P-O, and wherein P is proline and O is hydroxyproline; and an extracellular domain from TNFαRII; wherein the hydroxyprolinated collagen-like domains of three polypeptides interact with each other to form a trimeric soluble antibody that binds to a ligand with a functional affinity of at least $10^{-7}$ M.

In one embodiment, the soluble fusion protein has a functional affinity for its ligand of greater than $10^{-7}$ M. In one embodiment, the soluble fusion protein has a functional affinity for its ligand of greater than $10^{-8}$ M. In one embodiment, the soluble fusion protein has a functional affinity for its ligand of greater than $10^{-9}$ M.

In certain embodiments, the trimeric or hexameric soluble fusion protein comprises a luciferase polypeptide.

Embodiments of the invention include a recombinant protein complex comprising a first fusion polypeptide chain containing a first collagen-like domain and a first heterologous domain fused to one end of the first collagen-like domain; a second fusion polypeptide chain containing a second collagen-like domain; and a third fusion polypeptide chain containing a third collagen-like domain; wherein the first, second, and third collagen-like domains are aligned to form a triple helix coil.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example 1

Construction of EnbCSFc, EnbhFcCS6, EnbCS4hFc, EnbCS5hFc, EnbCS6hFc, EnbCS6hFcM, and bGalCS6hFc Listed below are the polypeptide sequence of EnbCSFc (SEQ ID NO: 1) and the cDNA sequence encoding it (SEQ ID NO: 2). The coding region of EnbCSFc, from N- to C-terminus, included a signal peptide (underline), an extracellular domain of TNFαRII, a hinge region (double-underline), a (G-P-P)$_{10}$ (SEQ ID NO: 21) collagen-like domain (boldface), a disulfide knot (GICDPSLC) (SEQ ID NO: 26) of type XXI collagen and the CH2 and CH3 domains of human IgG$_1$ (italics). This synthetic sequence (SEQ ID NO: 2) was prepared by overlapping PCR and the PCR product flanking with NheI and BamHI sites was cloned into the expression vector pSecTag2/Hygro (Invitrogen) at the same sites.

SEQ ID NO: 1

<u>MetGluThrAspThrLeuLeuLeuTrpValLeuLeuLeuTrpValProGlySerThrGlyAspAlaAlaGlnProAla</u>

ArgArgAlaLeuProAlaGlnValAlaPheThrProTyrAlaProGluProGlySerThrCysArgLeuArgGluTyr

TyrAspGlnThrAlaGlnMetCysCysSerLysCysSerProGlyGlnHisAlaLysValPheCysThrLysThrSer

AspThrValCysAspSerCysGluAspSerThrTyrThrGlnLeuTrpAsnTrpValProGluCysLeuSerCysGly

SerArgCysSerSerAspGlnValGluThrGlnAlaCysThrArgGluGlnAsnArgIleCysThrCysArgProGly

TrpTyrCysAlaLeuSerLysGlnGluGlyCysArgLeuCysAlaProLeuArgLysCysArgProGlyPheGlyVal

AlaArgProGlyThrGluThrSerAspValValCysLysProCysAlaProGlyThrPheSerAsnThrThrSerSer

ThrAspIleCysArgProHisGlnIleCysAsnValValAlaIleProGlyAsnAlaSerMetAspAlaValCysThr

SerThrSerProThrArgSerMetAlaProGlyAlaValHisLeuProGlnProValSerThrArgSerGlnHisThr

GlnProThrProGluProSerThrAlaProSerThrSerPheLeuLeuProMetGlyProSerProProAlaGluGly

SerThrGlyAspAlaAlaAla<u>GluProLysSerGlyAspLysThrHisThrCysProProCysPro</u>ArgSerIlePro

GlyProProGlyProProGlyProProGlyProProGlyProProGlyProProGlyProProGlyProProGlyPro

ProGlyProProGlyIleCysAspProSerLeuCysThrGly*ProSerValPheLeuPheProProLysProLysAsp*

*ThrLeuMetIleSerArgThrProGluValThrCysValValValAspValSerHisGluAspProGluValLysPhe*

*AsnTrpTyrValAspGlyValGluValHisAsnAlaLysThrLysProArgGluGluGlnTyrAsnSerThrTyrArg*

*ValValSerValLeuThrValLeuHisGlnAspTrpLeuAsnGlyLysGluTyrLysCysLysValSerAsnLysAla*

*LeuProAlaProIleGluLysThrIleSerLysAlaLysGlyGlnProArgGluProGlnValTyrThrLeuProPro*

*SerArgAspGluLeuThrLysAsnGlnValSerLeuThrCysLeuValLysGlyPheTyrProSerAspIleAlaVal*

*GluTrpGluSerAsnGlyGlnProGluAsnAsnTyrLysThrThrProProValLeuAspSerAspGlySerPhePhe*

*LeuTyrSerLysLeuThrValAspLysSerArgTrpGlnGlnGlyAsnValPheSerCysSerValMetHisGluAla*

*LeuHisAsnHisTyrThrGlnLysSerLeuSerLeuSerProGlyLys*

ATGGAGACAGACACACTCCTGCTATGGGTACTGCTGCTCTGGGTTCCAGGTTCCACTGGTGACGCGGCCCAGCCGGCC

AGGCGCGCCTTGCCCGCCCAGGTGGCATTTACACCCTACGCCCCGGAGCCCGGGAGCACATGCCGGCTCAGAGAATAC

TATGACCAGACAGCTCAGATGTGCTGCAGCAAATGCTCGCCGGGCCAACATGCAAAAGTCTTCTGTACCAAGACCTCG

GACACCGTGTGTGACTCCTGTGAGGACAGCACATACACCCAGCTCTGGAACTGGGTTCCCGAGTGCTTGAGCTGTGGC

TCCCGCTGTAGCTCTGACCAGGTGGAAACTCAAGCCTGCACTCGGGAACAGAACCGCATCTGCACCTGCAGGCCCGGC

TGGTACTGCGCGCTGAGCAAGCAGGAGGGGTGCCGGCTGTGCGCGCCGCTGCGCAAGTGCCGCCCGGGCTTCGGCGTG

GCCAGACCAGGAACTGAAACATCAGACGTGGTGTGCAAGCCCTGTGCCCCGGGGACGTTCTCCAACACGACTTCATCC

ACGGATATTTGCAGGCCCCACCAGATCTGTAACGTGGTGGCCATCCCTGGGAATGCAAGCATGGATGCAGTCTGCACG

-continued

```
TCCACGTCCCCCACCCGGAGTATGGCCCCAGGGGCAGTACACTTACCCCAGCCAGTGTCCACACGATCCCAACACACG

CAGCCAACTCCAGAACCCAGCACTGCTCCAAGCACCTCCTTCCTGCTCCCAATGGGCCCCAGCCCCCCAGCTGAAGGG

AGCACTGGCGACGCGGCCGCTGAGCCCAAATCTGGTGACAAAACTCACACATGCCCACCGTGCCCAAGATCTATTCCT

GGGCCACCTGGTCCCCCAGGTCCTCCAGGACCCCCAGGGCCCCCAGGCCCCCCGGGCCGCCTGGACCCCCAGGGCCA

CCAGGCCCCCCAGGCATCTGCGACCCATCACTATGTACCGGTCCGTCAGTCTTCCTCTTCCCCCCAAAACCCAAGGAC

ACCCTCATGATCTCCCGGACCCCTGAGGTCACATGCGTGGTGGTGGACGTGAGCCACGAAGACCCTGAGGTCAAGTTC

AACTGGTACGTGGACGGCGTGGAGGTGCATAATGCCAAGACAAAGCCGCGGGAGGAGCAGTACAACAGCACGTACCGT

GTGGTCAGCGTCCTCACCGTCCTGCACCAGGACTGGCTGAATGGCAAGGAGTACAAGTGCAAGGTCTCCAACAAAGCC

CTCCCAGCCCCCATCGAGAAAACCATCTCCAAAGCCAAAGGGCAGCCCCGAGAACCACAGGTGTACACCCTGCCCCCA

TCCCGGGATGAGCTGACCAAGAACCAGGTCAGCCTGACCTGCCTGGTCAAGGCTTCTATCCCAGCGACATCGCCGTGG

AGTGGGAGAGCAATGGGCAGCCGGAGAACAACTACAAGACCACGCCTCCCGTGCTGGACTCCGACGGCTCCTTCTTCC

TCTACAGCAAGCTCACCGTGGACAAGAGCAGGTGGCAGCAGGGGAACGTCTTCTCATGCTCCGTGATGCATGAGGCTC

TGCACAACCACTACACGCAGAAGAGCCTCTCCCTGTCTCCGGGTAAATGA
```

Listed below are the polypeptide sequence of EnbhFcCS6 (SEQ ID NO: 3) and the cDNA sequence encoding it (SEQ ID NO: 4). The coding region of EnbhFcCS6, from N- to C-terminus, included a signal peptide (underline), an extracellular domain of TNFαRII, a hinge region (double-underline), the CH2 and CH3 domains of human IgG$_1$ (italics), a linker (lowercase), and a collagen-like domain coding for a peptide sequence of (GPP)$_6$-GEKGEKGDPGPKGDP-(GPP)$_6$ (SEQ ID NO: 22) (boldface). This synthetic sequence (SEQ ID NO: 4) was prepared by overlapping PCR and the PCR product flanking with NheI and BamHI sites was cloned into the expression vector pSecTag2/Hygro (Invitrogen) at the same sites.

SEQ ID NO: 3

<u>MetGluThrAspThrLeuLeuLeuTrpValLeuLeuLeuTrpValProGlySerThrGlyAspAlaAlaGlnProAla</u>
ArgArgAlaLeuProAlaGlnValAlaPheThrProTyrAlaProGluProGlySerThrCysArgLeuArgGluTyr
TyrAspGlnThrAlaGlnMetCysCysSerLysCysSerProGlyGlnHisAlaLysValPheCysThrLysThrSer
AspThrValCysAspSerCysGluAspSerThrTyrThrGlnLeuTrpAsnTrpValProGluCysLeuSerCysGly
SerArgCysSerSerAspGlnValGluThrGlnAlaCysThrArgGluGlnAsnArgIleCysThrCysArgProGly
TrpTyrCysAlaLeuSerLysGlnGluGlyCysArgLeuCysAlaProLeuArgLysCysArgProGlyPheGlyVal
AlaArgProGlyThrGluThrSerAspValValCysLysProCysAlaProGlyThrPheSerAsnThrThrSerSer
ThrAspIleCysArgProHisGlnIleCysAsnValValAlaIleProGlyAsnAlaSerMetAspAlaValCysThr
SerThrSerProThrArgSerMetAlaProGlyAlaValHisLeuProGlnProValSerThrArgSerGlnHisThr
GlnProThrProGluProSerThrAlaProSerThrSerPheLeuLeuProMetGlyProSerProProAlaGluGly
SerThrGlyAspAlaAlaAla<u><u>GluProLysSerCysAspLysThrHisThrCysProProCysPro</u></u>*AlaProGluLeu
LeuGlyGlyProSerValPheLeuPheProProLysProLysAspThrLeuMetIleSerArgThrProGluValThr
CysValValValAspValSerHisGluAspProGluValLysPheAsnTrpTyrValAspGlyValGluValHisAsn
AlaLysThrLysProArgGluGluGlnTyrAsnSerThrTyrArgValValSerValLeuThrValLeuHisGlnAsp
TrpLeuAsnGlyLysGluTyrLysCysLysValSerAsnLysAlaLeuProAlaProIleGluLysThrIleSerLys
AlaLysGlyGlnProArgGluProGlnValTyrThrLeuProProSerArgAspGluLeuThrLysAsnGlnValSer
LeuThrCysLeuValLysGlyPheTyrProSerAspIleAlaValGluTrpGluSerAsnGlyGlnProGluAsnAsn
TyrLysThrThrProProValLeuAspSerAspGlySerPhePheLeuTyrSerLysLeuThrValAspLysSerArg
TrpGlnGlnGlyAsnValPheSerCysSerValMetHisGluAlaLeuHisAsnHisTyrThrGlnLysSerLeuSer
LeuSerProGlyLys*glyglyglyglyser**GlyProProGlyProProGlyProProGlyProProGlyProProGly
ProProGlyGluLysGlyGluLysGlyAspProGlyProLysGlyAspProGlyProProGlyProProGlyProPro
GlyProProGlyProProGlyProPro**GlyGlyThrGly

SEQ ID NO: 4

```
ATGGAGACAGACACACTCCTGCTATGGGTACTGCTGCTCTGGGTTCCAGGTTCCACTGGTGACGCGGCCCAGCCGGCC
AGGCGCGCCTTGCCCGCCCAGGTGGCATTTACACCCTACGCCCCGGAGCCCGGGAGCACATGCCGGCTCAGAGAATAC
TATGACCAGACAGCTCAGATGTGCTGCAGCAAATGTTCTCCGGGCCAACATGCAAAAGTCTTCTGTACCAAGACCTCG
GACACCGTGTGTGACTCCTGTGAGGACAGCACATACACCCAGCTCTGGAACTGGGTTCCCGAGTGCTTGAGCTGTGGC
TCCCGCTGTAGCTCTGACCAGGTGGAAACTCAAGCCTGCACTCGGGAACAGAACCGCATCTGCACCTGCAGGCCCGGC
TGGTACTGCGCGCTGAGCAAGCAGGAGGGGTGCCGGCTGTGCGCGCCGCTGCGCAAGTGCCGCCCGGGCTTCGGCGTG
GCCAGACCAGGAACTGAAACATGCAGACGTGGTGTGCAAGCCCTGTGCCCCGGGGACGTTCTCCAACACGACTTCATCC
ACGGATATTTGCAGGCCCCACCCAGATCTGTAACGTGGTGGCCATCCCTGGGAATGCAAGCATGGATGCAGTCTGCACG
TCCACGTCCCCCACCCGGAGTATGGCCCCAGGGGCAGTACACTTACCCCAGCCAGTGTCCACACGATCCCAACACACG
CAGCCAACTCCAGAACCCAGCACTGCTCCAAGCACCTCCTTCCTGCTCCCAATGGGCCCCAGCCCCCAGCTGAAGGG
AGCACTGGCGACGCGGCCGCTGAGCCCAAATCTTGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGATGAGCTGACCAAGAACCAGGTCAGC
CTGACCTGCCTGGTCAAAGGCTTCTATCCCAGCGACATCGCCGTGGAGTGGGAGAGCAATGGGCAGCCGGAGAACAAC
```

```
TACAAGACCACGCCTCCCGTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTACACGCAGAAGAGCCTCTCC
CTGTCTCCGGGTAAAGGTGGAGGCGGTTCAGGGCCACCTGGTCCCCCAGGTCCTCCAGGACCCCCAGGGCCCCCTGGA
CCTCCAGGTGAGAAGGGTGAGAAAGGAGATCCAGGTCCTAAGGGAGACCCTGGTCCACCAGGACCTCCTGGCCCTCCC
GGGCCGCCTGGACCCCCGGCCCTCCTGGTGGAACCGGTTGA
```

Listed below are the polypeptide sequence of EnbCS4hFc (SEQ ID NO: 5) and the cDNA sequence encoding it (SEQ ID NO: 6). The coding region of EnbCS4hFc, from N- to C-terminus, included a signal peptide (underline), an extracellular domain of TNFαRII, a hinge region (double-underline), a collagen-like domain coding for a peptide sequence of (GPP)₄-GEKGEKGDPGPKGDI-(GPP)₄ (SEQ ID NO: 23) (boldface), and the CH2 and CH3 domains of human IgG₁ (italics), and. This synthetic sequence (SEQ ID NO: 6) was prepared by overlapping PCR and the PCR product flanking with NheI and BamHI sites was cloned into the expression vector pSecTag2/Hygro (Invitrogen) at the same sites.

Listed below are the polypeptide sequence of EnbCS5hFc (SEQ ID NO: 7) and the cDNA sequence encoding it (SEQ ID NO: 8). The coding region of EnbCS5hFc, from N- to C-terminus, included a signal peptide (underline), an extracellular domain of TNFαRII, a hinge region (double-underline), a collagen-like domain coding for a peptide sequence of (GPP)₅-GEKGEKGDPGPKGDI-(GPP)₄ (SEQ ID NO: 24) (boldface), and the CH2 and CH3 domains of human IgG₁ (italics), and. This synthetic sequence (SEQ ID NO: 8) was prepared by overlapping PCR and the PCR product flanking with NheI and BamHI sites was cloned into the expression vector pSecTag2/Hygro (Invitrogen) at the same sites.

SEQ ID NO: 5

<u>MetGluThrAspThrLeuLeuLeuTrpValLeuLeuLeuTrpValProGlySerThrGlyAspAlaAlaGlnProAla</u>
ArgArgAlaLeuProAlaGlnValAlaPheThrProTyrAlaProGluProGlySerThrCysArgLeuArgGluTyr
TyrAspGlnThrAlaGlnMetCysCysSerLysCysSerProGlyGlnHisAlaLysValPheCysThrLysThrSer
AspThrValCysAspSerCysGluAspSerThrTyrThrGlnLeuTrpAsnTrpValProGluCysLeuSerCysGly
SerArgCysSerSerAspGlnValGluThrGlnAlaCysThrArgGluGlnAsnArgIleCysThrCysArgProGly
TrpTyrCysAlaLeuSerLysGlnGluGlyCysArgLeuCysAlaProLeuArgLysCysArgProGlyPheGlyVal
AlaArgProGlyThrGluThrSerAspValValCysLysProCysAlaProGlyThrPheSerAsnThrThrSerSer
ThrAspIleCysArgProHisGlnIleCysAsnValValAlaIleProGlyAsnAlaSerMetAspAlaValCysThr
SerThrSerProThrArgSerMetAlaProGlyAlaValHisLeuProGlnProValSerThrArgSerGlnHisThr
GlnProThrProGluProSerThrAlaProSerThrSerPheLeuLeuProMetGlyProSerProProAlaGluGly
SerThrGlyAspAlaAlaAla<u>GluProLysSerGlyAspLysThrHisThrCysProProCysPro</u>AlaProGluLeu
Leu**GlyGlyProProGlyProProGlyProProGlyProProGlyGluLysGlyGluLysGlyAspProGlyProLys
GlyAspIleGlyProProGlyProProGlyProProGlyProPro**GlyGlyThrGlyProSerValPheLeuPhePro
ProLysProLysAspThrLeuMetIleSerArgThrProGluValThrCysValValValAspValSerHisGluAsp
ProGluValLysPheAsnTrpTyrValAspGlyValGluValHisAsnAlaLysThrLysProArgGluGluGlnTyr
AsnSerThrTyrArgValValSerValLeuThrValLeuHisGlnAspTrpLeuAsnGlyLysGluTyrLysCysLys
ValSerAsnLysAlaLeuProAlaProIleGluLysThrIleSerLysAlaLysGlyGlnProArgGluProGlnVal
TyrThrLeuProProSerArgAspGluLeuThrLysAsnGlnValSerLeuThrCysLeuValLysGlyPheTyrPro
SerAspIleAlaValGluTrpGluSerAsnGlyGlnProGluAsnAsnTyrLysThrThrProProValLeuAspSer
AspGlySerPhePheLeuTyrSerLysLeuThrValAspLysSerArgTrpGlnGlnGlyAsnValPheSerCysSer
ValMetHisGluAlaLeuHisAsnHisTyrThrGlnLysSerLeuSerLeuSerProGlyLys

SEQ ID NO: 6

```
ATGGAGACAGACACACTCCTGCTATGGGTACTGCTGCTCTGGGTTCCAGGTTCCACTGGTGACGCGGCCCAGCCGGCC
AGGCGCGCCTTGCCCGCCCAGGTGGCATTTACACCCTACGCCCCGGAGCCCGGGAGCACATGCCGGCTCAGAGAATAC
TATGACCAGACAGCTCAGATGTGCTGCAGCAAATGCTCGCCGGGCCAACATGCAAAAGTCTTCTGTACCAAGACCTCG
GACACCGTGTGTGACTCCTGTGAGGACAGCACATACACCCAGCTCTGGAACTGGGTTCCCGAGTGCTTGAGCTGTGGC
TCCCGCTGTAGCTCTGACCAGGTGGAAACTCAAGCCTGCACTCGGGAACAGAACCGCATCTGCACCTGCAGGCCCGGC
TGGTACTGCGCGCTGAGCAAGCAGGAGGGGTGCCGGCTGTGCGCGCCGCTGCGCAAGTGCCGCCCGGGCTTCGGCGTG
GCCAGACCAGGAACTGAAACATCAGACGTGGTGTGCAAGCCCTGTGCCCCGGGGACGTTCTCCAACACGACTTCATCC
ACGGATATTTGCAGGCCCCACCAGATCTGTAACGTGGTGGCCATCCCTGGGAATGCAAGCATGGATGCAGTCTGCACG
TCCACGTCCCCCACCCGGAGTATGGCCCCAGGGGCAGTACACTTACCCCAGCCAGTGTCCAACACGATCCCAACACACG
CAGCCAACTCCAGAACCCAGCACTGCTCCAAGCACCTCCTTCCTGCTCCCAATGGGCCCAGCCCCCCAGCTGAAGGG
AGCACTGGCGACGCGGCCGCTGAGCCCAAATCTGGTGACAAAACTCACACATGCCCACCGTGCCCAGCACCTGAACTC
CTGGGAGGTCCTCCAGGACCCCCAGGGCCCCTGGGCCCCCTGGTGAGAAGGGTGAGAAAGGAGATCCAGGTCCTAAG
GGAGACATCGGCCCTCCCGGGCCGCCTGGACCCCCAGGCCCTCCTGGTGGAACCGGTCCGTCAGTCTTCCTCTTCCCC
CCAAAACCCAAGGACACCCTCATGATCTCCCGGACCCCTGAGGTCACATGCGTGGTGGTGGACGTGAGCCACGAAGAC
CCTGAGGTCAAGTTCAACTGGTACGTGGACGGCGTGGAGGTGCATAATGCCAAGACAAAGCCGCGGGAGGAGCAGTAC
AACAGCACGTACCGTGTGGTCAGCGTCCTCACCGTCCTGCACCAGGACTGGCTGAATGGCAAGGAGTACAAGTGCAAG
GTCTCCAACAAAGCCCTCCCAGCCCCCATCGAGAAAACCATCTCCAAAGCCAAAGGGCAGCCCCGAGAACCACAGGTG
TACACCCTGCCCCCATCCCGGGATGAGCTGACCAAGAACCAGGTCAGCCTGACCTGCCTGGTCAAAGGCTTCTATCCC
AGCGACATCGCCGTGGAGTGGGAGAGCAATGGGCAGCCGGAGAACAACTACAAGACCACGCCTCCCGTGCTGGACTCC
GACGGCTCCTTCTTCCTCTACAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCTCCGGGTAAATGA
```

SEQ ID NO: 7

MetGluThrAspThrLeuLeuLeuTrpValLeuLeuLeuTrpValProGlySerThrGlyAspAlaAlaGlnProAla
ArgArgAlaLeuProAlaGlnValAlaPheThrProTyrAlaProGluProGlySerThrCysArgLeuArgGluTyr
TyrAspGlnThrAlaGlnMetCysCysSerLysCysSerProGlyGlnHisAlaLysValPheCysThrLysThrSer
AspThrValCysAspSerCysGluAspSerThrTyrThrGlnLeuTrpAsnTrpValProGluCysLeuSerCysGly
SerArgCysSerSerAspGlnValGluThrGlnAlaCysThrArgGluGlnAsnArgIleCysThrCysArgProGly
TrpTyrCysAlaLeuSerLysGlnGluGlyCysArgLeuCysAlaProLeuArgLysCysArgProGlyPheGlyVal
AlaArgProGlyThrGluThrSerAspValValCysLysProCysAlaProGlyThrPheSerAsnThrThrSerSer
ThrAspIleCysArgProHisGlnIleCysAsnValValAlaIleProGlyAsnAlaSerMetAspAlaValCysThr
SerThrSerProThrArgSerMetAlaProGlyAlaValHisLeuProGlnProValSerThrArgSerGlnHisThr
GlnProThrProGluProSerThrAlaProSerThrSerPheLeuLeuProMetGlyProSerProProAlaGluGly
SerThrGlyAspAlaAlaAlaGluProLysSerGlyAspLysThrHisTluCysProProCysProAlaProGluLeu
Leu**GlyGlyProGlyProProGlyProProGlyProProGlyProProGlyProProGlyGluLysGlyGluLysGlyAspPro
GlyProLysGlyAspIleGlyProProGlyProProGlyProProGlyProPro**GlyGlyThrGly*ProSerValPhe
LeuPheProProLysProLysAspThrLeuMetIleSerArgThrProGluValThrCysValValValAspValSer
HisGluAspProGluValLysPheAsnTrpTyrValAspGlyValGluValHisAsnAlaLysThrLysProArgGlu
GluGlnTyrAsnSerThrTyrArgValValSerValLeuThrValLeuHisGlnAspTrpLeuAsnGlyLysGluTyr
LysCysLysValSerAsnLysAlaLeuProAlaProIleGluLysThrIleSerLysAlaLysGlyGlnProArgGlu
ProGlnValTyrThrLeuProProSerArgAspGluLeuThrLysAsnGlnValSerLeuThrCysLeuValLysGly
PheTyrProSerAspIleAlaValGluTrpGluSerAsnGlyGlnProGluAsnAsnTyrLysThrThrProProVal
LeuAspSerAspGlySerPhePheLeuTyrSerLysLeuThrValAspLysSerArgTrpGlnGlnGlyAsnValPhe
SerCysSerValMetHisGluAlaLeuHisAsnHisTyrThrGlnLysSerLeuSerLeuSerProGlyLys*

SEQ ID NO: 8

```
ATGGAGACAGACACACTCCTGCTATGGGTACTGCTGCTCTGGGTTCCAGGTTCCACTGGTGACGCGGCCCAGCCGGCC
AGGCGCGCCTTGCCCGCCAGGTGGCATTTACACCCTACGCCCCGGAGCCCGGGAGCACATGCCGGCTCAGAGAATAC
TATGACCAGACAGCTCAGATGTGCTGCAGCAAATGCTCGCCGGGCCAACATGCAAAAGTCTTCTGTACCAAGACCTCG
GACACCGTGTGTGACTCCTGTGAGGACAGCACATACACCCAGCTCTGGAACTGGGTTCCCGAGTGCTTGAGCTGTGGC
TCCCGCTGTAGCTCTGACCAGGTGGAAACTCAAGCCTGCACTCGGGAACAGAACCGCATCTGCACCTGCAGGCCCGGC
TGGTACTGCGCGCTGAGCAAGCAGGAGGGGTGCCGGCTGTGCGCGCCGCTGCCAAGTGCCGCCCGGGCTTCGGCGTG
GCCAGACCAGGAACTGAAACATCAGACGTGGTGTGCAAGCCCTGTGCCCCGGGACGTTCTCCAACACGACTTCATCC
ACGGATATTTGCAGGCCCCACCAGATCTGTAACGTGGTGGCCATCCCTGGGAATGCAAGCATGGATGCAGTCTGCACG
TCCACGTCCCCCACCCGGAGTATGGCCCCAGGGGCAGTACACTTACCCCAGCCAGTGTCCACACGATCCCAACACACG
CAGCCAACTCCAGAACCCAGCACTGCTCCAAGCACCTCCTTCCTGCTCCCAATGCCCACCGTGCCCAGCACCTGAACTC
AGCACTGGCGACGCGGCCGCTGAGCCCAAATCTGGTGACAAAACTCACACATGCCCACCGTGCCCAGCACCTGAACTC
CTGGGAGGTCCTCCAGGACCCCCAGGGCCCCCTGGGCCCCCTGGTGAAGGGTGAGAAAGGAGATCCA
GGTCCTAAGGGAGACATCGGCCCTCCCGGGCCGCCTGGACCCCCAGGCCCTCCTGGTGGAACCGGTCCGTCAGTCTTC
CTCTTCCCCCCAAAACCCAAGGACACCCTCATGATCTCCCGGACCCCTGAGGTCACATGCGTGGTGGTGGACGTGAGC
CACGAAGACCCTGAGGTCAAGTTCAACTGGTACGTGGACGGCGTGGAGGTGCATAATGCCAAGACAAAGCCGCGGGAG
GAGCAGTACAACAGCACGTACCGTGTGGTCAGCGTCCTCACCGTCCTGCACCAGGACTGGCTGAATGGCAAGGAGTAC
AAGTGCAAGGTCTCCAACAAAGCCCTCCCAGCCCCCATCGAGAAAACCATCTCCAAAGCCAAAGGGCAGCCCCGAGAA
CCACAGGTGTACACCCTGCCCCCATCCCGGGATGAGCTGACCAAGAACCAGGTCAGCCTGACCTGCCTGGTCAAAGGC
TTCTATCCCAGCGACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGACAAGAGCAGGTGGCAGCAGGGGAACGTCTTC
TCATGCTCCGTGATGCATGAGGCTCTGCACAACCACTACACGCAGAAGAGCCTCTCCCTGTCTCCGGGTAAATGA
```

Listed below are the polypeptide sequence of EnbCS6hFc (SEQ ID NO: 9) and the cDNA sequence encoding it (SEQ ID NO: 10). The coding region of EnbCS6hFc, from N- to C-terminus, included a signal peptide (underline), an extracellular domain of TNFαRII, a hinge region (double-underline), a collagen-like domain coding for a peptide sequence of (GPP)$_6$-GEKGEKGDPGPKGDI-(GPP)$_6$ (SEQ ID NO: 35) (boldface), and the CH2 and CH3 domains of human IgG$_1$ (italics). This synthetic sequence (SEQ ID NO: 10) was prepared by overlapping PCR and the PCR product flanking with NheI and BamHI sites was cloned into the expression vector pSecTag2/Hygro (Invitrogen) at the same sites.

SEQ ID NO: 9

MetGluThrAspThrLeuLeuLeuTrpValLeuLeuLeuTrpValProGlySerThrGlyAspAlaAlaGlnProAla
ArgArgAlaLeuProAlaGlnValAlaPheThrProTyrAlaProGluProGlySerThrCysArgLeuArgGluTyr
TyrAspGlnThrAlaGlnMetCysCysSerLysCysSerProGlyGlnHisAlaLysValPheCysThrLysThrSer
AspThrValCysAspSerCysGluAspSerThrTyrThrGlnLeuTrpAsnTrpValProGluCysLeuSerCysGly
SerArgCysSerSerAspGlnValGluThrGlnAlaCysThrArgGluGlnAsnArgIleCysThrCysArgProGly
TrpTyrCysAlaLeuSerLysGlnGluGlyCysArgLeuCysAlaProLeuArgLysCysArgProGlyPheGlyVal
AlaArgProGlyThrGluThrSerAspValValCysLysProCysAlaProGlyThrPheSerAsnThrThrSerSer
ThrAspIleCysArgProHisGlnIleCysAsnValValAlaIleProGlyAsnAlaSerMetAspAlaValCysThr
SerThrSerProThrArgSerMetAlaProGlyAlaValHisLeuProGlnProValSerThrArgSerGlnHisThr
GlnProThrProGluProSerThrAlaProSerThrSerPheLeuLeuProMetGlyProSerProProAlaGluGly
SerThrGlyAspAlaAlaAlaGluProLysSerGlyAspLysThrHisThrCysProProCysProAlaProGluLeu
Leu**GlyProGlyProProGlyProProGlyProProGlyProProGlyProProGlyProProGlyGluLysGlyGluLys
GlyAspProGlyProLysGlyAspProGlyProProGlyProProGlyProProGlyProProGlyProProGlyProPro
Pro**GlyGlyThrGly*ProSerValPheLeuPheProProLysProLysAspThrLeuMetIleSerArgThrProGlu
ValThrCysValValValAspValSerHisGluAspProGluValLysPheAsnTrpTyrValAspGlyValGluVal
HisAsnAlaLysThrLysProArgGluGluGlnTyrAsnSerThrTyrArgValValSerValLeuThrValLeuHis
GlnAspTrpLeuAsnGlyLysGluTyrLysCysLysValSerAsnLysAlaLeuProAlaProIleGluLysThrIle
SerLysAlaLysGlyGlnProArgGluProGlnValTyrThrLeuProProSerArgAspGluLeuThrLysAsnGln
ValSerLeuThrCysLeuValLysGlyPheTyrProSerAspIleAlaValGluTrpGluSerAsnGlyGlnProGlu
AsnAsnTyrLysThrThrProProValLeuAspSerAspGlySerPhePheLeuTyrSerLysLeuThrValAspLys
SerArgTrpGlnGlnGlyAsnValPheSerCysSerValMetHisGluAlaLeuHisAsnHisTyrThrGlnLysSer
LeuSerLeuSerProGlyLys*

SEQ ID NO: 10

```
ATGGAGACAGACACACTCCTGCTATGGGTACTGCTGCTCTGGGTTCCAGGTTCCACTGGTGACGCGGCCCAGCCGGCC
AGGCGCGCCTTGCCCGCCCAGGTGGCATTTACACCCTACGCCCCGGAGCCCGGGAGCACATGCCGGCTCAGAGAATAC
TATGACCAGACAGCTCAGATGTGCTGCAGCAAATGCTCGCCGGGCCAACATGCAAAAGTCTTCTGTACCAAGACCTCG
GACACCGTGTGTGACTCCTGTGAGGACAGCACATACACCCAGCTCTGGAACTGGGTTCCCGAGTGCTTGAGCTGTGGC
TCCCGCTGTAGCTCTGACCAGGTGGAAACTCAAGCCTGCACTCGGGAACAGAACCGCATCTGCACCTGCAGGCCCGGC
TGGTACTGCGCGCTGAGCAAGCAGGAGGGGTGCCGGCTGTGCGCGCCGCTGCGCAAGTGCCGCCCGGGCTTCGGCGTG
GCCAGACCAGGAACTGAAACATCAGACGTGGTGTGCAAGCCCTGTGCCCCGGGGACGTTCTCCAACACGACTTGTGGC
CATCCACGGATATTTGCAGGCCCCACCAGATCTGTAACGTGGTGGCCATCCCTGGGAATGCAAGCATGGATGCAGTCTGCACG
TCCACGTCCCCCACCCGGAGTATGGCCCCAGGGGCAGTACACTTACCCCAGCCAGTGTCCACACGATCCCAACACACG
CAGCCAACTCCAGAACCCAGCACTGCTCCAAGCACCTCCTTCCTGCTCCCAATGGGCCCCAGCCCCCCAGCTGAAGGG
AGCACTGGCGACGCGGCCGCTGAGCCCAAATCTGGTGACAAAACTCACACATGCCCACCGTGCCCAGCACCTGAACTC
CTGGGAGGGCCACCTGGTCCCCCAGGTCCTCCAGGACCCCCAGGGCCCCCTGGACCTCCAGGTGAGAAGGGTGAGAAA
GGAGATCCAGGTCCTAAGGGAGACCCTGGTCCACCAGGACCTCCTGGCCCTCCCGGGCCGCCTGGACCCCCAGGCCCT
CCTGGTGGAACCGGTCCGTCAGTCTTCCTCTTCCCCCCAAAACCCAAGGACACCCTCATGATCTCCCGGACCCCTGAG
GTCACATGCGTGGTGGTGGACGTGAGCCACGAAGACCCTGAGGTCAAGTTCAACTGGTACGTGGACGGCGTGGAGGTG
CATAATGCCAAGACAAAGCCGCGGGAGGAGCAGTACAACAGCACGTACCGTGTGGTCAGCGTCCTCACCGTCCTGCAC
CAGGACTGGCTGAATGGCAAGGAGTACAAGTGCAAGGTCTCCAACAAAGCCCTCCCAGCCCCCATCGAGAAAACCATC
TCCAAAGCCAAAGGGCAGCCCCGAGAACCACAGGTGTACACCCTGCCCCCATCCCGGGATGAGCTGACCAAGAACCAG
GTCAGCCTGACCTGCCTGGTCAAAGGCTTCTATCCCAGCGACATCGCCGTGGAGTGGGAGAGCAATGGGCAGCCGGAG
AACAACTACAAGACCACGCCTCCCGTGCTGGACTCCGACGGCTCCTTCTTCCTCTACAGCAAGCTCACCGTGGACAAG
AGCAGGTGGCAGCAGGGAACGTCTTCTCATGCTCCGTGATGCATGAGGCTCTGCACAACCACTACACGCAGAAGAGCC
TCTCCCTGTCTCCGGGTAATGA
```

Listed below are the polypeptide sequence of EnbCS6hFcM (SEQ ID NO: 11) and the cDNA sequence encoding it (SEQ ID NO: 12). The coding region of EnbCS6hFcM, from N- to C-terminus, included a signal peptide (underline), an extracellular domain of TNFαRII, a hinge region (double-underline), a collagen-like domain coding for a peptide sequence of (GPP)$_6$-GEKGEKGDPGPKGDI-(GPP)$_6$ (SEQ ID NO: 35) (boldface), and the mutated CH2 and CH3 domains of human IgG$_1$ (italics). This synthetic sequence (SEQ ID NO: 12) was prepared by overlapping PCR and the PCR product flanking with NheI and BamHI sites was cloned into the expression vector pSecTag2/Hygro (Invitrogen) at the same sites.

SEQ ID NO: 11

<u>MetGluThrAspThrLeuLeuLeuTrpValLeuLeuLeuTrpValProGlySerThrGlyAspAlaAlaGlnProAla</u>
ArgArgAlaLeuProAlaGlnValAlaPheThrProTyrAlaProGluProGlySerThrCysArgLeuArgGluTyr
TyrAspGlnThrAlaGlnMetCysCysSerLysCysSerProGlyGlnHisAlaLysValPheCysThrLysThrSer
AspThrValCysAspSerCysGluAspSerThrTyrThrGlnLeuTrpAsnTrpValProGluCysLeuSerCysGly
SerArgCysSerSerAspGlnValGluThrGlnAlaCysThrArgGluGlnAsnArgIleCysThrCysArgProGly
TrpTyrCysAlaLeuSerLysGlnGluGlyCysArgLeuCysAlaProLeuArgLysCysArgProGlyPheGlyVal
AlaArgProGlyThrGluThrSerAspValValCysLysProCysAlaProGlyThrPheSerAsnThrThrSerSer
ThrAspIleCysArgProHisGlnIleCysAsnValValAlaIleProGlyAsnAlaSerMetAspAlaValCysThr
SerThrSerProThrArgSerMetAlaProGlyAlaValHisLeuProGlnProValSerThrArgSerGlnHisThr
GlnProThrProGluProSerThrAlaProSerThrSerPheLeuLeuProMetGlyProSerProProAlaGluGly
SerThrGlyAspAlaAlaAla<u>GluProLysSerGlyAspLysThrHisThrCysProProCysPro</u>AlaProGluLeu
LeuGly**GlyProProGlyProProGlyProProGlyProProGlyProProGlyProProGlyGluLysGlyGluLys
GlyAspProGlyProLysGlyAspProGlyProProGlyProProGlyProProGlyProProGlyProProGlyPro
Pro**GlyGlyThrGly*ProSerValPheLeuPheProProLysProLysAspThrLeuMetIleSerArgThrProGlu
ValThrCysValValValAspValSerHisGluAspProGluValLysPheAsnTrpTyrValAspGlyValGluVal
HisAsnAlaLysThrLysProArgGluGluGlnTyrAsnSerThrTyrArgValValSerValLeuThrValLeuHis
GlnAspTrpLeuAsnGlyLysGluTyrLysCysLysValSerAsnLysAlaLeuProAlaProIleGluLysThrIle
SerLysAlaLysGlyGlnProArgGluProGlnValTyrThrLeuProProSerArgAspGluLeuThrLysAsnGln
ValSerLeuSerCysAlaValLysGlyPheTyrProSerAspIleAlaValGluTrpGluSerAsnGlyGlnProGlu
AsnAsnTyrLysThrThrProProValLeuAspSerAspGlySerPhePheLeuValSerLysLeuThrValAspLys
SerArgTrpGlnGlnGlyAsnValPheSerCysSerValMetHisGluAlaLeuHisAsnHisTyrThrGlnLysSer
LeuSerLeuSerProGlyLys*

SEQ ID NO: 12

```
ATGGAGACAGACACACTCCTGCTATGGGTACTGCTGCTCTGGGTTCCAGGTTCCACTGGTGACGCGGCCCAGCCGGCCA
GGCGCGCCTTGCCCGCCCAGGTGGCATTTACACCCTACGCCCCGGAGCCCGGGAGCACATGCCGGCTCAGAGAATACTA
TGACCAGACAGCTCAGATGTGCTGCAGCAAATGCTCGCCGGGCCAACATGCAAAAGTCTTCTGTACCAAGACCTCGGAC
ACCGTGTGTGACTCCTGTGAGGACAGCACATACACCCAGCTCTGGAACTGGGTTCCCGAGTGCTTGAGCTGTGGCTCCC
GCTGTAGCTCTGACCAGGTGGAAACTCAAGCCTGCACTCGGGAACAGAACCGCATCTGCACCTGCAGGCCCGGCTGGTA
CTGCGCGCTGAGCAAGCAGGAGGGGTGCCGGCTGTGCGCGCCGCTGCGCAAGTGCCGCCCGGGCTTCGGCGTGGCCAGA
CCAGGAACTGAAACATCAGACGTGGTGTGCAAGCCCTGTGCCCCGGGGACGTTCTCCAACACGACTTCATCCACGGATA
TTTGCAGGCCCCACCAGATCTGTAACGTGGTGGCCATCCCTGGGAATGCAAGCATGGATGCAGTCTGCACGTCCACGTC
CCCCACCCGGAGTATGGCCCCAGGGGCAGTACACTTACCCCAGCCAGTGTCCACACGATCCCAACACACGCAGCCAACT
CCAGAACCCAGCACTGCTCCAAGCACCTCCTTCCTGCTCCCAATGGGCCCCAGCCCCCAGCTGAAGGGAGCACTGGCG
ACGCGGCCGCTGAGCCCAAATCTGGTGACAAAACTCACACATGCCCACCGTGCCCAGCACCTGAACTCCTGGGAGGGCC
ACCTGGTCCCCCAGGTCCTCCAGGACCCCCAGGGCCCCCTGGACCTCCAGGTGAGAAGGGTGAGAAAGGAGATCCAGGT
CCTAAGGGAGACCCTGGTCCACCAGGACCTCCTGGCCCTCCCGGGCCGCCTGGACCCCCAGGCCCTCCTGGTGGAACCG
GTCCGTCAGTCTTCCTCTTCCCCCCAAAACCCAAGGACACCCTCATGATCTCCCGGACCCCTGAGGTCACATGCGTGGT
GGTGGACGTGAGCCACGAAGACCCTGAGGTCAAGTTCAACTGGTACGTGGACGGCGTGGAGGTGCATAATGCCAAGACA
AAGCCGCGGGAGGAGCAGTACAACAGCACGTACCGTGTGGTCAGCGTCCTCACCGTCCTGCACCAGGACTGGCTGAATG
GCAAGGAGTACAAGTGCAAGGTCTCCAACAAAGCCCTCCCAGCCCCCATCGAGAAAACCATCTCCAAAGCCAAAGGGCA
GCCCCGAGAACCACAGGTGTACACCCTGCCCCCATCCCGGGATGAGCTGACCAAGAACCAGGTCAGCCTGTCCTGCGCG
GTCAAAGGCTTCTATCCCAGCGACATCGCCGTGGAGTGGGAGAGCAATGGGCAGCCGGAGAACAACTACAAGACCACGC
```

```
CTCCCGTGCTGGACTCCGACGGCTCCTTCTTCCTCGTCAGCAAGCTCACCGTGGACAAGAGCAGGTGGCAGCAGGGGAA
CGTCTTCTCATGCTCCGTGATGCATGAGGCTCTGCACAACCACTACACGCAGAAGAGCCTCTCCCTGTCTCCGGGTAAA
TGA
```

Listed below are the polypeptide sequence of bGalCS6hFc (SEQ ID NO: 13) and the cDNA sequence encoding it (SEQ ID NO: 14). The coding region of bGalCS6hFc, from N- to C-terminus, included a signal peptide (underline), a $V_H$ domain antibody of anti-β-galactosidase (Source BioScience LifeSciences, UK), a linker (lowercase), a collagen-like domain coding for a peptide sequence of $(GPP)_6$-GEKGEKGDPGPKGDP-$(GPP)_6$ (SEQ ID NO: 22) (boldface), a hinge region (double-underline), and the CH2 and CH3 domains of human $IgG_1$ (italics). This synthetic sequence (SEQ ID NO: 14) was prepared by overlapping PCR and the PCR product flanking with NheI and BamHI sites was cloned into the expression vector pSecTag2/Hygro (Invitrogen) at the same sites.

Example 2

Expression and Purification of Fc Fusion Proteins Containing Collagen-Like Peptides The above expression constructs of EnbCSFc, EnbhFcCS6, EnbCS4hFc, EnbCS5hFc, EnbCS6hFc, EnbCS6hFcM, and bGalCS6hFc were used to transfect mouse myeloma NS0 cells (European Collection of Animal Cell Cultures, Wiltshire, UK) using Effectene (Qiagen) according to the manufacturer's instructions. After selection with Hygromycin B (400 μg/ml) for 4 weeks, stable clones were cultured in a shaker flask at an initial seeding density of $5 \times 10^5$ cells/ml in a chemically-defined medium HyQCDM4NS0 (Hyclone) containing 2% of fetal bovine serum. The culture was maintained at 130 rpm for five days at 37° C. For the purification of the above Fc-containing collagen fusion proteins, around 1 L each of the filtered culture media were applied to a HiTrap Protein A HP column (1-ml in bed volume, GE Healthcare) equilibrated with phosphate buffered saline (PBS), pH 7.4 (0.01 M phosphate buffer, 0.0027 M KCl, 0.14 M NaCl) at a flow rate of 60 ml/h. After washing with the same buffer, the recombinant antibodies were eluted with 50 mM of sodium phosphate buffer, pH 2.5.

SEQ ID NO: 13

```
MetGluThrAspThrLeuLeuLeuTrpValLeuLeuLeuTrpValProGlySerThrGlyAspAlaAlaGlnProAla
ArgArgAlaGlnValGlnLeuLeuGluSerGlyGlyGlyLeuValGlnProGlyGlySerLeuArgLeuSerCysAla
AlaSerGlyValSerIleThrAlaGluSerMetSerTrpValArgGlnAlaProGlyLysGlyLeuGluTrpValSer
ThrIleThrMetArgAspGlySerThrTyrTyrAlaAspSerValLysGlyArgPheThrIleSerArgAspAsnSer
LysAsnThrLeuTyrLeuGlnMetAsnSerLeuArgAlaGluAspThrAlaValTyrTyrCysAlaArgAlaArgAla
MetTyrProLeuArgSerSerGlnLeuGluSerTrpGlyGlnGlyThrLeuValThrValSeralaalaalagly
glyglyglyserGlyProProGlyProProGlyProProGlyProProGlyProProGlyProProGlyGluLysGly
GluLysGlyAspProGlyProLysGlyAspProGlyProProGlyProProGlyProProGlyProProGlyProPro
GlyProProGlyGlyThrGlyGluProLysSerGlyAspLysThrHisThrCysProProCysProAlaProGluLeu
LeuGlyGlyProSerValPheLeuPheProProLysProLysAspThrLeuMetIleSerArgThrProGluValThr
CysValValValAspValSerHisGluAspProGluValLysPheAsnTrpTyrValAspGlyValGluValHisAsn
AlaLysThrLysProArgGluGluGlnTyrAsnSerThrTyrArgValValSerValLeuThrValLeuHisGlnAsp
TrpLeuAsnGlyLysGluTyrLysCysLysValSerAsnLysAlaLeuProAlaProIleGluLysThrIleSerLys
AlaLysGlyGlnProArgGluProGlnValTyrThrLeuProProSerArgAspGluLeuThrLysAsnGlnValSer
LeuThrCysLeuValLysGlyPheTyrProSerAspIleAlaValGluTrpGluSerAsnGlyGlnProGluAsnAsn
TyrLysThrThrProProValLeuAspSerAspGlySerPhePheLeuTyrSerLysLeuThrValAspLysSerArg
TrpGlnGlnGlyAsnValPheSerCysSerValMetHisGluAlaLeuHisAsnHisTyrThrGlnLysSerLeuSer
LeuSerProGlyLys
```

SEQ ID NO: 14

```
ATGGAGACAGACACACTCCTGCTATGGGTACTGCTGCTCTGGGTTCCAGGTTCCACTGGTGACGCGGCCCAGCCGGCC
AGGCGCGCCCAGGTGCAGCTGTTGGAGTCTGGGGGAGGCTTGGTACAGCCTGGGGGGTCCCTGCGTCTCTCCTGTGCA
GCCTCCGGAGTTAGCATTACCGCTGAGTCTATGAGCTGGGTCCGCCAGGCTCCAGGGAAGGGTCTAGAGTGGGTATCA
ACCATTACGATGCGAGACGGTAGCACATACTACGCAGACTCCGTGAAGGGCCGGTTCACCATCTCCCGTGACAATTCC
AAGAACACGCTGTATCTGCAAATGAACAGCCTGCGTGCCGAGGACACCGCGGTATATTATTGCGCGAGAGCTAGGGCT
ATGTATCCTTTGCGTTCGTCGCAGTTGGAGTCTTGGGGTCAGGGAACCCTGGTCACCGTCTCGAGCGCGGCCGCTGGT
GGAGGCGGTTCAGGGCCACCTGGTCCCCCAGGTCCTCCAGGACCCCCAGGGCCCCCTGGACCTCCAGGTGAGAAGGGT
GAGAAAGGAGATCCAGGTCCTAAGGGAGACCCTGGTCCACCAGGACCTCCTGGACCTCCCGGGCCGCCTGGACCCCCA
GGCCCTCCTGGTGGAACCGGTGAGCCCAAATCTGGTGACAAAACTCACACATGCCCACCGTGCCCAGCACCTGAACTC
CTGGGGGGACCGTCAGTCTTCCTCTTCCCCCCAAAACCCAAGGACACCCTCATGATCTCCCGGACCCCTGAGGTCACA
TGCGTGGTGGTGGACGTGAGCCACGAAGACCCTGAGGTCAAGTTCAACTGGTACGTGGACGGCGTGGAGGTGCATAAT
GCCAAGACAAAGCCGCGGGAGGAGCAGTACAACAGCACGTACCGTGTGGTCAGCGTCCTCACCGTCCTGCACCAGGAC
TGGCTGAATGGCAAGGAGTACAAGTGCAAGGTCTCCAACAAAGCCCTCCCAGCCCCCATCGAGAAAACCATCTCCAAA
GCCAAAGGGCAGCCCCGAGAACCACAGGTGTACACCCTGCCCCCATCCCGGGATGAGCTGACCAAGAACCAGGTCAGC
CTGACCTGCCTGGTCAAAGGCTTCTATCCCAGCGACATCGCCGTGGAGTGGGAGAGCAATGGGCAGCCGGAGAACAAC
TACAAGACCACGCCTCCCGTGCTGGACTCCGACGGCTCCTTCTTCCTCTACAGCAAGCTCACCGTGGACAAGAGCAGG
TGGCAGCAGGGGAACGTCTTCTCATGCTCCGTGATGCATGAGGCTCTGCACAACCACTACACGCAGAAGAGCCTCTCC
CTGTCTCCGGGTAAATGA
```

FIG. 1 is a schematic representation of different formats of Fc fusion molecules according to the embodiments: Format A: EnbCSFc (SEQ ID NO: 37); Format B: EnbhFcCS6 (SEQ ID NOS: 38 and 34); Format C: EnbCS4hFc, EnbCS5hFc, and EnbCS6hFc (SEQ ID NOS: 39 and 34); Format D: EnbCS6hFcM (SEQ ID NOS: 39 and 34); and Format E: bGalCS6hFc (SEQ ID NOS: 38 and 34).

The UV absorbance was monitored at 280 nm and the peak fraction was collected, neutralized with 1.0 M of sodium bicarbonate to pH 7.5.

SDS-PAGE was carried out using either a 4-12% NuPAGE bis-Tris polyacrylamide gel with MES as running buffer (Invitrogen, San Diego, Calif.). Proteins were stained with InstantBlue, (Expedeon, Cambridgeshire, UK). HiMark and Bench Mark (Invitrogen, San Diego, Calif.) were used as molecular size standards.

Table 1 summarized the results of the Fc-fusion molecules used in the present invention. The structure, format A of EnbCSFc, consisting of an N-terminal extracellular domain of TNFαRII, followed by a $(GPP)_{10}$ (SEQ ID NO: 21) collagen-like peptide and an Fc fragment of human $IgG_1$, was able to be expressed as soluble secretory proteins in mouse myeloma NS0 cells. However, the major form presence in the SDS gel under non-reducing conditions is dimeric, indicating that the dimerization force of the Fc fragment dominates the trimeric assembly power of the $(GPP)_{10}$ (SEQ ID NO: 21) collagen-like peptide domain to its fusion partners. In order to obtain a predominantly trimeric Fc-containing fusion molecule, a novel trimerizing domain, comprising an extended variation of the peptide sequence of the GXKGE(D) (SEQ ID NO: 34) motif, GEKGEKGDPGPKGDP (SEQ ID NO: 59), was first employed to substitute the $(GPP)_{10}$ (SEQ ID NO: 21) collagen motif. Unfortunately, this tandem trimerizing motif, including variants on the GXKGE(D) (SEQ ID NO: 34) motif still result in a dimeric structure of the Fc-containing fusion molecules. Therefore, a composite collagen-like peptide with a sequence of $(GPP)_n$-GEKGEKGDPGPKGDP-$(GPP)_m$ where n=1-6 and m=4-10 (SEQ ID NO: 36), was designed hopefully to drive and stabilize the trimeric assembly of the fusion partners when a stable dimerizing Fc fragment is present. As shown in different structures of format C and E in Table 1, by gradually increasing the repeating numbers of the GPP triplet flanking the trimerizing motif which includes tandem GXKGE(D) motifs (SEQ ID NO: 34), stable trimeric Fc fusions unexpectedly started to be predominant over the dimeric structure. Since the Fc trimer contains an unpaired monomeric Fc fragment, a hexameric Fc fusion is formed by inter-molecular dimerization of the two trimeric fusions through their unpaired Fc fragment.

The structure features of EnbCS6hFc, EnbCS6FcM, and bGalCS6hFc were chosen for further characterization.

The constructs were electrophoresed for further structural characterization. All samples with equal amounts of protein were electrophoresed on a 4-12% SDS/Bis-Tris polyacrylamide gel with MES as a running buffer. The gels were stained with GelCode Blue Safe Protein Stain solution.

In FIG. 2A, Etanercept and EnbCS6hFc were electrophoresed under non-reducing conditions and reducing conditions, where sample was treated with 50 mM of DTT for 10 min at 75° C. Etanercept migrated as a dimer in SDS-PAGE under non-reducing conditions with an apparent molecular mass of 150 kD (lane 2), revealing a monomeric form with an apparent molecular mass of 75 kD after the interchain disulfide bonds were reduced (lane 3). A monomeric form of EnbCS6hFc with an apparent molecular mass of 85 kD was resolved when sample was treated with 50 mM of DTT for 10 min at 75° C. (lane 5). Under non-reducing conditions, one major band with an apparent molecular mass more than 500 kD was resolved (lane 4). This oligomeric structure was believed to be the hexamer form of EnbCS6hFc, where two trimers were associated by inter-molecular dimerization and cross-linking through their unpaired Fc fragment, followed by interchain disulfide bridging in the hinge region. This finding was confirmed as shown by FIG. 2B, where the sample from lane 4 (presumably) EnbCS6hFc was electrophoresed under non-reducing conditions and reducing conditions, where sample was treated with 50 mM of DTT for 10 min at ambient temperature. By incubating the sample under mild reducing conditions, 50 mM of DTT for 10 min at ambient temperature, the interchain disulfide-bonded hexamer of EnbCS6hFc was reduced and dissociated by SDS into two trimers with an apparent molecular mass of 255 kD, and notably, the most trimers were stable enough to resist dissociation by SDS (FIG. 2B, lane 3). EnbCS6hFcM was also electrophoresed under non-reducing conditions and reducing conditions, where sample was treated with 50 mM of DTT for 10 min at 75° C. In FIG. 2C, under non-reducing conditions, EnbCS6FcM exhibited as a trimeric structure (lane 2) and was mostly reduced to monomer polypeptides when the sample was treated with 50 mM of DTT for 10 min at 75° C. (lane 3). bGalCS6hFc was electrophoresed under non-reducing conditions and reducing conditions, where sample was treated with 50 mM of DTT for 10 min at 75° C. In FIG. 2D, a monomeric Run of bGalCS6hFc with an apparent molecular mass of 53 kD was resolved when sample was treated with 50 mM of DTT for 10 min at 75° C. (lane 3). Under non-reducing conditions, two major bands with apparent molecular masses of 400 kD and 200 kD, corresponding closely to the hexamer and trimer forms of bGalCS6hFc, were resolved, respectively (lane 2). It is possible that the trimer was derived from a non-interchain disulfide bonded two trimers of a hexamer, which dissociated into two trimers in SDS-PAGE under non-reducing conditions.

Finally, EnbCS6hFc expressed in NS0 cells and EnbCS6hFc expressed in CHO—S cells were electrophoresed under non-reducing conditions and reducing conditions, where samples were treated with 50 mM of DTT for 10 min at 75° C. FIG. 2E demonstrates that the present fusion proteins can be expressed from multiple cell types, including NS0 and CHO—S cells, and that trimers and hexamers are formed in either cell type. This was unexpected because when a fusion protein having a structure, from N to C terminus, of a TNF receptor domain, an Fc domain and a collagen-like domain is expressed it is not secreted. In contrast, EnbCS6hFc or EnbCS6FcM, where the domains have a structure from N to C terminus of TNF receptor domain, a collagen-like domain, and a Fc domain, it was secreted and appropriately assembled into a trimer or hexamer structure. Since the TNF receptor domain is highly glycosylated, the difference in molecular size of EnbCS6hFc expressed in NS0 and CHO—S cells could be due to the post-translational modification of the protein.

Example 3

Determination of TNFα Binding Activities by ELISA

Figure 5:
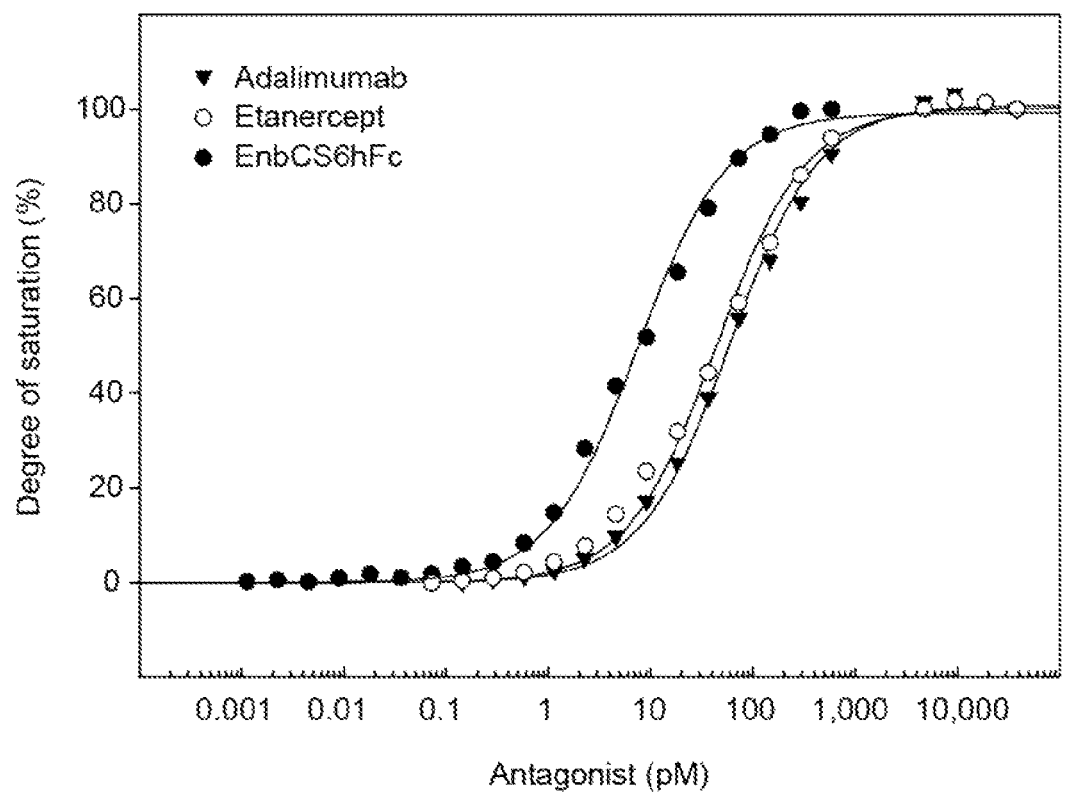
FIG. 5 depicts the binding affinities of different TNFα antagonists to TNFα according to the embodiments.

The binding activities of adalimumab (Humira, Abbott Park, Ill., USA), etanercept (Enbrel, Wyeth Taiwan Corporation), and EnbCS6hFc to soluble TNFα were determined by ELISA. The microtiter plate was coated with 2 μg/ml of TNFα in PBS overnight at 4° C. After blocking the wells with StartingBlock™ blocking buffer (Thermo Scientific), 2-fold serial dilutions of individual TNFα antagonists were added and incubated for 1 hour at 37° C. After washing, the bound TNFα antagonists were detected by incubation with horseradish peroxidase-conjugated goat anti-human IgG Fcγ fragment (Jackson ImmunoResearch Laboratories, Inc., West Grove, Pa.) for 1 hour at 37° C. and using 3,3',5,5',-tetramethylbenzidine as substrate. Absorbance was read at 450 nm on a microplate reader. The dissociation constant ($K_D$) of each antagonist was calculated as the concentration of the antagonists required to achieve half-saturation of the total bindings (maximum absorbance). In FIG. 5, the $K_D$ values of etanercept, adalimumab and EnbCS6hFc were calculated to be 0.044 nM, 0.059 nM and 0.007 nM, respectively. The results indicated that bivalent etanercept and adalimumab possessed almost identical binding avidity to TNFα, but EnbCS6hFc exhibited more than 6-fold higher binding affinity than either etanercept or adalimumab. Since the soluble TNFα was coated on the microtiter plate, it behaves like the transmembrane form of TNFα expressing on the cell surface. It is conceivable that the avidity effect of the hexavalent form of EnbCS6hFc plays an important role in enhancing the overall binding strength toward the membrane target of TNFα.

Example 4

Competitive Displacement Binding Assays

Competitive displacement binding assays using NS0 cell stably expressing transmembrane TNFα on cell surface are presented to estimate the binding ability of antagonists to transmembrane TNFα. This method includes a preliminary saturation assay intended to define the optimal concentration of displaceable FITC-labeled etanercept followed by the determination of displacement constants (IC50). NS0 cells stably expressing the transmembrane TNFα were incubated with 2-fold serial dilutions of EnbCS6hFc, etanercept and adalimumab for 1 hr at 4° C. in phosphate buffered saline (PBS) containing 2% fetal bovine serum (fluorescence-activated cell sorting [FACS] buffer). A fixed, saturating amount (2.5 μg/ml, determined by flow cytometry) of fluorescein isothiocyanate (FITC)-conjugated etanercept was added directly. After incubation for 1 hour at 4° C., the cells were washed with FACS buffer three times and analyzed for immunofluorescence with a FACSCalibur flow cytometer (Becton Dickinson, San Jose, Calif., USA). The data are presented as percentage inhibition of maximal fluorescence intensity, which is defined as the mean fluorescence intensity obtained by staining the NS0 cells expressing the transmembrane TNFα with etanercept-FITC in the absence of TNFα antagonists. The concentration of each TNFα antagonist required to inhibit half the maximal fluorescence intensity (IC50) was calculated.

Figure 6:
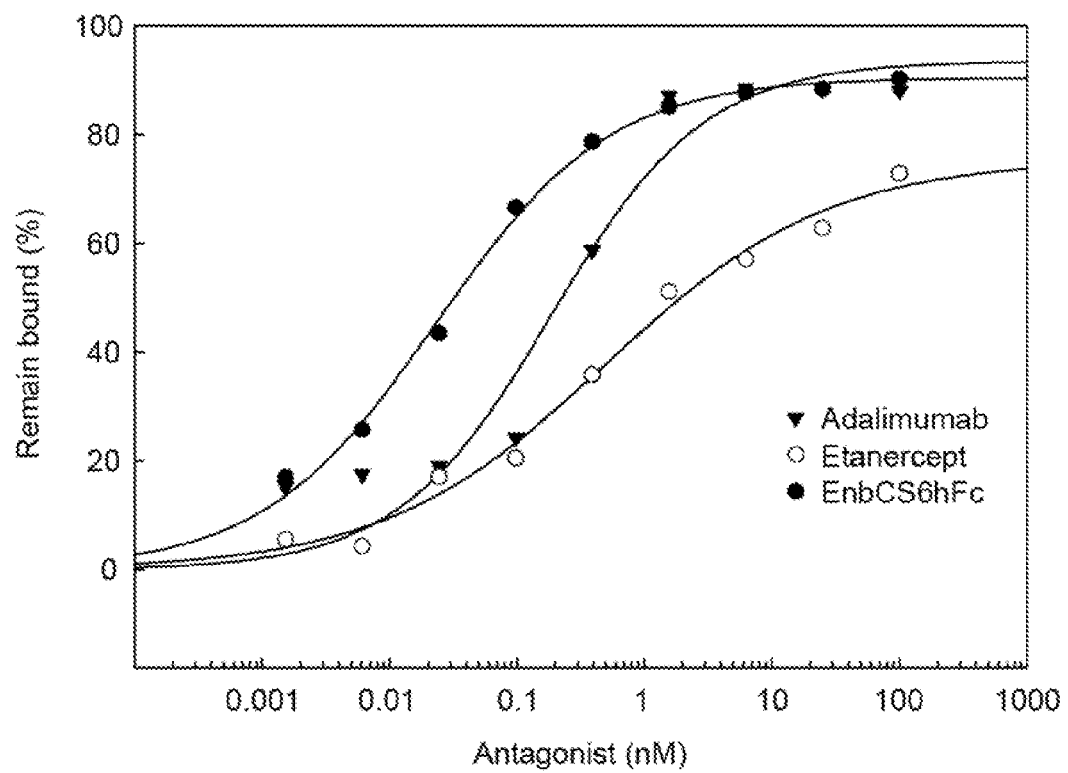
FIG. 6 depicts a competitive displacement binding assays according to the embodiments.

NS0 cells stably expressing the transmembrane TNFα were incubated with a serial dilution of adalimumab, etanercept, and EnbCS6hFc, respectively, at 4° C. for 1 hour. A saturated amount of FITC-conjugated etanercept was added and incubated for an additional hour. Cells were washed and the bound FITC-conjugated etanercept was quantified by flow cytometry. Values are expressed as percentage inhibition of maximal fluorescence intensity, which is defined as the mean fluorescence intensity obtained by adding FITC-conjugated etanercept without prior blocking of TNFα antagonists. As shown in FIG. 6, although the epitopes on TNFα are different in etanercept (TNFR2) and adalimumab, steric hindrance still prevents the adalimumab from binding it. The IC50 for EnbCS6hFc, adalimumab and etanercept were calculated to be 0.03 nM, 0.23 nM and 2.18 nM, respectively. The results indicated that EnbCS6hFc can bind to transmembrane TNFα stronger than other TNFα antagonists due to the avidity effect of multivalance.

Example 5

Stably Expression of Human Neonatal Fc Receptor (FcRn) on Chinese Hamster Ovary (CHO) Cells The neonatal Fc receptor (FcRn) is a non-covalently associated heterodimeric protein composed of a transmembrane anchored heavy chain (αFcRn) and a soluble light chain β2-microglobulin (β2m). The cDNAs encoding the open reading frames of both human αFcRn and β2m were cloned into the expression vector pSecTag2/Hygro (Invitrogen, San Diego, Calif.) and pCpG-mcs G2 (Invivogen, San Diego, Calif.), respectively. CHO-RD cells (RCB1477, RIKEN Bioresource Center, Japan) were co-transfected with the above expression constructs at a 1:1 ration using Effectene transfection reagent according to the manufacture's instruction. Cells were grown in F-12K medium containing 2% fetal bovine serum, 4 mM glutamine, sodium bicarbonate (3 g/L), and 400 μg/ml Hygromycin B for 3 weeks. Cells that are resistant to hygromycin and stably expressing functional human FcRn were sorted on a BD FACSAria system using fluorescein isothiocyanate conjugated anti-human β2-microglobulin (Clone 2M2, BioLegend, San Diego, Calif.). The sorted cells were subjected to limiting dilution in order to obtain several stable monoclones. Cells from each single clone were further analyzed by flow cytometry to determine the expression level of cell surface FcRn. The stable cell line with the highest expression level of human FcRn was picked for binding assays (see below).

Example 6

Binding of TNFα Antagonists to Human Neonatal Fc Receptor-Expressing CHO Cells

Figure 7:
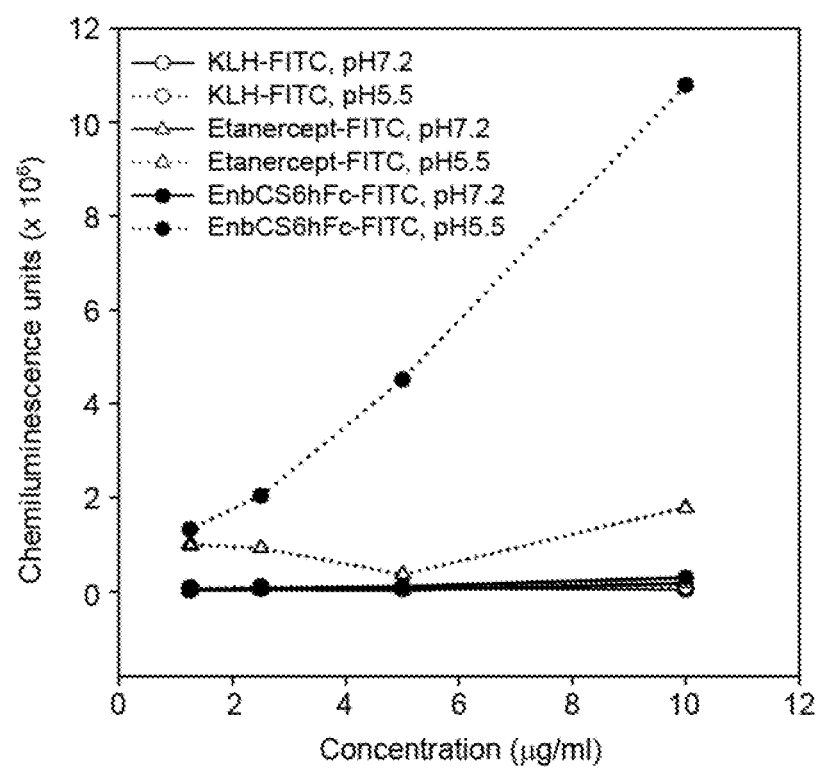
FIG. 7 depicts cell-based binding assays of human FcRn with TNFα antagonists by pH-dependent binding ELISA according to the embodiments.

To analyze whether the purified EnbCS6hFc can bind to the CHO cells stably expressing the human neonatal Fc receptor in a pH-dependent manner, cells were seeded in triplicate at $3 \times 10^5$ cells/well into a 96-well plate and cultured in F-12K medium containing 2% fetal bovine serum, 4 mM glutamine, sodium bicarbonate (3 g/L), and 400 μg/ml Hygromycin B for 16 hours. Cells were washed three times with either ice-cold 0.1 M of sodium acetate buffer (pH 5.5) or phosphate buffered saline (PBS, pH 7.2) and then incubated with different concentrations of fluorescein isothiocyanate (FITC)-conjugated keyhole limpet hemocyanin (KLH), etanercept, and EnbCS6hFc, respectively for 1 hr at 4° C. in either 0.1 M of sodium acetate buffer (pH 5.5) or phosphate buffered saline (PBS, pH 7.2). After incubation for 1 hour at 4° C., the cells were washed with the same buffer for three times and analyzed for immunofluorescence with a microplate reader. In FIG. 7, both etanercept and EnbCS6hFc showed the typical pH-dependent binding profiles (pH7.2 (solid line) or pH5.5 (dotted line)) with the CHO cells stably expressing the human neonatal Fc receptor. The binding of EnbCS6hFc was unexpectedly strong. The hexavalent EnbCS6hFc also unexpectedly exhibits a stronger binding affinity than etanercept to human FcRn in a dose-dependent manner at acidic pH 5.5, though it shows negligible binding at pH 7.2. FITC-conjugated KLH, which lacks Fc fragment, showing no binding affinity to human FcRn, was used as a negative control.

Example 7

Pharmacokinetic Assays

Figure 8:
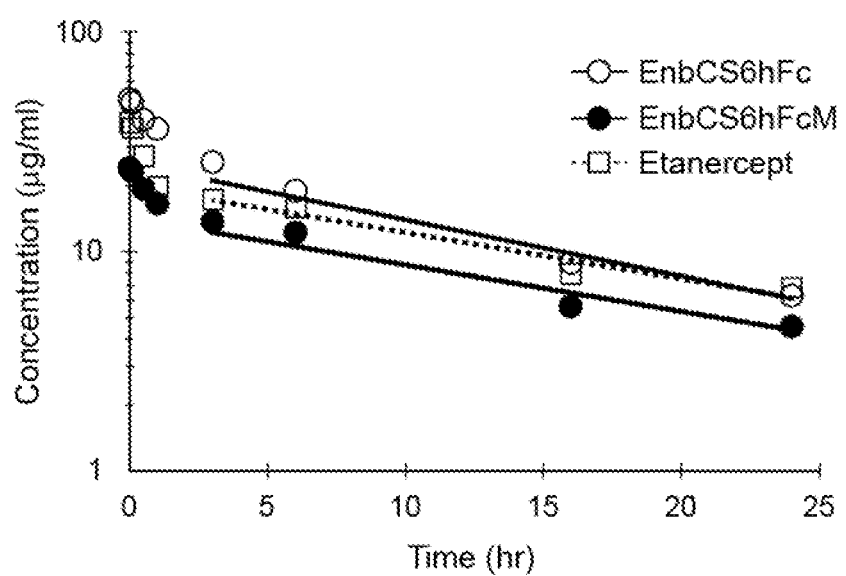
FIG. 8 depicts the blood clearance of etanercept, EnbCS6hFc and EnbCS6hFcM in mice according to the embodiments.

For pharmacokinetic assay, three groups (9 per group) of 7- to 8-week-old male BALB/c mice were used to analyze blood clearance of etanercept, EnbCS6hFc and EnbCS6hFcM, respectively. Following a pre-bleed, mice from each group were injected intravenously with 50 mg each of the above TNFα antagonists. During the next 24 h, periodic blood samples were collected. The amounts of each TNFα antagonist remaining in plasma were quantitated with recombinant TNFα (2 μg/ml) coated ELISA plates using horseradish peroxidase-conjugated goat anti-human IgG Fcγ fragment (Jackson ImmunoResearch Laboratories, Inc., West Grove, Pa.) as detecting antibody and 3,3',5,5',-tetramethylbenzidine as substrate. Absorbance was read at 450 nm on a microplate reader. The concentrations of each TNFα antagonist were fitted to a one-compartment elimination model using WinNonlin version 3.0 (Pharsight, Mountain View, Calif.). Results are averaged from 3 animals for each time point and are shown in FIG. 8.

Example 8

TNFα Neutralization Potency Assay

Neutralizing activities of adalimumab, etanercept, EnbCS6hFc, and EnbCS6hFcM against human TNFα were measured on the murine fibroblast L929 cells (ATCC Cat. No. CCL-1) treated with actinomycin D. L929 cells were seeded in triplicate at $3 \times 10^5$ cells/well into a 96-well plate and cultured in RPMI 1640 medium supplemented with 10% (v/v) fetal bovine serum for 16 hours. Then, 2-fold serial dilutions of adalimumab (▼), etanercept (Δ), EnbCS6hFc (●), and EnbCS6hFcM (○) were prepared in medium containing actinomycin D (2 μg/ml) and recombinant human TNFα (100 ng/ml) and incubated at 37° C. for 16 hours. After the supernatant was removed, 3-4,5-dimethylthiazol-2-yl-2,5-diphenyltetrazolium bromide (MTT) (5 mg/ml) (Sigma-Aldrich) was added and incubated in 37° C. for 4 hours. SDS solution (10%) was then added to the well. After 24 hours of incubation at room temperature, color in each well was recorded by colorimeter at 570 nm.

To examine the functional activity of the anti-TNFα antagonists, the ability of the antagonists to inhibit soluble TNFα activity was evaluated. TNFα causes cell cytotoxicity to murine L929 cells. Etanercept, adalimumab, EnbCS6hFc and EnbCS6hFcM were evaluated in L929 assays by co-incubation of antagonists with recombinant human TNFα. L929 cells were cultured with a 2-fold serial dilution of adalimumab, etanercept, EnbCS6hFc, and EnbCS6hFcM, respectively, containing actinomycin D (2 μg/ml) and recombinant human TNFα (100 ng/ml) at 37° C. for 16 hours. The cell variability was analyzed using a colorimetric MTT assay. As shown in FIG. 9, TNFα-mediated cytotoxicity in L929 cells treated with 100 ng/ml of human TNFα was effectively neutralized by these antagonists in a dose dependent manner, with ED50 values of 0.20 μg/ml, 0.23 μg/ml, 0.35 μg/ml and 0.10 μg/ml for etanercept, adalimumab, EnbCS6hFcM and EnbCS6hFc, respectively. The results indicated that EnbCS6hFc and EnbCS6hFcM exhibited the TNFα neutralization activity at concentrations similar to that of the TNFα antagonists which are available on the market.

Example 9

In Vivo Inhibition of Murine Collagen Antibody-Induced Arthritis with Etanercept and EnbCS6hFc For collagen antibody-induced arthritis experiments, 8- to 10-week old male BALB/c mice were purchased from the National Laboratory Animal Center (Nankang, Taiwan). Mice were maintained under a climate controlled environment in a 12-hour light/dark cycle. Arthritic mice were induced by intra-peritoneal (i.p.) injection of 3 mg/mouse of type II collagen specific antibodies (ArthritoMAB™ Arthritis Inducing Antibody Cocktail, MD Biosciences, Switzerland). Mice were further boosted with 100 μg lipopolysaccharides (MDLPS.5, MD Biosciences, Switzerland) by i.p. injection on day 3. Clinical arthritis scores were evaluated using a scale of 0-2 for each paw for a total score of 8. Paws were assigned a clinical score based on the scoring index: 0=normal; 0.25=one or two swollen toes; 0.5=three and four swollen toes; 0.75=slightly swollen footpad or ankle; 1=swollen footpad or ankle; 1.25=one or two swollen toes and swollen footpad or ankle; 2.0=swollen toes and swollen footpad and swollen ankle. At the time of disease onset, mice were administered by i.p. injection of 100 μl phosphate buffered slaine, etanercept (50 μg) or EnbCS6hFc (50 μg) once daily for 10 consecutive days. The arthritis scores were compared between the non-treated (n=2), etanercept (n=4) and EnbCS6hFc (n=4) treated groups during the course of treatment. Scoring results were expressed as mean±standard deviation (SD). Statistical differences between the control (phosphate buffered saline). The results showed that mice treated with EnbCS6hFc progressed to significantly less severe disease than either the non-treated or the etanercept-treated group (P<0.05).

It will be apparent to those skilled in the art that various modifications and variations can be made to the disclosed embodiments. It is intended that the specification and examples be considered as exemplary only, with a true scope of the disclosure being indicated by the following claims and their equivalents.

---

The invention claimed is:

1. A fusion protein comprising three or six monomer polypeptides, wherein each monomer polypeptide independently comprises:
   (a) a single domain antibody, or an extracellular domain of a TNF receptor in a TNF receptor family,
   (b) a collagen-like domain comprising at least 8 G-P-X1 blocks, a trimerizing motif, and wherein X1 is P or O,
   (c) optionally, a hinge region of IgG or a glycine linker, and
   (d) an Fc domain comprising the CH2 and CH3 regions of human IgG
   wherein the trimerizing motif comprises SEQ ID NO: 34, or a variation thereof which comprises one or more of the following structures: SEQ ID NO: 40, SEQ ID NO: 41, SEQ ID NO: 42, SEQ ID NO: 43, SEQ ID NO: 44, and SEQ ID NO: 45.

2. The fusion protein of claim 1, wherein the extracellular domain of a TNF receptor family is the sequence of the extracellular domain of at least one TNF receptor selected from the group consisting of TNFαRII (p55), TNFR type II (p75), Fas (CD95), CD40, CD27, CD30, 4-1BB (CDw137), OX40 (CD134), LTBR, NGFR (CD271), DcR3, TRAILR-1 (CD261), TRAILR-2 (CD262), TRAILR-3 (CD263), TRAILR-4 (CD264), RANK (CD265), OPG (TR1), FN14 (CD266), TACI (CD267), BAFFR (CD268), HVEM (CD270), BCM (CD269), GITR (CD357), TAJ-alpha (TROY), DR6 (CD358), and DR3 (TRAMP).

3. The fusion protein of claim 1, wherein the trimerizing motif is located in between two G-P-X1 blocks.

4. The fusion protein of claim 1, wherein in each monomer polypeptide, the collagen-like domain amino acid sequence is selected from group consisting of:
SEQ ID NO: 23, SEQ ID NO: 24, SEQ ID NO: 35, SEQ ID NO: 22, and SEQ ID NO: 25.

5. The fusion protein of claim 1, wherein the Fc domain is C-terminal to the collagen-like domain.

6. The fusion protein of claim 2, wherein the extracellular domain of a TNF receptor in a TNF receptor family is the extracellular domain of TNFR type II (p75).

7. The fusion protein of claim 1, wherein the trimerizing motif comprises SEQ ID NO: 40.

8. The fusion protein of claim 4, wherein in each monomer polypeptide, the collagen-like domain amino acid sequence is SEQ ID NO: 22.

9. A kit comprising the fusion protein of claim 1.

10. A fusion protein comprising three or six monomer polypeptides:
    where each monomer polypeptide independently comprises an amino acid sequence having at least 90, 92, 95, 97, 99, or 100% sequence identity to at least one of the amino acid sequences selected from the group consisting of SEQ ID NOs: 1, 3, 5, 7, 9, 11, and 13, and wherein the polypeptides bind to and inhibit TNFα.

11. A fusion protein comprising three or six monomer polypeptides:
    where each monomer polypeptide independently comprises an amino acid sequence having at least 90, 92, 95, 97, 99, or 100% sequence identity to SEQ ID NO: 9, and wherein the polypeptides bind to and inhibit TNFα.

12. A nucleic acid encoding a monomer polypeptide of the fusion protein of claim 1.

13. An expression vector that expresses the fusion protein of claim 1.

14. An isolated host cell comprising the expression vector of claim 13.

15. A method of lowering the level of TNFα signaling in vivo comprising administering to a patient in need thereof an effective amount of a protein comprising:
a fusion protein having three or six monomer polypeptides, wherein each polypeptide comprises:
(a) a single domain antibody or an extracellular domain of a TNF receptor in a TNF receptor family,
(b) a collagen-like domain comprising at least 8 G-P-X1 blocks, a trimerizing motif, and wherein X1 is P or O,
(c) optionally, a hinge region of IgG or a glycine linker, and
(d) an Fc domain comprising the CH2 and CH3 regions of human IgG
wherein the trimerizing motif comprises SEQ ID NO: 34, or a variation thereof which comprises one or more of the following structures: SEQ ID NO: 40, SEQ ID NO: 41, SEQ ID NO: 42, SEQ ID NO: 43, SEQ ID NO: 44, and SEQ ID NO: 45.

16. A method of treating one or more of rheumatoid arthritis, inflammatory bowel disease, psoriatic arthritis, vasculitis, ankylosing spondylitis, and juvenile chronic arthritis comprising administering to a patient in need thereof an effective amount of a composition comprising:
a fusion protein comprising three or six monomer polypeptides, wherein each polypeptide comprises:
(a) an extracellular domain of a TNF receptor in a TNF receptor family,
(b) a collagen-like domain comprising at least 8 G-P-X1 blocks, a trimerizing motif, wherein X1 is P or O, wherein the trimerizing motif comprises SEQ ID NO: 34, or a variation thereof which comprises one or more of the following structures: SEQ ID NO: 40, SEQ ID NO: 41, SEQ ID NO: 42, SEQ ID NO: 43, SEQ ID NO: 44, and SEQ ID NO: 45,
(c) optionally a hinge region of IgG or a glycine linker, and
(d) an Fc domain comprising the CH2 and CH3 regions of human IgG,
in a pharmaceutically acceptable carrier.

17. The method of claim 16, comprising administering 0.01-100.0 mg/kg of the composition.

* * * * *